US012760101B2

(12) United States Patent
Pardoll et al.

(10) Patent No.: US 12,760,101 B2
(45) Date of Patent: Oct. 13, 2026

(54) COMPOSITIONS AND METHODS FOR IDENTIFYING FUNCTIONAL ANTI-TUMOR T CELL RESPONSES

(71) Applicant: The Johns Hopkins University, Baltimore, MD (US)

(72) Inventors: Drew M. Pardoll, Brookeville, MD (US); Kellie Smith, Baltimore, MD (US); Franck Housseau, Ashburn, VA (US); Victor Velculescu, Baltimore, MD (US); Valsamo Anagnostou, Baltimore, MD (US); Luis Diaz, Baltimore, MD (US); Bert Vogelstein, Baltimore, MD (US); Ken Kinzler, Bel Air, MD (US); Nickolas Papadopoulos, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 665 days.

(21) Appl. No.: 16/341,862

(22) PCT Filed: Oct. 13, 2017

(86) PCT No.: PCT/US2017/056557
§ 371 (c)(1),
(2) Date: Apr. 12, 2019

(87) PCT Pub. No.: WO2018/071796
PCT Pub. Date: Apr. 19, 2018

(65) Prior Publication Data

US 2019/0240257 A1 Aug. 8, 2019

Related U.S. Application Data

(60) Provisional application No. 62/407,820, filed on Oct. 13, 2016.

(51) Int. Cl.

| | |
|---|---|
| ***C07K 16/28*** | (2006.01) |
| ***A61K 35/17*** | (2025.01) |
| ***A61K 39/00*** | (2006.01) |
| ***A61K 39/395*** | (2006.01) |
| ***A61K 39/42*** | (2006.01) |
| ***A61P 31/12*** | (2006.01) |
| ***A61P 35/00*** | (2006.01) |
| ***C07K 14/705*** | (2006.01) |
| ***C12N 5/0783*** | (2010.01) |
| ***C12Q 1/6886*** | (2018.01) |
| ***G01N 33/50*** | (2006.01) |
| ***G01N 33/575*** | (2026.01) |

(52) U.S. Cl.
CPC .......... *C07K 16/2818* (2013.01); *A61K 35/17* (2013.01); *A61K 39/395* (2013.01); *A61K 39/39558* (2013.01); *A61K 39/42* (2013.01); *A61P 31/12* (2018.01); *A61P 35/00* (2018.01); *C07K 14/7051* (2013.01); *C12N 5/0636* (2013.01); *C12Q 1/6886* (2013.01); *G01N 33/505* (2013.01); *G01N 33/575* (2026.01); *A61K 2039/505* (2013.01); *A61K 2039/5156* (2013.01); *A61K 2039/55* (2013.01); *A61K 2039/572* (2013.01); *A61K 2039/6006* (2013.01); *C07K 2317/76* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 5,500,362 | A | 3/1996 | Robinson et al. | |
| 5,641,870 | A | 6/1997 | Rinderknecht et al. | |
| 5,821,337 | A | 10/1998 | Carter et al. | |
| 9,115,402 | B2 * | 8/2015 | Hacohen ............ | A61K 39/0011 |
| 2015/0275296 | A1 * | 10/2015 | Klinger ................ | C12Q 1/6881 506/9 |

FOREIGN PATENT DOCUMENTS

| | | | | | |
|---|---|---|---|---|---|
| EP | 0404097 | A2 | 12/1990 | | |
| WO | 199301161 | A1 | 1/1993 | | |
| WO | WO-2016146618 | A1 * | 9/2016 | .............. | A61P 31/20 |

OTHER PUBLICATIONS

Klinger et al. 2013, PLOS one, vol. 8: 1-9.*
Vondergeide et al., 2013, Nat. Med. vol. 9: 1098-1100.*
Hackl, Aug. 2016, Nat. Rev. vol. 17: 441-458.*
P. Singleton and D. Sainsbury, Dictionary of Microbiology and Molecular Biology, Second Edition. 1987.
Chothia C., & Lesk, A. M. (1987). Canonical structures for the hypervariable regions of immunoglobulins. Journal of molecular biology, 196(4), 901-917. https://doi.org/10.1016/0022-2836(87)90412-8.
Lefranc M. P., Giudicelli, V., Ginestoux, C., Bodmer, J., Müller, W., Bontrop, R., Lemaitre, M., Malik, A., Barbié, V., & Chaume, D. (1999). IMGT, the international ImMunoGeneTics database. Nucleic acids research, 27(1), 209-212. https://doi.org/10.1093/nar/27.1.209.
Ruiz, Véronique Giudicelli, Chantal Ginestoux, Peter Stoehr, James Robinson, Julia Bodmer, Steven G. E. Marsh, Ronald Bontrop, Marc Lemaitre, Gérard Lefranc, Denys Chaume, Marie-Paule Lefranc, IMGT, the international ImMunoGeneTics database, Nucleic Acids Research, vol. 28, Issue 1, Jan. 1, 2000, pp. 219-221, https://doi.org/10.1093/nar/28.1.219.
Honegger A., & Plückthun, A. (2001). Yet another numbering scheme for immunoglobulin variable domains: an automatic modeling and analysis tool. Journal of molecular biology, 309(3), 657-670. https://doi.org/10.1006/jmbi.2001.4662.
Kohler G., & Milstein, C. (1975). Continuous cultures of fused cells secreting antibody of predefined specificity. Nature, 256(5517), 495-497. https://doi.org/10.1038/256495a0.

(Continued)

*Primary Examiner* — Amy E Juedes
(74) *Attorney, Agent, or Firm* — Fox Rothschild LLP

(57) ABSTRACT

The invention features compositions and methods for identifying functional anti-tumor T cell responses.

5 Claims, 13 Drawing Sheets

Specification includes a Sequence Listing.

(56) References Cited

OTHER PUBLICATIONS

Clackson T., Hoogenboom, H. R., Griffiths, A. D., & Winter, G. (1991). Making antibody fragments using phage display libraries. Nature, 352(6336), 624-628. https://doi.org/10.1038/352624a0.
Marks J. D., Hoogenboom, H. R., Bonnert, T. P., McCafferty, J., Griffiths, A. D., & Winter, G. (1991). By-passing immunization. Human antibodies from V-gene libraries displayed on phage. Joumal of molecular biology, 222(3), 581-597. https://doi.org/10.1016/0022-2836(91)90498-u.
Morrison SL, Johnson MJ, Herzenberg LA, Oi VT. Chimeric human antibody molecules: mouse antigen-binding domains with human constant region domains. Proc Natl Acad Sci U S A. 1984;81(21):6851-6855. doi:10.1073/pnas.81.21.6851.
Jones, P. T., Dear, P. H., Foote, J., Neuberger, M. S., & Winter, G. (1986). Replacing the complementarity-determining regions in a human antibody with those from a mouse. Nature, 321(6069), 522-525. https://doi.org/10.1038/321522a0.
Riechmann, L., Clark, M., Waldmann, H., & Winter, G. (1988). Reshaping human antibodies for therapy. Nature, 332 (6162), 323-327. https://doi.org/10.1038/332323a0.
Presta L. G. (1992). Antibody engineering. Current opinion in biotechnology, 3(4), 394-398. https://doi.org/10.1016/0958-1669(92)90168-i.
Verhoeyen, M., Milstein, C., & Winter, G. (1988). Reshaping human antibodies: grafting an antilysozyme activity. Science (New York, N.Y.), 239(4847), 1534-1536. https://doi.org/10.1126/science.2451287.
Zapata, G., Ridgway, J. B., Mordenti, J., Osaka, G., Wong, W. L., Bennett, G. L., & Carter, P. (1995). Engineering linear F(ab')2 fragments for efficient production in *Escherichia coli* and enhanced antiproliferative activity. Protein engineering, 8(10), 1057-1062. https://doi.org/10.1093/protein/8.10.1057.
Holliger P., Prospero, T., & Winter, G. (1993). "Diabodies": small bivalent and bispecific antibody fragments. Proceedings of the National Academy of Sciences of the United States of America, 90(14), 6444-6448. https://doi.org/10.1073/pnas.90.14.6444.
Scatchard et al. (Ann. N.Y. Acad. Sci. USA 51:660 (1949)).
Ravetch J. V., & Kinet, J. P. (1991). Fc receptors. Annual review of immunology, 9, 457-492. https://doi.org/10.1146/annurev.iy.09.040191.002325.
Clynes, R., Takechi, Y., Moroi, Y., Houghton, A., & Ravetch, J. V. (1998). Fc receptors are required in passive and active immunity to melanoma. Proceedings of the National Academy of Sciences of the United States of America, 95(2), 652-656. https://doi.org/10.1073/pnas.95.2.652.
Wahl GM, Berger SL (1987) Screening colonies or plaques with radioactive nucleic acid probes. Methods Enzymol 152: 415-423.
Wahl GM, Berger SL, Kimmel AR (1987) Molecular hybridization of immobilized nucleic acids: Theoretical concepts and practical considerations. Methods Enzymol 152: 399-407.
Kimmel, "Identification and Characterization of Specific Clones: Strategy for Confirming the Validity of Presumptive Clones," Methods in Enzymol; 152:507-511, 1987.
Grunstein, M., & Hogness, D. S. (1975). Colony hybridization: a method for the isolation of cloned DNAs that contain a specific gene. Proceedings of the National Academy of Sciences of the United States of America, 72(10), 3961-3965. https://doi.org/10.1073/pnas.72.10.3961.
Benton, W. D., & Davis, R. W. (1977). Screening lambdagt recombinant clones by hybridization to single plaques in situ. Science (New York, N.Y.), 196(4286), 180-182. https://doi.org/10.1126/science.322279.
Rattan Sis, Derventzi A, Clark BFC. Protein synthesis, post-translational modifications and aging. Ann NY Acad Sci 1992; 663:48-62.Remington's Pharmaceutical Sciences by E. W. Martin.
Valsamo Anagnastou, Kellie N. Smith, Patrick M. Forde, Noushin Niknafs, Rohit Bhattacharya, James White, et al., Evolution of Neoantigen Landscape during Immune Checkpoint Blockade in Non-Small Cell Lung Cancer. Can. Disc. 7: 264-276 (2017).
Sausen M., Leary, R., Jones, S. et al. Integrated genomic analyses identify ARID1A and ARID1B alterations in the childhood cancer neuroblastoma. Nat Genet 45, 12-17 (2013). https://doi.org/10.1038/ng.2493.
Jones S, Anagnostou V, Lytle K, et al. Personalized genomic analyses for cancer mutation discovery and interpretation. Sci Transl Med. 2015;7(283):283ra53. doi:10.1126/scitranslmed.aaa7161.
Bertotti, A., Papp, E., Jones, S. et al. The genomic landscape of response to EGFR blockade in colorectal cancer. Nature 526, 263-267 (2015). https://doi.org/10.1038/nature14969.
Needleman S. B., & Wunsch, C. D. (1970). A general method applicable to the search for similarities in the amino acid sequence of two proteins. Journal of molecular biology, 48(3), 443-453. https://doi.org/10.1016/0022-2836(70)90057-4.
András Szolek, Benjamin Schubert, Christopher Mohr, Marc Sturm, Magdalena Feldhahn, Oliver Kohlbacher, OptiType: precision HLA typing from next-generation sequencing data, Bioinformatics, vol. 30, Issue 23, Dec. 1, 2014, pp. 3310-3316, https://doi.org/10.1093/bioinformatics/btu548.
Nielsen M, Andreatta M. NetMHCpan-3.0; improved prediction of binding to MHC class I molecules integrating information from multiple receptor and peptide length datasets. Genome Med. 2016;8:33.
Lundegaard, C. et al. NetMHC-3.0: accurate web accessible predictions of human, mouse and monkey MHC class I affinities for peptides of length 8-11. Nucleic Acids Res 36, W509-512, doi: 10.1093/nar/gkn202 (2008).
Lundegaard C., Lund, O., & Nielsen, M. (2008). Accurate approximation method for prediction of class I MHC affinities for peptides of length 8, 10 and 11 using prediction tools trained on 9mers. Bioinformatics (Oxford, England), 24(11), 1397-1398. https://doi.org/10.1093/bioinformatics/btn128.
Stranzl T., Larsen, M.V., Lundegaard, C. et al. NetCTLpan: pan-specific MHC class I pathway epitope predictions. Immunogenetics 62, 357-368 (2010). https://doi.org/10.1007/s00251-010-0441-4.
Kim Y, Sidney J, Pinilla C, Sette A, Peters B: Derivation of an amino acid similarity matrix for peptide: MHC binding and its application as a Bayesian prior. BMC Bioinforma 2009, 10: 394. 10.1186/1471-2105-10-394.
Le DT, Durham JN, Smith KN, et al. Mismatch repair deficiency predicts response of solid tumors to PD-1 blockade. Science. 2017;357(6349):409-413. doi:10.1126/science.aan6733.
Carlson C. S., Emerson, R. O., Sherwood, A. M., Desmarais, C., Chung, M. W., Parsons, J. M., Steen, M. S., LaMadrid-Herrmannsfeldt, M. A., Williamson, D. W., Livingston, R. J., Wu, D., Wood, B. L., Rieder, M. J., & Robins, H. (2013). Using synthetic templates to design an unbiased multiplex PCR assay. Nature communications, 4, 2680. https://doi.org/10.1038/ncomms3680.
Robins, H. S., Campregher, P. V., Srivastava, S. K., Wacher, A., Turtle, C. J., Kahsai, O., Riddell, S. R., Warren, E. H., & Carlson, C. S. (2009). Comprehensive assessment of T-cell receptor beta-chain diversity in alphabeta T cells. Blood, 114(19), 4099-4107. https://doi.org/10.1182/blood-2009-04-217604.
Gentleman, R.C., Carey, V.J., Bates, D.M. et al. Bioconductor: open software development for computational biology and bioinformatics. Genome Biol 5, R80 (2004). https://doi.org/10.1186/GB-2004-5-10-r80.
Benjamini Y. and Hochberg, Y. (1995) Controlling the false discovery rate: a practical and powerful approach to multiple testing. J. R. Statist. Soc. B, 57, 289-300.
Price Da, Asher TE, Wilson NA, et al. Public clonotype usage identifies protective Gag-specific CD8+ T cell responses in SIV infection. The Journal of Experimental Medicine. Apr. 2009;206(4):923-936. DOI: 10.1084/jem.20081127.
Valkenburg SA, Josephs TM, Clemens EB, et al. Molecular basis for universal HLA-A*0201-restricted CD8+ T-cell immunity against influenza viruses. Proceedings of the National Academy of Sciences of the United States of America. Apr. 2016;113(16):4440-4445. DOI: 10.1073/pnas.1603106113.
Victor Y. Du, Anju Bansal, Jonathan Carlson, Jesus F. Salazar-Gonzalez, Maria G. Salazar, Kristin Ladell, Stephanie Gras, Tracy M. Josephs, Sonya L. Heath, David A. Price, Jamie Rossjohn, Eric Hunter, Paul A. Goepfert HIV-1-Specific CD8 T Cells Exhibit

(56) References Cited

OTHER PUBLICATIONS

Limited Cross-Reactivity during Acute Infection The Journal of Immunology Apr. 15, 2016, 196 (8) 3276-3286; DOI: 10.4049/jimmunol.1502411.
Kloverpris HN, McGregor R, McLaren JE, et al. CD8+ TCR Bias and Immunodominance in HIV-1 Infection. J Immunol. 2015;194(11):5329-5345. doi:10.4049/jimmunol.1400854.
Hill, B. J., Darrah, P. A., Ende, Z., Ambrozak, D. R., Quinn, K. M., Darko, S., Gostick, E., Wooldridge, L., van den Berg, H. A., Venturi, V., Larsen, M., Davenport, M. P., Seder, R. A., Price, D. A., & Douek, D. C. (2014). Epitope specificity delimits the functional capabilities of vaccine-induced CD8 T cell populations. Journal of immunology (Baltimore, Md. : 1950), 193(11), 5626-5636. https://doi.org/10.4049/jimmunol.1401017.
Motozono C, Kuse N, Sun X, et al. Molecular basis of a dominant T cell response to an HIV reverse transcriptase 8-mer epitope presented by the protective allele HLA-B*51:01. J Immunol. 2014;192(7):3428-3434. doi:10.4049/jimmunol.1302667.
Wu C, Zanker D, Valkenburg S, et al. Systematic identification of immunodominant CD8+ T-cell responses to influenza A virus in HLA-A2 individuals. Proc Natl Acad Sci U S A. 2011;108(22):9178-9183. doi:10.1073/pnas.1105624108.
Steven NM, Annels NE, Kumar A, Leese AM, Kurilla MG, Rickinson AB. Immediate early and early lytic cycle proteins are frequent targets of the Epstein-Barr virus-induced cytotoxic T cell response. J Exp Med. 1997;185(9):1605-1617. doi:10.1084/jem.185.9.1605.
Betts MR, Nason MC, West SM, et al. HIV nonprogressors preferentially maintain highly functional HIV-specific CD8 + T cells. Blood. 2006;107(12):4781-4789. doi:10.1182/blood-2005-12-4818.
Couzin-Frankel J. Cancer immunotherapy. Science 2013; 342(6165):1432-1433. doi: 10.1126/science.342.6165.1432.

* cited by examiner c d

| pMHC+-matched clonotypes | Frequency in EBV EBNA 4NP pMHC+population | | Frequency among uncultured, baseline T cells | Frequency after 10 day culture |
|---|---|---|---|---|
| | Sort #1 | Sort #2 | | |
| CASSLTSATGELFF | 43.98 | 41.7 | 0.13 | 17.31 |
| CASSLTSAAGELFF | 37.65 | 38.7 | 0.14 | 21.21 |
| CASSPTSATGELFF | 7.79 | 7.74 | 0.02 | 7.93 |
| CASSLKGTRDQETQYF | 0.58 | 0.79 | 0.01 | 1.63 |

b

COMPOSITIONS AND METHODS FOR IDENTIFYING FUNCTIONAL ANTI-TUMOR T CELL RESPONSES

CROSS REFERENCE TO RELATED APPLICATIONS

This application claims the benefit of priority under 35 U.S.C. § 119(e) to U.S. Provisional Application No. 62/407,820, filed Oct. 13, 2017, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 16, 2026, is named 348358_03301_SL.txt and is 62,638 bytes in size.

FIELD OF THE INVENTION

This invention relates generally to the field of oncology and virology.

BACKGROUND OF THE INVENTION

With the emergence of immunotherapy as a major clinical treatment for cancer, it has become clear that T cells are the primary cells that provide specific recognition of the cancer and mediate direct killing as well as orchestrate innate anti-tumor responses. As such, prior to the invention described herein, there was a pressing need to develop methodologies to rapidly, sensitively, and specifically assess functional anti-tumor T cell responses.

SUMMARY OF THE INVENTION

The invention is based, at least in part, on the surprising identification of a sensitive, specific, scalable, and simple method to identify functional anti-tumor T cell responses, i.e., mutation associated neoantigens (MANA) functional expansion of specific T cells (MANAFEST), virus antigen functional expansion of specific T cells (VIRAFEST), and tumor-associated antigen (TAAFEST).

Provided are methods of functionally evaluating a candidate antigen for the ability to induce a T cell response. The method includes obtaining a test sample from a subject, e.g., a human subject, having or at risk of developing a cancer or a viral infection. Suitable samples include a blood sample or a plasma sample. In some cases, a reference sample is obtained from healthy normal tissue from the same individual as the test sample or from one or more healthy normal tissues from different individuals. In other cases, the test sample is obtained from the tumor or the tumor microenvironment.

Next, a candidate antigen is provided. Preferably, the candidate antigen is identified by analyzing whole genome sequencing data from tumor and matched normal control samples.

Subsequently, the method provides for expanding autologous T cells from the subject; isolating deoxyribonucleic acid (DNA) from the T cells; amplifying the T cell receptor-β(TCR-β) complementarity-determining region 3 (CDR3) DNA; determining a level of antigen-specific T cell expansion; comparing the level of antigen-specific T cell expansion to a level of expansion of T cells in the absence of the candidate peptide. Finally, it is determined that the candidate antigen has the ability to induce a T cell response if the level of antigen-specific T cell expansion is higher than the level of expansion of T cells in the absence of the candidate peptide.

For example, the level of antigen-specific T cell expansion is at least 1% higher, e.g., at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% higher than the level of expansion of T cells in the absence of the candidate peptide. Alternatively, the level of antigen-specific T cell expansion is increased by at least 2 fold, at least 3 fold, at least 4 fold, at least 5 fold, at least 6 fold, at least 7 fold, at least 8 fold, at least 9 fold, at least 10 fold, at least 15 fold, at least 20 fold, at least 25 fold, at least 30 fold, at least 35 fold, at least 40 fold, at least 45 fold, at least 50 fold, at least 60 fold, at least 70 fold, at least 80 fold, at least 90 fold, at least 100 fold, at least 125 fold, at least 150 fold, at least 175 fold, at least 200 fold, at least 250 fold, at least 300 fold, at least 350 fold, at least 400 fold or at least 500 fold as compared to the level of expansion of T cells in the absence of the candidate peptide.

In one aspect, the autologous T cells from the subject are stimulated to expand with the candidate antigen or with autologous peripheral blood mononuclear cells (PBMCs) which have been transfected with a tandem minigene construct encoding the candidate antigen.

In certain embodiments, a candidate agent comprises a peptide, a protein or a minigene transfected into autologous cells, such as, monocytic cells.

For example, antigen-specific T cell expansion is determined by comparing TCR-Vβ clonality prior to stimulation with the candidate antigen or PBMCs to TCR-Vβ clonality after stimulation with the candidate antigen, e.g., by TCRseq to analyze expansion of T cell clones.

Optionally, the candidate antigen comprises a tumor antigen, e.g., those derived from tumor-specific mutations, or a viral antigen. For example, the candidate antigen comprises a mutation-associated neoantigen (MANA) nucleotide, a MANA peptide, a viral nucleotide, a viral peptide, a non-mutated tumor-associated antigen nucleotide, or a non-mutated tumor-associated antigen peptide. In some cases, the viral antigen is expressed by an integrated cancer-associated virus or a non-oncogenic virus. For example, the integrated cancer-associated virus comprises human papilloma virus (HPV) associated with cervical or head and neck cancer, Epstein Barr virus (EBV), Merkel Cell Polyomavirus, Hepatitis B virus (HBV) or Hepatitis C virus (HCV). In another example, the non-oncogenic virus comprises human immunodeficiency virus (HIV).

In some cases, T cell expansion occurs in the absence of detectable cytokine production as measured by an enzyme-linked immunospot (ELISPOT) assay.

Methods of determining whether immunotherapy will inhibit a tumor in a subject are carried out by functionally evaluating a candidate antigen for the ability to induce a T cell response according to the methods described herein; and determining that immunotherapy will inhibit the tumor if the candidate antigen has the ability to induce a T cell response, wherein the immunotherapy comprises administering an antagonist of the candidate antigen to the subject, thereby determining whether immunotherapy will inhibit the tumor.

In some cases, the method further comprises administering the antagonist of the candidate antigen to the subject.

Optionally, it is determined whether immunotherapy will inhibit a tumor prior to or subsequent to administration of the immunotherapy to the subject. That is, the methods described herein may be used prior to immunotherapy as a biomarker for predicting response to the immunotherapy employed. Alternatively, the methods described herein are utilized after initiation of immunotherapy as a biomarker for predicting response to the immunotherapy employed prior to conventional response measurements, thereby allowing earlier therapeutic decisions that are not possible using conventional response measurements.

In one aspect, the immunotherapy comprises administration of an immune checkpoint inhibitor. Suitable immune checkpoint inhibitors include a small molecule inhibitor, an antibody or a fragment thereof (e.g., an anti-PD-1 monoclonal antibody), or a nucleic acid molecule. For example, the nucleic acid molecule comprises double stranded ribonucleic acid (dsRNA), small hairpin RNA or short hairpin RNA (shRNA), or antisense RNA, or any portion thereof.

A small molecule is a compound that is less than 2000 daltons in mass. Typically, small molecules are less than one kilodalton. The molecular mass of the small molecule is preferably less than 1000 daltons, more preferably less than 600 daltons, e.g., the compound is less than 500 daltons, 400 daltons, 300 daltons, 200 daltons, or 100 daltons.

Small molecules are organic or inorganic. Exemplary organic small molecules include, but are not limited to, aliphatic hydrocarbons, alcohols, aldehydes, ketones, organic acids, esters, mono- and disaccharides, aromatic hydrocarbons, amino acids, and lipids. Exemplary inorganic small molecules comprise trace minerals, ions, free radicals, and metabolites. Alternatively, small molecule inhibitors can be synthetically engineered to consist of a fragment, or small portion, or a longer amino acid chain to fill a binding pocket of an enzyme.

Exemplary immune checkpoint inhibitors include an anti-cytotoxic T-lymphocyte-associated protein 4 (CTLA4) antibody, an anti-programmed cell death protein 1 (PD-1) antibody, an anti-programmed death-ligand 1 (PD-L1) antibody, an anti-lymphocyte-activation 3 (LAG3) antibody, an anti-T-cell immunoglobulin and mucin-domain containing-3 (TIM-3) antibody, an anti-T-cell immunoreceptor with Ig and immunoreceptor tyrosine-based inhibition motif (ITIM) domains (TIGIT) antibody, an anti-V domain-containing Ig suppressor of T-cell activation antibody, an anti-cluster of differentiation 47 (CD47) antibody, an anti-signal regulatory alpha (SIRP α) antibody, an anti-B7-H3 antibody, an anti-B7-H4 antibody, an anti-neuritin antibody, an anti-neuropilin antibody, and an anti-interleukin-35 (IL-35) antibody, or any combination thereof.

In another aspect, the immune checkpoint inhibitor comprises a drug that inhibits indoleamine-pyrrole 2,3-dioxygenase (IDO), A2A adenosine receptor (A2AR), arginase, or glutaminase, or any combination thereof.

For example, the immune checkpoint inhibitor is administered at a dose of 1 mg/kg/day-1 g/kg/day. For example, the immune checkpoint inhibitor is administered at a dosage of 0.01-10 mg/kg (e.g., 0.01, 0.05, 0.1, 0.5, 1, 5, or 10 mg/kg) bodyweight. For example, the immune checkpoint inhibitor is administered in an amount of 0.01-30 mg (e.g., 0.01, 0.05, 0.1, 0.5, 1, 5, 10, 20, or 30 mg) per dose. In another example, the immune checkpoint inhibitor is administered in the dose range of 0.1 mg/kg to 10 mg/kg of body weight.

In some cases, the method further comprises administering an agonist of a co-stimulatory receptor. Exemplary agonists include an anti-glucocorticoid-induced tumor necrosis factor receptor (TNFR)-related protein (GITR) antibody, an anti-CD27 antibody, an anti-4-1BB antibody, an anti-OX40 antibody, an anti-inducible T-cell co-stimulator (ICOS) antibody, and an anti-CD40 antibody, or any combination thereof.

Also provided are methods of determining whether a vaccine will inhibit a tumor or a virus in a subject comprising functionally evaluating a candidate antigen for the ability to induce a T cell response according to the methods described herein; and determining that the vaccine will inhibit the tumor or virus if the candidate antigen has the ability to induce a T cell response, wherein the vaccine comprises an agonist of the candidate antigen, thereby determining whether the vaccine will inhibit the tumor or virus. In some cases, the methods also include administering the vaccine to the subject.

For example, the vaccine comprises the candidate peptide or a tandem minigene encoding the candidate antigen incorporated into a recombinant viral or bacterial vaccine. In one aspect, the candidate antigen comprises a tumor antigen or a viral antigen. For example, the candidate antigen comprises a mutation-associated neoantigen (MANA) or a non-mutated tumor-associated antigen. In another aspect, the viral antigen is expressed by an integrated cancer-associated virus or a non-oncogenic virus.

Preferably, the methods described herein inhibit the growth or progression of cancer, e.g., a tumor, or a viral infection in a subject. For example, the methods described herein inhibit the growth of a tumor by at least 1%, e.g., by at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 60%, at least 70%, at least 80%, at least 90% or 100%. In other cases, the methods described herein reduce the size of a tumor by at least 1 mm in diameter, e.g., by at least 2 mm in diameter, by at least 3 mm in diameter, by at least 4 mm in diameter, by at least 5 mm in diameter, by at least 6 mm in diameter, by at least 7 mm in diameter, by at least 8 mm in diameter, by at least 9 mm in diameter, by at least 10 mm in diameter, by at least 11 mm in diameter, by at least 12 mm in diameter, by a least 13 mm in diameter, by at least 14 mm in diameter, by at least 15 mm in diameter, by at least 20 mm in diameter, by at least 25 mm in diameter, by at least 30 mm in diameter, by at least 40 mm in diameter, by at least 50 mm in diameter or more. In some cases, the subject has had the bulk of the tumor resected.

The subject is preferably a mammal in need of such treatment, e.g., a subject that has been diagnosed with cancer or a viral infection, or a predisposition thereto, i.e., at risk of developing cancer or a viral infection. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Modes of administration include intravenous, systemic, oral, rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule. Parenteral modalities (subcutaneous or intravenous) may be preferable for more acute illness, or for therapy in patients that are unable to tolerate enteral administration due to gastrointestinal intolerance, ileus, or other concomitants of critical illness. Inhaled therapy is also provided.

For example, the composition is administered in a form selected from the group consisting of pills, capsules, tablets, granules, powders, salts, crystals, liquids, serums, syrups, suspensions, gels, creams, pastes, films, patches, and vapors.

In some cases, the methods described herein are used in conjunction with one or more agents or a combination of additional agents, e.g., an anti-cancer agent. Suitable agents include current pharmaceutical and/or surgical therapies for an intended application, such as, for example, cancer. For example, the methods described herein can be used in conjunction with one or more chemotherapeutic or anti-neoplastic agents, e.g., chemotherapy, targeted cancer therapy, cancer vaccine therapy, or immunotherapy. In some cases, the additional chemotherapeutic agent is radiotherapy. In some cases, the chemotherapeutic agent is a cell death-inducing agent. Treatment with immunotherapeutic methods or compositions described herein may be a stand-alone treatment, or may be one component or phase of a combination therapy regime, in which one or more additional therapeutic agents are also used to treat the patient.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

The term "antineoplastic agent" is used herein to refer to agents that have the functional property of inhibiting a development or progression of a neoplasm in a human, particularly a malignant (cancerous) lesion. Inhibition of metastasis is frequently a property of antineoplastic agents.

By "agent" is meant any small molecule chemical compound, antibody, nucleic acid molecule, or polypeptide, or fragments thereof.

By "binding to" a molecule is meant having a physicochemical affinity for that molecule.

By "control" or "reference" is meant a standard of comparison. As used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, β-galactosidase or luciferase). Depending on the method used for detection, the amount and measurement of the change can vary. Determination of statistical significance is within the ability of those skilled in the art, e.g., the number of standard deviations from the mean that constitute a positive result.

As used herein, "detecting" and "detection" are understood that an assay performed for identification of a specific analyte in a sample, e.g., an antigen in a sample or the level of an antigen in a sample. The amount of analyte or activity detected in the sample can be none or below the level of detection of the assay or method.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "polynucleotide" or "nucleic acid" as used herein designates mRNA, RNA, CRNA, cDNA or DNA. As used herein, a "nucleic acid encoding a polypeptide" is understood as any possible nucleic acid that upon (transcription and) translation would result in a polypeptide of the desired sequence. The degeneracy of the nucleic acid code is well understood. Further, it is well known that various organisms have preferred codon usage, etc. Determination of a nucleic acid sequence to encode any polypeptide is well within the ability of those of skill in the art.

As used herein, "isolated" or "purified" when used in reference to a polypeptide means that a polypeptide or protein has been removed from its normal physiological environment (e.g., protein isolated from plasma or tissue, optionally bound to another protein) or is synthesized in a non-natural environment (e.g., artificially synthesized in an in vitro translation system or using chemical synthesis). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition. An isolated virus or viral vector is a virus that is removed from the cells, typically in culture, in which the virus was produced.

By "isolated nucleic acid" is meant a nucleic acid that is free of the genes which flank it in the naturally-occurring genome of the organism from which the nucleic acid is derived. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a synthetic cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones. For example, the isolated nucleic acid is a purified cDNA or RNA polynucleotide. Isolated nucleic acid molecules also include messenger ribonucleic acid (mRNA) molecules.

As used herein, "kits" are understood to contain at least one non-standard laboratory reagent for use in the methods of the invention in appropriate packaging, optionally containing instructions for use. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the a and g chains and four $C_H$ domains for m and e isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa (k) and lambda (l), based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha (a), delta (d), epsilon (e), gamma (g) and mu (m), respectively. The g and a classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a b-sheet configuration, connected by three hypervariable regions, which form loops connecting, and in some cases forming part of, the b-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system;

Lefranc, M. P. et al. Nucl. Acids Res. 27:209-212 (1999), Ruiz, M. e al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

Monoclonal antibodies include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). Also provided are variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332: 323-329 (1988); and Presta, Curr. Op. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-327 (1988); Verhoeyen et al., Science, 239:1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a $C_L$ and at least heavy chain constant domains, $C_H$ 1, $C_H$ 2 and $C_H$ 3. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', $F(ab')_2$, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

The phrase "functional fragment or analog" of an antibody is a compound having qualitative biological activity in common with a full-length antibody. For example, a functional fragment or analog of an anti-IgE antibody is one that can bind to an IgE immunoglobulin in such a manner so as to prevent or substantially reduce the ability of such molecule from having the ability to bind to the high affinity receptor, $Fc_eRI$.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H$ 1). Each Fab fragment is monovalent with respect to antigen binding, i.e., it has a single antigen-binding site. Pepsin treatment of an antibody yields a single large $F(ab')_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "cross-over" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA, 90:6444-6448 (1993).

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. For example, a fragment may contain 10, 20, 30, 40, 50, 60, 70, 80, 90, or 100, 200, 300, 400, 500, 600, 700, 800, 900, or 1000 nucleotides or amino acids. However, the invention also comprises polypeptides and nucleic acid fragments, so long as they exhibit the desired biological activity of the full length polypeptides and nucleic acid, respectively. A nucleic acid fragment of almost any length is employed. For example, illustrative polynucleotide segments with total lengths of about 10,000, about 5000, about 3000, about 2,000, about 1,000, about 500, about 200, about 100, about 50 base pairs in length (including all intermediate lengths) are included in many implementations of this invention. Similarly, a polypeptide fragment of almost any length is employed. For example, illustrative polypeptide segments with total lengths of about 10,000, about 5,000, about 3,000, about 2,000, about 1,000, about 5,000, about 1,000, about 500, about 200, about 100, or about 50 amino acids in length (including all intermediate lengths) are included in many implementations of this invention.

As used herein, an antibody that "internalizes" is one that is taken up by (i.e., enters) the cell upon binding to an antigen on a mammalian cell (e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

As used herein, an antibody is said to be "immunospecific," "specific for" or to "specifically bind" an antigen if it reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and in certain embodiments, HuM2e antibody specifically binds to M2e if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M. Affinities of antibodies can be readily determined using conventional techniques, for example, those described by Scatchard et al. (Ann. N.Y. Acad. Sci. USA 51:660 (1949)).

Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcgRIII only, whereas monocytes express FcgRI, FcgRII and FcgRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., PNAS (USA) 95:652-656 (1998).

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100.mu·g/ml denatured salmon sperm DNA (ssDNA). In a most preferred embodiment, hybridization will occur at 42° C. C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42.degree. C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

"Obtaining" is understood herein as manufacturing, purchasing, or otherwise coming into possession of.

As used herein, "operably linked" is understood as joined, preferably by a covalent linkage, e.g., joining an amino-terminus of one peptide, e.g., expressing an enzyme, to a carboxy terminus of another peptide, e.g., expressing a signal sequence to target the protein to a specific cellular compartment; joining a promoter sequence with a protein coding sequence, in a manner that the two or more components that are operably linked either retain their original activity, or gain an activity upon joining such that the activity of the operably linked portions can be assayed and have detectable activity, e.g., enzymatic activity, protein expression activity.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservative's and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, $\alpha$-tocopherol, and the like; and metal chelating agents, such as citric acid, ethylenediamine tetraacetic acid (EDTA), sorbitol, tartaric acid, phosphoric acid, and the like.

In some cases, a composition of the invention is administered orally or systemically. Other modes of administration include rectal, topical, intraocular, buccal, intravaginal, intracisternal, intracerebroventricular, intratracheal, nasal, transdermal, buccal, sublingual within/on implants, or parenteral routes. The term "parenteral" includes subcutaneous, intrathecal, intravenous, intramuscular, intraperitoneal, intracardiac, intracranial, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule. Parenteral modalities (subcutaneous or intravenous) may be preferable for more acute illness, or for therapy in patients that are unable to tolerate enteral administration due to gastrointestinal intolerance, ileus, or other concomitants of critical illness. Inhaled therapy may be most appropriate for pulmonary vascular diseases (e.g., pulmonary hypertension).

As used herein, the terms "prevent," "preventing," "prevention," "prophylactic treatment" and the like refer to reducing the probability of developing a disorder or condition in a subject, who does not have, but is at risk of or susceptible to developing a disorder or condition.

As used herein, "plurality" is understood to mean more than one. For example, a plurality refers to at least two, three, four, five, or more.

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments). Optionally the peptide further includes one or more modifications such as modified peptide bonds, i.e., peptide isosteres, and may contain amino acids other than the 20 gene-encoded amino acids. The polypeptides may be modified by either natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formulation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins, Structure and Molecular Properties, 2nd ed., T. E. Creighton, W.H. Freeman and Company, New York (1993); Posttranslational Covalent Modification of Proteins, B. C. Johnson, ed., Academic Press, New York, pgs. 1-12 (1983); Seifter et al., Meth. Enzymol 182:626-646 (1990); Rattan et al., Ann. N.Y. Acad. Sci. 663:48-62 (1992)).

A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

The term "reduce" or "increase" is meant to alter negatively or positively, respectively, by at least 5%. An alteration may be by 5%, 10%, 25%, 30%, 50%, 75%, or even by 100%.

A "sample" as used herein refers to a biological material that is isolated from its environment (e.g., blood or tissue from an animal, cells, or conditioned media from tissue culture) and is suspected of containing, or known to contain an analyte, such as a protein. A sample can be blood or tumor-infiltrating lymphocytes from a subject. A sample can also be a partially purified fraction of a tissue or bodily fluid. A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

A "subject" as used herein refers to an organism. In certain embodiments, the organism is an animal. In certain embodiments, the subject is a living organism. In certain embodiments, the subject is a cadaver organism. In certain preferred embodiments, the subject is a mammal, including, but not limited to, a human or non-human mammal. In certain embodiments, the subject is a domesticated mammal or a primate including a non-human primate. Examples of subjects include humans, monkeys, dogs, cats, mice, rats, cows, horses, goats, and sheep. A human subject may also be referred to as a patient.

A "subject sample" or "test sample" can be a sample obtained from any subject, typically a blood, serum sample, or tumor-infiltrating lymphocytes; however the method contemplates the use of any body fluid or tissue from a subject. The sample may be obtained, for example, for diagnosis of a specific individual for the presence or absence of a particular disease or condition.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions associated with cancer is within the ability of those in the art. Subjects suffering from, and suspected of suffering from, a specific disease, condition, or syndrome are not necessarily two distinct groups.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Ranges provided herein are understood to be shorthand for all of the values within the range.

By "reduces" is meant a negative alteration of at least 5%, 10%, 25%, 50%, 75%, or 100%.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

By "tumor microenvironment" is meant the cellular environment in which a tumor exists, including surrounding blood vessels, immune cells, fibroblasts, bone marrow-derived inflammatory cells, lymphocytes, signaling molecules and the extracellular matrix. The tumor and the surrounding microenvironment are closely related and interact constantly.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Unless specifically stated or obvious from context, as used herein, the term "or" is understood to be inclusive. Unless specifically stated or obvious from context, as used herein, the terms "a", "an", and "the" are understood to be singular or plural.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

DETAILED DESCRIPTION

Figure 1:
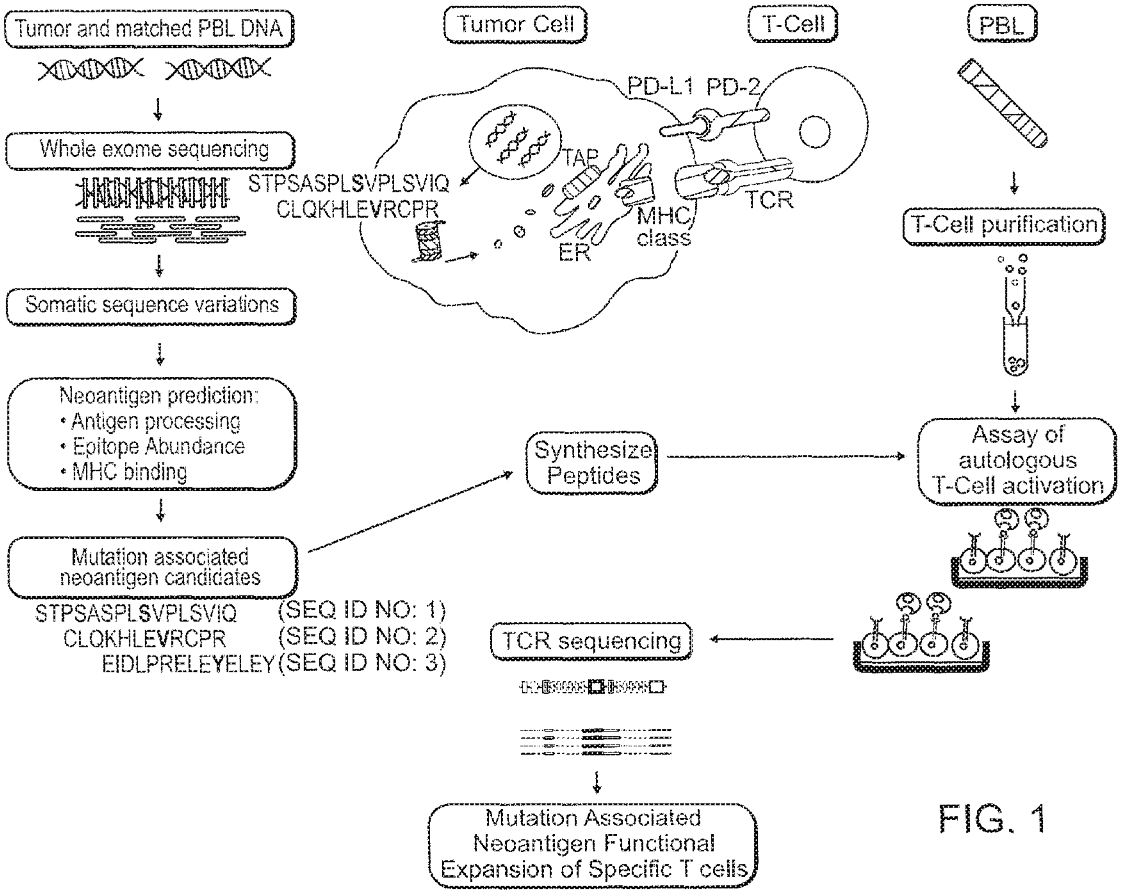
FIG. 1 is a schematic showing an overview of MANAFEST assay development. Exome data are applied in the neoantigen prediction pipeline to generate candidate MANAs. Putative neoantigens are used to generate peptides and stimulate autologous T cells, followed by TCR next-generation sequencing. Intra-tumoral neoantigen-specific TCR expansion is subsequently evaluated. The peptides shown in FIG. 1 have been assigned SEQ ID NOs: 1, 2, and 3, sequentially.

The invention is based, at least in part, on the surprising identification of a sensitive, specific, scalable, and simple method to identify functional anti-tumor T cell responses, i.e., mutation associated neoantigens (MANA) functional expansion of specific T cells (MANAFEST), virus antigen functional expansion of specific T cells (VIRAFEST), and tumor-associated antigen (TAAFEST). The invention integrates a relatively short in vitro T cell stimulation with candidate tumor-specific peptides or transfected minigenes with TCRseq to monitor peptide-specific responses with clonal expansion (as assayed by TCRseq) rather than by cytokine production or proliferation. The methods described herein demonstrate superior sensitivity over the conventional method of enzyme-linked immunospot (ELISPOT).

Tumor cells contain nonsynonymous somatic mutations that alter the amino acid sequences of the proteins encoded by the affected genes. Those alterations are foreign to the immune system and may therefore represent tumor-specific neoantigens capable of inducing anti-tumor immune responses. Somatic mutational and neoantigen density has recently been shown to correlate with long-term benefit from immune checkpoint blockade in non-small cell lung cancer and melanoma suggesting that a high density of neoepitopes stemming from somatic mutations may enhance clinical benefit from blockade of immune checkpoints that unleash endogenous responses to these mutation-associated neoantigens (MANAs).

However, prior to the invention described herein, in most cases, the specific neoantigens that are responsible for tumor-specific immune responses were not known and computational methods for predicting neoantigens were limited. Described herein is a method that sensitively and specifically evaluates candidate tumor neoantigens for their ability to induce T cell responses. This method is broadly useful for functional evaluation of neoantigens in research and clinical settings, including for biomarker prediction in checkpoint blockade therapy and for identification of functional MANAs for personalized immunotherapy approaches.

With the emergence of immunotherapy as a major clinical treatment for cancer, it has become clear that T cells are the primary cells that provide specific recognition of the cancer and mediate both direct killing and orchestrate innate antitumor responses. Given the number of mutations carried by tumors, it is clear that mutation associated neoantigens (MANA) are a major source of tumor antigenicity that allows T cells to distinguish them from normal cells. Additional antigenicity can come from viral antigens in tumors that are caused by virus infection and contain integrated viruses with oncogenes driving the cancer (ie HPV in cervical and head and neck cancer). Tumor associated antigens—self antigens upregulated in tumors—may also be a source of antigenicity.

As described herein, guidance of precision immunotherapy requires assessment of tumor-specific T cell responses, most particularly in the blood. These biomarkers define which patients will respond to a given immunotherapy and who might require additional therapies. Additionally, approaches that use "personalized vaccines" consisting of MANA that are specific to an individual's tumor will require knowledge of the antigens that T cells are responsive against. Prior to the invention described herein, algorithms applied to MANA or viral genes for predicting T cell antigen recognition gave a general list of possibilities, but were highly imperfect. The common functional assay-ELISPOT-works well for viral infections, but is not sensitive enough to detect the weaker T cell responses against tumor antigens. Tetramer staining is cumbersome and thus cannot easily be applied to analyze all the antigens that tumor specific T cells could potentially recognize, nor does it determine functionality.

To address these issues, described herein is an assay system, termed MANAFEST (MANA Functional Expansion of Specific T cells). Related assays for viral antigens in virus-associated tumors and for tumor-associated antigens are termed VIRAFEST and TAAFEST. The assay begins by using prediction algorithms to identify and provide a broad list of candidate antigens and then tests the individual candidates as peptides, or as a minigene that encodes the peptide, for functional recognition. Instead of assaying cytokine production, which is done with the ELISPOT, MANAFEST (and VIRAFEST and TAAFEST) use TCRseq to analyze for expansion of T cell clones (with unique TCRbeta CDR3 sequences) specifically with only one of the peptides.

Accordingly, in certain embodiments, method of functionally evaluating a candidate antigen for the ability to induce a T cell response comprises obtaining a test sample of blood or tumor-infiltrating lymphocytes from a subject having or at risk of developing a cancer or a viral infection; stimulating expansion of autologous T cells from the subject with the candidate antigen, said candidate antigen comprising a peptide, a protein or a minigene transfected into autologous monocytic cells; isolating deoxyribonucleic acid (DNA) from the T cells; amplifying the T cell receptor-β (TCR-β) complementarity-determining region 3 (CDR3) DNA; determining a level of antigen-specific T cell expansion; comparing the level of antigen-specific T cell expansion to a level of expansion of T cells in the absence of the candidate peptide; determining that the candidate antigen has the ability to induce a T cell response if the level of antigen-specific T cell expansion is higher than the level of expansion of T cells in the absence of the candidate peptide.

In certain embodiments, the autologous T cells from the subject are stimulated to expand with the candidate antigen, said candidate antigen comprising a peptide or whole protein or with autologous peripheral blood mononuclear cells (PBMCs) which have been transfected with a tandem minigene construct encoding the candidate antigen(s). Antigen-specific T cell expansion can be determined, for example, by comparing TCR-Vβ clonality prior to stimulation with the candidate antigen or PBMCs to TCR-Vβ clonality after stimulation with the candidate antigen.

In certain embodiments, the candidate antigen comprises a tumor antigen or a viral antigen. In certain embodiments, the candidate antigen, in the form of a peptide, protein or minigene transfected into autologous monocytic cells, comprises a tumor mutation-associated neoantigen (MANA), a viral antigen, or a non-mutated tumor-associated antigen. In some embodiments, the viral antigen is expressed by an integrated cancer-associated virus or a non-oncogenic virus. The integrated cancer-associated virus comprises human papilloma virus (HPV) associated with cervical or head and neck cancer, Epstein Barr virus (EBV), Merkel Cell Polyomavirus, Hepatitis B virus (HBV) or Hepatitis C virus (HCV). In certain embodiments, the virus comprises human immunodeficiency virus (HIV).

In certain embodiments, the sample comprises a blood sample or a tumor infiltrating lymphocyte population.

In other embodiments, a method of determining whether a given immunotherapy will inhibit a tumor in a subject comprises functionally validating a candidate antigen for the ability to induce a T cell response as described herein, thereby determining that immunotherapy will inhibit the tumor if the candidate antigen has the ability to induce a T cell response, and that the given immunotherapy will inhibit the tumor and should be used to treat the patient. It is also determined whether immunotherapy will inhibit a tumor prior to or subsequent to administration of the immunotherapy to the subject.

In certain embodiments, the immunotherapy comprises administration of an immune checkpoint inhibitor alone or in combination with one or more additional anti-tumor treatments. The immune checkpoint inhibitor comprises an anti-cytotoxic T-lymphocyte-associated protein 4 (CTLA4) antibody, an anti-programmed cell death protein 1 (PD-1) antibody, an anti-programmed death-ligand 1 (PD-L1) antibody, an anti-lymphocyte-activation 3 (LAG3) antibody, an anti-T-cell immunoglobulin and mucin-domain containing-3 (TIM-3) antibody, an anti-T-cell immunoreceptor with Ig and immunoreceptor tyrosine-based inhibition motif (ITIM) domains (TIGIT) antibody, an anti-V domain-containing Ig suppressor of T-cell activation antibody, an anti-cluster of differentiation 47 (CD47) antibody, an anti-signal regulatory alpha (SIRP α) antibody, an anti-B7-H3 antibody, an anti-B7-H4 antibody, an anti-neuritin antibody, an anti-neuropilin antibody, or an anti-interleukin-35 (IL-35) antibody, or any combination thereof. In certain embodiments, the immune checkpoint inhibitor comprises a drug that inhibits indoleamine-pyrrole 2,3-dioxygenase (IDO), A2A adenosine receptor (A2AR), arginase, or glutaminase, or any combination thereof. In certain embodiments, the immunotherapy further comprises administering an agonist of a co-stimulatory receptor. The agonist comprises an anti-glucocorticoid-induced tumor necrosis factor receptor (TNFR)-related protein (GITR) antibody, an anti-CD27 antibody, an anti-4-1BB antibody, an anti-OX40 antibody, an anti-inducible T-cell co-stimulator (ICOS) antibody, or an anti-CD40 antibody, or any combination thereof.

In another embodiment, a method of determining whether a vaccine will inhibit a tumor or a virus in a subject comprises functionally evaluating a candidate antigen for the ability to induce a T cell response; determining that the vaccine will inhibit the tumor or virus, if the candidate antigen has the ability to induce a T cell response, wherein the vaccine incorporates comprises the candidate antigen, thereby determining whether the vaccine will inhibit the tumor or virus. In embodiments, the vaccine is administered to the subject. In certain embodiments, the vaccine comprises the candidate peptide or a tandem minigene or full gene encoding the candidate antigen incorporated into a recombinant viral or bacterial vaccine. In some embodiments, the candidate antigen comprises a tumor antigen or a viral antigen. In certain embodiments, the candidate antigen comprises a mutation-associated neoantigen (MANA) or a non-mutated tumor-associated antigen. In certain embodiments, the viral antigen is expressed by an integrated cancer-associated virus or a non-oncogenic virus.

T Cells

A T cell or T lymphocyte is a type of lymphocyte (a subtype of white blood cell) that plays a central role in cell-mediated immunity. T cells are distinguished from other lymphocytes, such as B cells and natural killer cells, by the presence of a T-cell receptor on the cell surface. T cells are so named because they mature in the thymus from thymocytes (although some also mature in the tonsils).

The several subsets of T cells each have a distinct function. There are many types of T cells including effector T cells, T helper cells, cytotoxic (killer) T cells, memory T cells, regulatory T cells, natural killer cells, gamma delta T cells, and mucosal associated invariant T cells. The majority of human T cells rearrange their alpha and beta chains on the cell receptor and are termed alpha beta T cells (αβ T cells) and are part of the adaptive immune system. Specialized gamma delta T cells, a small minority of T cells in the human body, more frequent in ruminants, have invariant T cell receptors with limited diversity that can effectively present antigens to other T cells and are considered to be part of the innate immune system.

A unique feature of T cells is their ability to discriminate between healthy and abnormal (e.g. infected or cancerous) cells in the body. Healthy cells typically express a large number of self derived peptide-loaded major histocompatibility complex (pMHC) on their cell surface and although the T cell antigen receptor can interact with at least a subset of these self pMHC, the T cell generally ignores these healthy cells. However, when these very same cells contain even minute quantities of pathogen derived pMHC, T cells are able to become activated and initiate immune responses. The ability of T cells to ignore healthy cells, but respond when these same cells contain pathogen (or cancer) derived pMHC is known as antigen discrimination.

T Cell Receptor

The T-cell receptor, or TCR, is a molecule found on the surface of T cells, or T lymphocytes, that is responsible for recognizing fragments of antigen as peptides bound to MHC molecules. The binding between TCR and antigen peptides is of relatively low affinity and is degenerate: that is, many TCRs recognize the same antigen peptide and many antigen peptides are recognized by the same TCR. The TCR is composed of two different protein chains (that is, it is a heterodimer). In humans, in 95% of T cells the TCR consists of an alpha (α) and beta (β) chain, whereas in 5% of T cells the TCR consists of gamma and delta (γ/δ) chains. This ratio changes during ontogeny and in diseased states as well as in different species.

When the TCR engages with antigenic peptide and MHC (peptide/MHC), the T lymphocyte is activated through signal transduction, that is, a series of biochemical events mediated by associated enzymes, co-receptors, specialized adaptor molecules, and activated or released transcription factors.

The TCR is a disulfide-linked membrane-anchored heterodimeric protein normally consisting of the highly variable alpha (α) and beta (β) chains expressed as part of a complex with the invariant CD3 chain molecules. T cells expressing this receptor are referred to as α:β (or αβ) T cells, though a minority of T cells express an alternate receptor, formed by variable gamma (γ) and delta (δ) chains, referred as γδ T cells. Each chain is composed of two extracellular domains: Variable (V) region and a Constant (C) region, both of Immunoglobulin superfamily (IgSF) domain forming antiparallel β-sheets. The constant region is proximal to the cell membrane, followed by a transmembrane region and a short cytoplasmic tail, while the Variable region binds to the peptide/MHC complex. The constant domain of the TCR domain consists of short connecting sequences in which a cysteine residue forms disulfide bonds, which forms a link between the two chains.

The variable domain of both the TCR α-chain and β-chain each have three hypervariable or complementarity determining regions (CDRs), whereas the variable region of the β-chain has an additional area of hypervariability (HV4) that does not normally contact antigen and, therefore, is not considered a CDR. The residues are located in two regions of the TCR, at the interface of the α- and β-chains and in the β-chain framework region that is thought to be in proximity to the CD3 signal-transduction complex. CDR3 is the main CDR responsible for recognizing processed antigen, although CDR1 of the alpha chain has also been shown to interact with the N-terminal part of the antigenic peptide, whereas CDR1 of the β-chain interacts with the C-terminal part of the peptide. CDR2 recognizes the MHC. CDR4 of the β-chain does not participate in antigen recognition, but has been shown to interact with superantigens.

Processes for the generation of TCR diversity are based mainly on genetic recombination of the DNA encoded segments in individual somatic T cells—either somatic V(D)J recombination using recombinant activating gene 1 (RAG1) and RAG2 recombinases or gene conversion using cytidine deaminases (AID). Each recombined TCR possess unique antigen specificity, determined by the structure of the antigen-binding site formed by the α and β chains in case of αβ T cells or γ and δ chains on case of γδ T cells. The TCR alpha chain is generated by VJ recombination, whereas the beta chain is generated by VDJ recombination (both involving a somewhat random joining of gene segments to generate the complete TCR chain). Likewise, generation of the TCR gamma chain involves VJ recombination, whereas generation of the TCR delta chain occurs by VDJ recombination. The intersection of these specific regions (V and J for the alpha or gamma chain; V, D, and J for the beta or delta chain) corresponds to the CDR3 region that is important for peptide/MHC recognition.

TCRseq

The recent development of single-cell RNA sequencing (scRNAseq) allows the transcriptomes of thousands of cells to be processed simultaneously, bringing a way to identify subpopulations of cells and provide functional insights such as the identification of each cell's unique TCRs and paired alpha and beta heterodimers that were previously masked in the analysis of an ensemble of multiple cells. However, scRNAseq is not devoid of biases and noise. For example, scRNAseq can only quantify the expression of most highly expressed genes and likely suffers from PCR amplification biases.

Many PCR-based methods for the amplification of V(D)J segments either use primer sets that introduce amplification artifacts owing to the differential amplification of some DNA templates over others, requiring the usage of complex normalization methods or require complex protocols based on template-switching effect of reverse transcriptase for the unbiased preparation of TCR cDNA libraries.

The single-cell sequencing model for TCRs described recently (Redmond et al., 2016 Genome Medicine, 8:80, incorporated herein by reference) avoids these issues and recovers these complex repertoires alongside the rest of the transcriptome present in T-cells.

Redmon addresses the accurate characterization of T-cell repertoires from scRNAseq data. A computational method "single-cell TCRseq" (scTCRseq) was generated to identify and count RNA reads mapping to specific TCR V and C region genes. scTCRseq facilitates the identification of productive and paired alpha and beta chain V(D)J TCR rearrangements and enables the recovery of full TCR including the nucleotide insertions and deletions at junctions in single T-cells. As described by Redmon, single-cell TCRseq provides an avenue for phenotypic investigation of T-cells in conjunction with the accompanying whole-transcriptome data.

ELISPOT

The Enzyme-Linked ImmunoSpot (ELISPOT) assay is a widely used method for monitoring cellular immune responses in humans and other animals, and has found clinical applications in the diagnosis of tuberculosis and the monitoring of graft tolerance or rejection in transplant patients (Czerkinsky et al., J Immunol Methods, 65 (1-2): 109-121, incorporated herein by reference). Prior to the invention described herein, the ELISPOT technique was among the most useful means available for monitoring cell-mediated immunity, due to its sensitive and accurate detection of rare antigen-specific T cells (or B cells) and its ability to visualize single positive cells within a population of peripheral blood mononuclear cells (PBMCs). The ELISPOT assay is also used for the identification and enumeration of cytokine-producing cells at the single cell level, but is still used for detection of antigen-specific antibody-secreting cells (ASC).

At appropriate conditions, the ELISPOT assay allows visualization of the secretory product(s) of individual activated or responding cells. Each spot that develops in the assay represents a single reactive cell. Thus, the ELISPOT assay provides both qualitative (regarding the specific cytokine or other secreted immune molecule) and quantitative (the frequency of responding cells within the test population) information.

The ELISPOT assays employ a technique very similar to the sandwich enzyme-linked immunosorbent assay (ELISA) technique. In an ELISPOT assay, the membrane surfaces in a 96-well polyvinylidene fluoride (PVDF)-membrane microtiter plate are coated with capture antibody that binds a specific epitope of the cytokine being assayed. During the cell incubation and stimulation step, cells, e.g., peripheral blood mononuclear cells (PBMCs), are seeded into the wells of the plate along with the antigen, and form a monolayer on the membrane surface of the well. As the antigen-specific cells are activated, they release the cytokine, which is captured directly on the membrane surface by the immobilized antibody. The cytokine is thus "captured" in the area directly surrounding the secreting cell, before it has a chance to diffuse into the culture media, or to be degraded by proteases and bound by receptors on bystander cells. Subsequent detection steps visualize the immobilized cytokine as an ImmunoSpot; essentially the secretory footprint of the activated cell.

As described herein, ELISPOT works well for vial infections, but is not sensitive enough to detect the weaker T cell responses against tumor antigens.

Immune Checkpoint Inhibitors

Immune checkpoint inhibitors block certain proteins made by some types of immune system cells, such as T cells, and some cancer cells. These proteins help keep immune responses in check; however, they can also keep T cells from killing cancer cells. When these proteins are blocked, the "brakes" on the immune system are released and T cells are able to kill cancer cells more effectively. Examples of checkpoint proteins found on T cells or cancer cells include PD-1/PD-L1 and CTLA-4/B7-1/B7-2.

Pharmaceutical Therapeutics

The invention provides pharmaceutical compositions for use as a therapeutic. In one aspect, the composition is administered systemically, for example, formulated in a pharmaceutically-acceptable buffer such as physiological saline. Preferable routes of administration include, for example, instillation into the bladder, subcutaneous, intravenous, intraperitoneal, intramuscular, or intradermal injections that provide continuous, sustained levels of the composition in the patient. Treatment of human patients or other animals is carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia or infection, although in certain instances lower amounts will be needed because of the increased specificity of the compound. A compound is administered at a dosage that enhances an immune response of a subject, or that reduces the proliferation, survival, or invasiveness of a neoplastic cell as determined by a method known to one skilled in the art.

Formulation of Pharmaceutical Compositions

The administration of compositions for the treatment of cancer may be by any suitable means that results in a concentration of the therapeutic that, combined with other components, is effective in ameliorating, reducing, or stabilizing cancer. The composition may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, intravesicularly or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of compound used in mice or nonhuman primates, as a skilled artisan recognizes it is routine in the art to modify the dosage for humans compared to animal models. In certain embodiments it is envisioned that the dosage may vary from between about 0.1 μg compound/kg body weight to about 5000 μg compound/kg body weight; or from about 1 μg/kg body weight to about 4000 μg/kg body weight or from about 10 μg/kg body weight to about 3000 μg/kg body weight. In other embodiments this dose may be about 0.1, 0.3, 0.5, 1, 3, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 μg/kg body weight. In other embodiments, it is envisaged that doses may be in the range of about 0.5 μg compound/kg body weight to about 20 μg compound/kg body weight. In other embodiments the doses may be about 0.5, 1, 3, 6, 10, or 20 mg/kg body weight. Of course, this dosage amount may be adjusted upward or downward, as is routinely done in such treatment protocols, depending on the results of the initial clinical trials and the needs of a particular patient.

Pharmaceutical compositions are formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Kits

The invention provides kits for the treatment or prevention of a cancer. In one embodiment, the kit includes a therapeutic or prophylactic composition containing an effective amount of an agent described herein. In some embodiments, the kit comprises a sterile container that contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired an agent of the invention is provided together with instructions for administering the agent to a subject having or at risk of developing a cancer. The instructions will generally include information about the use of the composition for the treatment or prevention of a cancer. In other embodiments, the instructions include at least one of the following: description of the therapeutic agent; dosage schedule and administration for treatment or prevention of a cancer or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1: Functional Analysis of Candidate Neoantigens

With the growth of cancer immunotherapy dependent on enhancing anti-tumor T cell responses, it has become important to rapidly, sensitively and specifically assess functional anti-tumor T cell responses, mostly in the blood. Described herein is a methodology to accomplish this.

In lieu of the traditional ELISpot assay, which lacks sensitivity and only assesses cytokine production, described herein is a sensitive approach for assessing T cell response to candidate tumor antigens that utilizes next-generation sequencing of TCR-Vβ CDR3 regions as a measure of antigen-specific T cell expansion. This technique, termed MANA functional expansion of specific T-cells (MANAFEST), has been applied to the functional analysis of T cell responses to MANAs, but can also be applied to responses against viral antigens, including those expressed in virus-induced cancers such as HPV-associated cervical and head-and-neck cancer (termed VIRAFEST), and non-mutated tumor-associated antigens, such as cancer-testes antigens or mesothelin (termed TAAFEST). In the case of MANA detection, whole exome sequencing data from tumor and matched normal samples are applied in a neoantigen prediction pipeline that evaluates antigen processing, MHC binding and gene expression to generate MANAs specific to the patient's HLA haplotype.

Peptides representing known and/or candidate MANAs based on in silico predictions are used to stimulate autologous T cells in a 10-day culture system (FIG. 1). DNA from cultured T cells is subsequently isolated and T cell receptor-β (TCR-β) CDR3 regions are amplified in a multiplex PCR method using 45 forward primers specific to TCR-Vβ gene segments and 13 reverse primers specific to TCR JB gene segments (Adaptive Biotechnologies). Synthesized tandem minigene constructs transfected into peripheral blood monocytes could be used in place of peptides for the T cell stimulation component of these assays.

In the MANAFEST approach, TCR-Vβ clonality is compared pre-stimulation to post-stimulation in vitro with MANA peptides and the expansion of MANA-stimulated cultures is compared to the expansion observed in T cell cultures without peptide and/or uncultured T cells. A differential expansion TCR analysis is performed, where productive frequencies in the peptide stimulated T cells are compared to unstimulated T cells and/or uncultured T cells by Fisher's exact test. The p-values are corrected for multiple hypothesis testing using the Benjamini-Hochberg procedure (FIG. 2).

Figure 2:
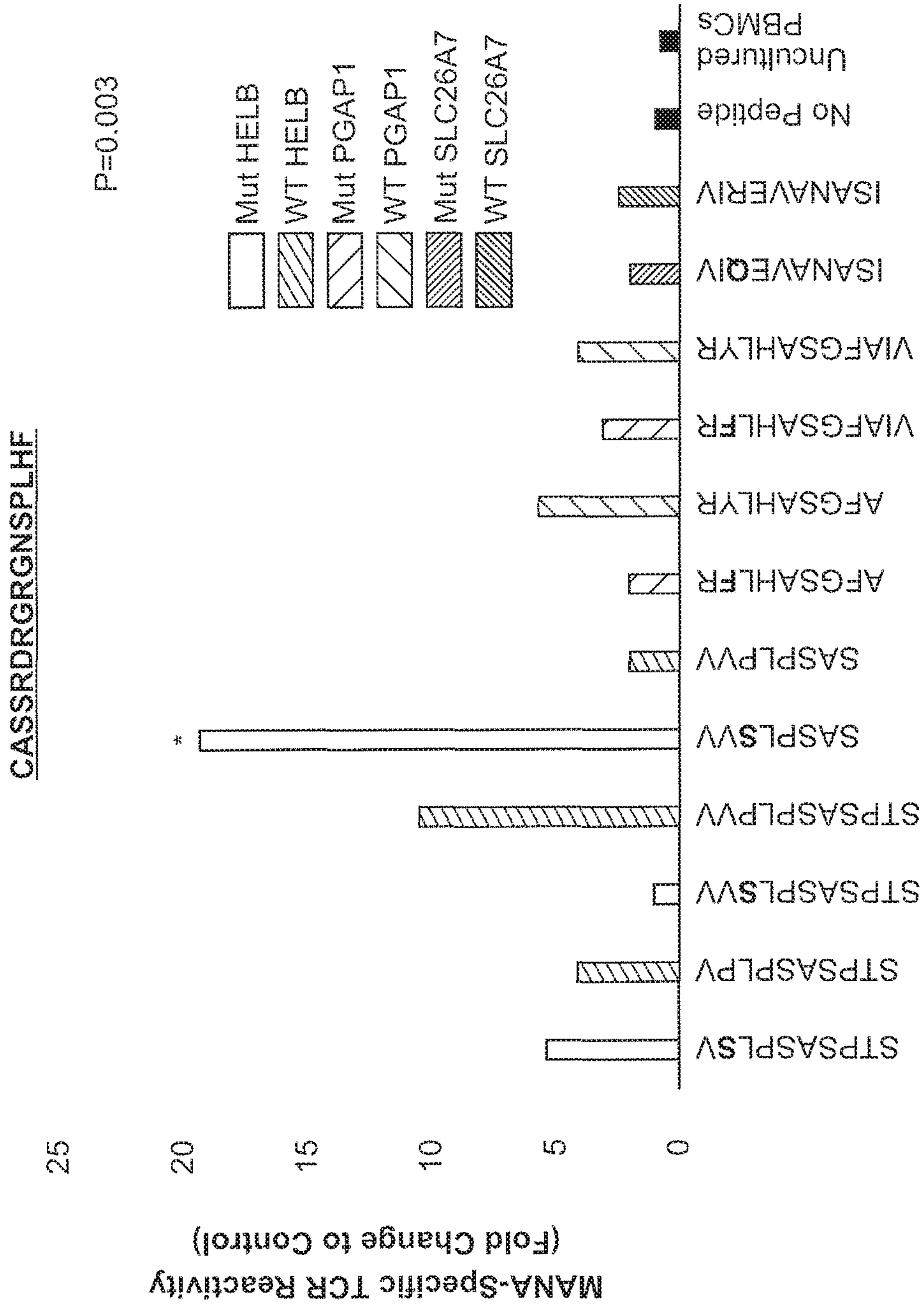
FIG. 2 is a bar chart showing the results of neoantigen-specific TCR expansion in stimulated T cell cultures. Peptides generated from neoantigen candidates were synthesized and used to pulse autologous peripheral T cells. Reactive TCR clones were matched to clones found in tumor-infiltrating lymphocytes (TILs). Neoantigen-specific TCR reactivity (CDR3: CASSRDRGRGNSPLHF (SEQ ID NO: 4)) was observed for the mutant peptides associated with mutant HELB. Adjusted p value is given for pairwise comparisons between productive frequencies in peptide stimulated versus unstimulated T cells. Solid bars represent mutant and shaded bars denote wild type peptides. The peptides shown in FIG. 2 have been assigned SEQ ID NOs: 5-16, sequentially.

FIG. 2 shows neoantigen-specific TCR expansion in stimulated T cell cultures. Peptides generated from neoantigen candidates were synthesized and used to pulse autologous peripheral T cells. Reactive TCR clones were matched to clones found in tumor-infiltrating lymphocytes (TILs). Neoantigen-specific TCR reactivity (CDR3: CASSRDRGRGNSPLHF (SEQ ID NO: 4)) was observed for the mutant peptides associated with mutant helicase (DNA) B (HELB). Adjusted p value is given for pairwise comparisons between productive frequencies in peptide stimulated versus unstimulated T cells. Solid bars represent mutant and shaded bars denote wild type peptides.

The combination of the MANA stimulated T cell cultures and TCR-CDR3 sequencing followed by differential expansion analysis together compose the MANA functional expansion of specific T-cells (MANAFEST) assay. Identical analyses are used for VIRAFEST and TAAFEST, except the neoantigen prediction algorithms are applied to the relevant virus, viral antigens expressed by the virus-associated tumor, or to the shared genes up-regulated in the cancer.

The strategy is based on previous findings that antigen-specific T cells undergo rapid expansion upon stimulation by a cognate peptide-major histocompatibility complex (MHC) complex. Most importantly, as described in detail herein, this expansion may occur in the absence of detectable cytokine production and antigen recognition would therefore not be detected by conventional approaches, e.g., ELISPOT. In addition to being more sensitive than the conventional enzyme linked immunospot assay, the MANAFEST approach described herein allows us to match cMANA expanded TCR-Vβ CDR3s with those found in the patients' tumors themselves, identified by TCR-Vβ CDR3 deep sequencing from the same DNA used for mutational analysis. Thus, this approach can evaluate MANA-specific responses by T cells known to be present within the tumor microenvironment.

Also provided is the optimization of culture conditions to use a smaller number of cells, as well as optimization of biostatistical and bioinformatics analysis of TCRseq.

Example 2: Detection and Monitoring of Anti-MANA T Cell Repertoire

A set of sensitive and specific functional expansion of specific T cells (FEST) assays were developed herein to experimentally and bioinformatically evaluate antigen-specific clonal expansion using next generation TCR Vb CDR3 sequencing of T cells cultured with peptides representing candidate viral antigens (ViraFEST), TAAs (TAAFEST), or MANAs (MANAFEST). The FEST assays utilize this TCR quantification to identify antigen-specific T cell clonotypes based on clonal expansion after short-term stimulation and not only operate independently of cytokine production, but have enhanced sensitivity, specificity, and throughput capacity compared to other methods. The FEST platform works with all HLA haplotypes, and allows for tracking of antigen-specific T cells in FFPE and/or frozen tissue based on the ability of CDR3 regions to be used as a barcode for clones whose specificity is defined in the FEST assay.

This example shows that the MANAFEST assay, supported by a web-based biostatistical analytic platform, identifies MANA-specific TCR Vβ clones that can be matched with clones detected in tumor tissue and in the blood of cancer patients treated with checkpoint blockade. MANAFEST can therefore validate the tumor specificity of TCR Vβ clonotypes, interrogate the dynamics of the antigen-specific T cell response over time, and monitor the efficacy of checkpoint blockade using a simple liquid biopsy. Most importantly, the FEST assays can detect low frequency antigen-specific T cells in cases where other methods cannot.

Methods

Healthy donors and patients: All healthy donors and patients described in this study provided informed consent as approved by the IRB of Johns Hopkins University. The patient described in this study was treated at the Sidney Kimmel Comprehensive Cancer Center.

Non-small cell lung cancer (NSCLC) patient: Patient JH124 was diagnosed with Stage IIB squamous non-small cell lung cancer in November 2015 and enrolled on JHU IRB protocol NA_00092076. He received 2 doses of anti-PD-1 immunotherapy and underwent surgical resection in December 2015. Pathology demonstrated a complete pathologic response in the 9 cm primary tumor and N1 nodes positive for tumor, final pathology stage was IIA. The patient received adjuvant platinum-based chemotherapy from February 2016 to May 2016. He had no evidence of recurrence of his cancer at last follow up in September 2017.

Whole exome sequencing and putative MANA identification: Whole exome sequencing and identification of candidate neoantigens was performed as previously described using the VariantDx and ImmunoSelect-R pipelines (Personal Genome Diagnostics, Baltimore, MD) (Anagnostou, V. et al. *Cancer Discov* 7, 264-276, doi:10.1158/2159-8290.CD-16-0828 (2017)).

Whole exome sequencing was performed on pre-treatment tumor and matched normal samples. The tumor sample underwent pathological review for confirmation of lung cancer diagnosis and assessment of tumor purity. Slides from the FFPE block were macrodissected to remove contaminating normal tissue and peripheral blood was used as matched normal. DNA was extracted from tumor and matched peripheral blood using the Qiagen DNA FFPE and Qiagen DNA blood mini kit respectively (Qiagen, CA). Fragmented genomic DNA from tumor and normal samples was used for Illumina TruSeq library construction (Illumina, San Diego, CA) and exonic regions were captured in solution using the Agilent SureSelect v.4 kit (Agilent, Santa Clara, CA) according to the manufacturers' instructions as previously described (Sausen, M. et al. *Nature genetics* 45, 12-17, doi:10.1038/ng.2493 (2013); Jones, S. et al. *Science translational medicine* 7, 283ra253, doi:10.1126/scitranslmed.aaa7161 (2015); Bertotti, A. et al. *Nature* 526, 263-267, doi:10.1038/nature14969 (2015); Anagnostou, V. et al. *Cancer Discov* 7, 264-276, doi:10.1158/2159-8290.CD-16-0828 (2017)). Paired-end sequencing, resulting in 100 bases from each end of the fragments for the exome libraries was performed using Illumina HiSeq 2000/2500 instrumentation (Illumina, San Diego, CA). Depth of coverage was 209× and 80× for the tumor and matched normal respectively.

Primary processing of next-generation sequencing data and identification of putative somatic mutations: Somatic mutations were identified using the VariantDx custom software for identifying mutations in matched tumor and normal samples as previously described (Jones, S. et al. (2015)). In brief, prior to mutation calling, primary processing of sequence data for both the tumor and normal sample was performed using Illumina CASAVA software (version 1.8), including masking of adapter sequences. Sequence reads were aligned against the human reference genome (version hg19) using ELAND with additional realignment of select regions using the Needleman-Wunsch method (Needleman, S. B. & Wunsch, C. D. A general method applicable to the search for similarities in the amino acid sequence of two proteins. *J Mol Biol* 48, 443-453 (1970)). Candidate somatic mutations, consisting of point mutations, insertions and deletions were then identified using VariantDx across the whole exome. VariantDx examines sequence alignments of tumor samples against a matched normal while applying filters to exclude alignment and sequencing artifacts. In brief, an alignment filter was applied to exclude quality failed reads, unpaired reads, and poorly mapped reads in the tumor. A base quality filter was applied to limit inclusion of bases with reported Phred quality score >30 for the tumor and >20 for the normal. A mutation in the pre or post treatment tumor samples was identified as a candidate somatic mutation only when (1) distinct paired reads contained the mutation in the tumor; (2) the fraction of distinct paired reads containing a particular mutation in the tumor was at least 10% of the total distinct read pairs and (3) the mismatched base was not present in >1% of the reads in the matched normal sample as well as not present in a custom database of common germline variants derived from dbSNP and (4) the position was covered in both the tumor and normal. Mutations arising from misplaced genome alignments, including paralogous sequences, were identified and excluded by searching the reference genome.

Candidate somatic mutations were further filtered based on gene annotation to identify those occurring in protein coding regions. Functional consequences were predicted using snpEff and a custom database of CCDS, RefSeq and Ensembl annotations using the latest transcript versions available on hg19 from UCSC (https://genome.ucsc.edu/). Predictions were ordered to prefer transcripts with canonical start and stop codons and CCDS or RefSeq transcripts over Ensembl when available. Finally, mutations were filtered to exclude intronic and silent changes, while retaining mutations resulting in missense mutations, nonsense mutations, frameshifts, or splice site alterations. A manual visual inspection step was used to further remove artefactual changes.

Neoantigen Predictions: To assess the immunogenicity of somatic mutations, exome data combined with the patient's MHC class I haplotype, were applied in a neoantigen prediction platform that evaluates binding of somatic peptides to class I MHC, antigen processing, self-similarity and gene expression. Detected somatic mutations, consisting of nonsynonymous single base substitutions, insertions and deletions, were evaluated for putative neoantigens using the ImmunoSelect-R pipeline (Personal Genome Diagnostics, Baltimore, MD). To accurately infer the germline HLA 4-digit allele genotype, whole-exome-sequencing data from paired tumor/normal samples were first aligned to a reference allele set, which was then formulated as an integer linear programming optimization procedure to generate a final genotype (Szolek, A. et al. *Bioinformatics* 30, 3310-3316, doi:10.1093/bioinformatics/btu548 (2014)). The HLA genotype served as input to netMHCpan to predict the MHC class I binding potential of each somatic and wild-type peptide ($IC_{50}$ nM), with each peptide classified as a strong binder (SB), weak binder (WB) or non-binder (NB) (Nielsen, M. & Andreatta, M. *Genome Med* 8, 33, doi:10.1186/s13073-016-0288-x (2016); Lundegaard, C. et al. *Nucleic Acids Res* 36, W509-512, doi:10.1093/nar/gkn202 (2008); Lundegaard, C., Lund, O. & Nielsen, M. *Bioinformatics* 24, 1397-1398, doi:10.1093/bioinformatics/btn128 (2008)). Peptides were further evaluated for antigen processing by netCTLpan (Stranzl, T., et al. *Immunogenetics* 62, 357-368, doi:10.1007/s00251-010-0441-4 (2010)). and were classified as cytotoxic T lymphocyte epitopes (E) or non-epitopes (NA). Paired somatic and wild-type peptides were assessed for self-similarity based on MHC class I binding affinity (Kim, Y., Sidney, J., Pinilla, C., Sette, A. & Peters, B. Derivation of an amino acid similarity matrix for peptide: MHC binding and its application as a Bayesian prior. *BMC Bioinformatics* 10, 394, doi:10.1186/1471-2105-10-394 (2009)). Neoantigen candidates meeting an $IC_{50}$ affinity <500 nM were subsequently ranked based on MHC binding and T-cell epitope classifications. Tumor-associated expression levels derived from TCGA were used to generate a final ranking of candidate immunogenic peptides. Putative MANAs were synthesized using the PEPscreen platform (Sigma-Aldrich; St. Louis, MO). Lyophilized peptides were dissolved in minimal DMSO, resuspended in 100 &g/ml aliquots in AIM V media, and stored at −80° C.

T cell culture: T cells were cultured and evaluated for significant antigen-specific expansions as previously described, with minor modifications (Anagnostou, V. et al. *Cancer Discov* 7, 264-276, doi:10.1158/2159-8290.CD-16-0828 (2017); Le, D. T. et al. *Science* 357, 409-413, doi:10.1126/science.aan6733 (2017)).

On day 0, frozen PBMC from healthy donors or patients were thawed and counted. T cells were isolated using the EasySep Human T Cell Enrichment Kit (Stemcell Technologies; Vancouver, Canada). T cells were washed, counted, and resuspended at $2.0\times10^6$/ml in AIM V media supplemented with 50 μg/ml gentamicin (ThermoFisher Scientific; Waltham, MA). The T cell-negative fraction was washed, counted, and irradiated at 3,000 grads. The irradiated T cell-depleted fraction was washed and resuspended at $2.0\times10^6$/ml in AIM V media supplemented with 50 μg/ml gentamicin. Irradiated T cell-depleted cells were added to a 96-well, 48-well, 24-well, or 12-well plate at 125 μl, 250 μl, 500 μl, or 1,000 μl per well, respectively. An equal volume of T cells was then added to each well, along with 1 μg/ml of one of 13 HLA-matched CMV, EBV, or flu peptide epitopes (Sigma-Aldrich, St. Louis, MO) or without peptide. Cells were cultured for 10 days at 37° C. in a 5% $CO_2$ atmosphere, replacing half the culture media with fresh culture media containing 100 IU/ml IL-2, 50 ng/ml IL-7, and 50 ng/ml IL-15 (for final concentrations of 50 IU/ml IL-2, 25 ng/ml IL-7, and 25 ng/ml IL-15) on day 3 and replacing half the culture media with fresh media containing 200 IU/ml IL-2, 50 ng/ml IL-7, and 50 ng/ml IL-15 (for final concentrations of 100 IU/ml IL-2, 25 ng/ml IL-7, and 25 ng/ml IL-15) on day 7. If cells were to be used in IFNg ELISpot or IFNg/granzyme B fluorospot assays, cells were rested on day 9 by removing half the media and replacing with fresh media without cytokines. For cells to be used in TCR sequencing/FEST analysis, cells were not rested and were harvested on day 10. $CD8^+$ cells were further isolated from T cells cultured with putative MANAs using the EasySep Human $CD8^+$ T Cell Enrichment Kit (Stemcell Technologies) and plate magnet for added throughput.

For the generation of 20-day, restimulated cultures, autologous PBMC were incubated with 1 μg/ml relevant peptide for 2 h at 37° C. in a 5% $CO_2$ atmosphere, irradiated at 3,000 γ-rads, and were added to cultures at a 1:1 T cell: PBMC ratio on day 10 of the culture. Cells were fed on culture days 13 and 17 by replacing half the culture media with fresh media containing 200 IU/ml IL-2, 50 ng/ml IL-7, and 50 ng/ml IL-15 (for final concentrations of 100 IU/ml IL-2, 25 ng/ml IL-7, and 25 ng/ml IL-15). On day 20, T cells were harvested and washed for DNA extraction.

IFNg ELISpot assays: 10-day cultured cells or uncultured PBMC obtained from the same stock of cells used in culture were evaluated for IFNg production by a standard overnight enzyme-linked immunosorbent spot (ELISpot) assay. Briefly, 96-well nitrocellulose plates (EMD Millipore, Billerica, MA) were coated with anti-IFNγ monoclonal antibody (10 jig/ml; Mabtech, Stockholm, Sweden) and incubated overnight at 4° C. Plates were washed and blocked with IMDM supplemented with 10% heat-inactivated FBS for 2 h at 37° C. T cells stimulated for 10 days with CMV, EBV, and flu peptides were added to wells in duplicate at 50,000 cells per well and were stimulated overnight with PBMC pre-loaded with 1 jig/ml relevant peptide, a cytomegalovirus (CMV), Epstein-Barr virus (EBV), and influenza virus peptide pool (CEF), or no peptide in AIM V media. Cultured T cells with PBMC alone served as the background/negative control condition. Fresh-thawed PBMC were added to wells in singlet at 100,000 cells/well and were stimulated overnight with 1 μg/ml of the same peptides used in the T cell culture assays. PBMC alone in duplicate wells served as the background/negative control condition.

Staining and sorting of pentamer positive populations: T cells obtained from healthy donors were evaluated for specificity of known viral antigens. Fluorochrome-conjugated pentamers were synthesized (ProImmune, Oxford, UK) and used to stain PBMC from healthy donor JH014 per the manufacturer's instructions. Cells were co-stained with CD3, CD4, CD8, and CD45RO to identify antigen-specific memory $CD8^+$ T cells for sorting. The pentamer-positive population of interest was sorted using a BD FACSAria II and DNA was immediately extracted for TCR sequencing.

T cell receptor (TCR) sequencing and assessment of significant antigen-specific expansions: DNA was extracted from peptide-stimulated T cells, tumor tissue, and longitudinal pre- and post-treatment PBMC and pentamer-sorted T cells using a Qiagen DNA blood mini kit, DNA FFPE kit, or DNA blood kit, respectively (Qiagen). TCR Vβ CDR3 sequencing was performed using the survey (tissue, cultured cells, and pentamer-sorted cells) or deep (PBMC) resolution Immunoseq platforms (Adaptive Biotechnologies, Seattle, WA) (Carlson, C. S. et al. *Nat Commun* 4, 2680, doi: 10.1038/ncomms3680 (2013); Robins, H. S. et al. *Blood* 114, 4099-4107, doi:10.1182/blood-2009-04-217604 (2009)). Bioinformatic and biostatistical analysis of productive clones was performed to identify and evaluate antigen-specific expansions. Antigen-specific T cell clones were identified using the following criteria: 1) significant expansion of the relevant clone (Fisher exact test with Benjamini-Hochberg FDR, $p<0.01$) compared to T cells cultured without peptide, 2) significant expansion (Fisher exact test with Benjamini-Hochberg FDR, $p<0.01$) of this clone compared to every other peptide-stimulated culture, 3) and odds ratio >10 for the relevant clone, and 4) at least 10 reads in the relevant T cell culture. The peripheral and intratumoral representation of these antigen-specific clones was further analyzed.

Statistical and bioinformatic analysis: A custom script was developed in R/Bioconductor (R: A language and environment for statistical computing (R Foundation for Statistical Computing, Vienna, Austria, 2014); Gentleman, R. C. et al. Bioconductor: open software development for computational biology and bioinformatics. *Genome Biol* 5, R80, doi:10.1186/gb-2004-5-10-r80 (2004)) to load TCR sequencing data directly exported from Adaptive Biotechnologies ImmunoSEQ platform in V2 in the tab-delimited format, perform the analysis, and visualize and save results. For analysis, only productive clones were used and read counts were summarized for nucleotide sequences that translated into the same amino acid sequence. For each clone, Fisher's exact test was applied to compare the number of reads in a culture of interest (with peptide) and a reference culture (without peptide). The p-value adjusted by Benjamini-Hochberg procedure (FDR) (Benjamini, Y: & Hochberg, Y. *J Roy Stat Soc B Met* 57, 289-300 (1995)) was used to determine statistically significant specific expansions (FEST assay positive clones) that met the following criteria: 1) significantly expanded in the culture of interest compared to the reference culture (T cells cultured with cytokines but without peptide) at an FDR less than the specified threshold (<0.01), 2) significantly expanded in the culture of interest compared to every other culture performed in tandem (FDR<0.01), 3) have a positive odds ratio compared to the reference culture (e.g. >10), and 4) not significantly expanded in any other peptide-stimulated culture compared to the reference culture. All clones were subject to a 10-read lower threshold for consideration in the statistical analysis. FEST assay positive clones were saved in the output table and plotted at output heat maps using build-in R functions. The script was wrapped into a web application using Shiny Server (shiny: Web Application Framework for R. R package version 1.0.0 (2017)).

Results

Figure 3A:
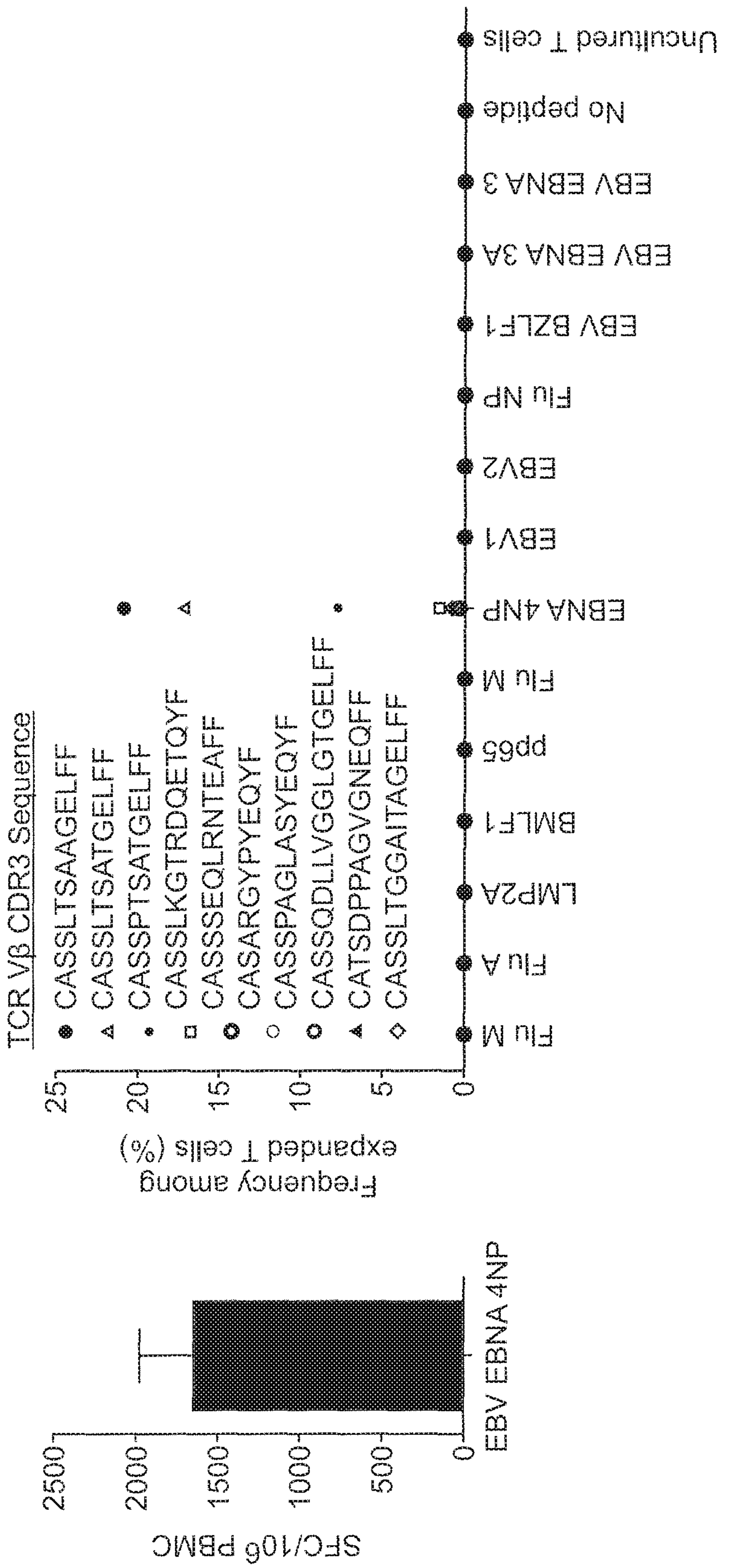
FIGS. 3A-3C are graphs showing that IFNγ ELISpot underestimates the breadth of the antigen-specific T cell response. T cells from healthy donor JH014 were stimulated with one of 13 known MHC class I-restricted epitopes and cultured for 10 days. IFNγ ELISpot was performed on an aliquot of cultured T cells (left panels) and TCR Vβ CDR3 sequencing was performed on the remaining T cells (right panels). ELISpot data are shown as the number of spot forming cells (SFC) per $10^6$ T cells with background subtracted for 3 tested epitopes. Accompanying clonotypic expansions are also shown in response to these 3 epitopes, EBV EBNA 4NP (FIG. 3A), EBV EBNA 3A (FIG. 3B), and EBV 1 (FIG. 3C). Background is the mean number of SFC detected without peptide stimulation in the ELISpot plus two standard deviations. TCR sequencing data are shown as the frequency of each clone among all T cells detected in the relevant culture.
Figure 3B:
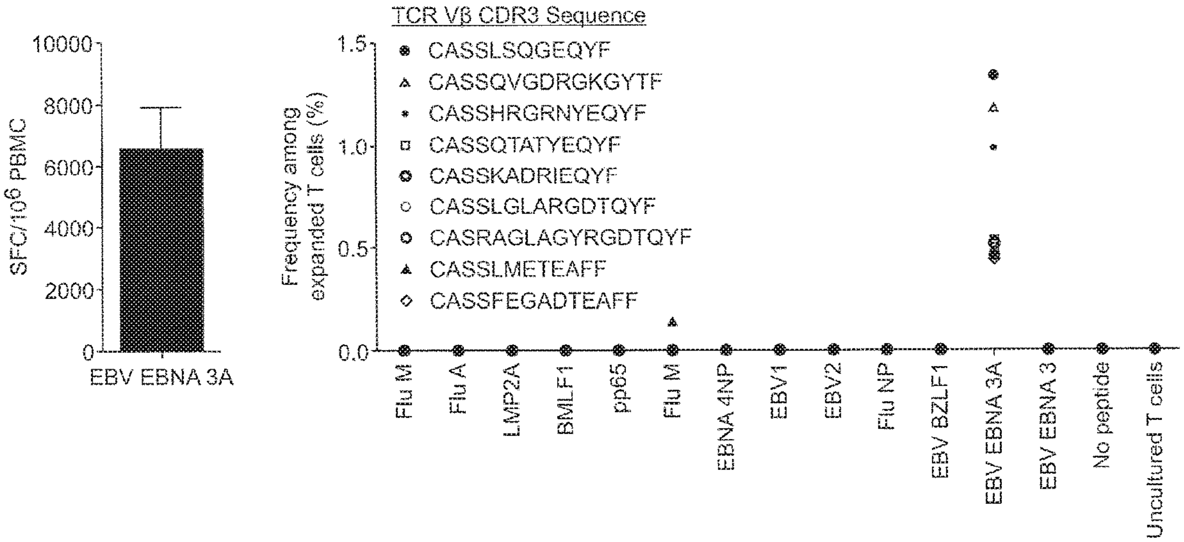
Figure 3C:
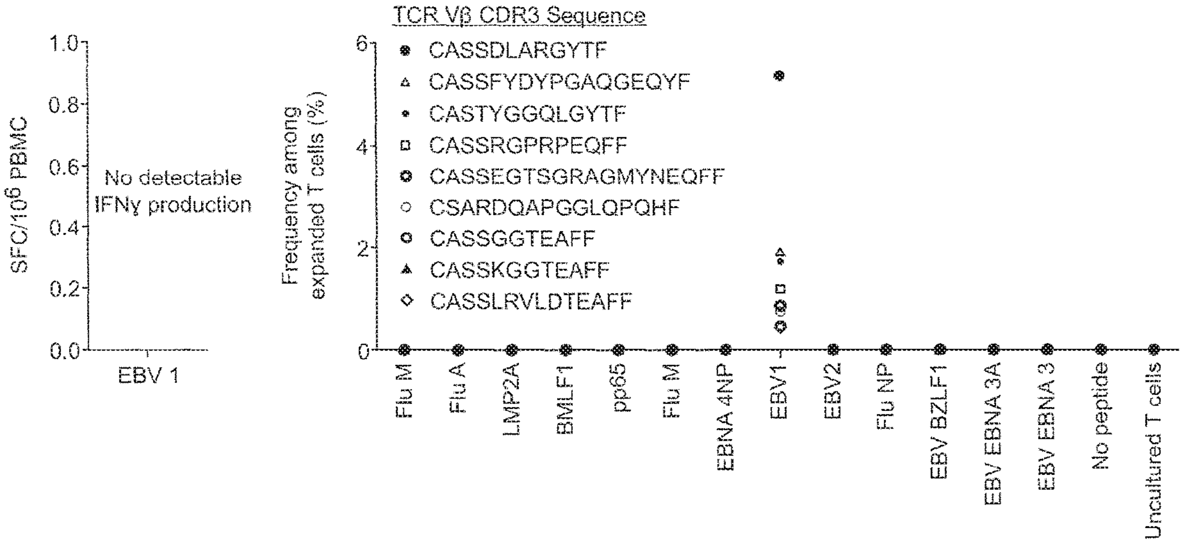

In vitro TCRVβ CDR3 clonotype amplification as a functional readout of T cell recognition—sensitivity comparison with ELISpot: Quantitative TCR sequencing is characterized by high sensitivity and elucidates the clonotypic hierarchy and composition of T cell populations (Carlson, C. S. et al. *Nat Commun* 4, 2680, doi:10.1038/ncomms3680 (2013); Robins, H. S. et al. *Blood* 114, 4099-4107, doi:10.1182/blood-2009-04-217604 (2009)). The molecular characterization of antigen-specific clonotypes can further provide a barcode tag to track and quantify antigen-specific T cells and allow for spatio-temporal characterization of the anti-tumor immune response, which is not achievable with ELISpot or flow cytometry-based approaches. To validate TCR sequencing as a metric of T cell recognition, viral antigens were first used and compared IFNg ELISpot with TCR Vβ CDR3 sequencing in healthy donors. Cytomegalovirus (CMV)-, influenza (flu)-, and Epstein Barr virus (EBV)-derived HLA-I epitopes are well-defined and induce $CD8^+$ T cell responses detectable by IFNγ ELISpot and tetramer/pentamer staining. ELISpot, used as a reference assay, was compared with the FEST assay to technically validate this new test. It was initially tested if peptide-induced T cell expansion could be observed in the absence of ELISpot positivity (no detectable antigen-specific IFNγ production). T cells from healthy donor JH014 were cultured for 10 days with multiple HLA-matched viral peptide epitopes (Table 1) or no peptide as a control. At the term of the culture, one aliquot of the cells was used to perform IFNγ ELISpot and the remaining cells were evaluated by TCR Vβ CDR3 sequencing. High-magnitude IFNγ production was observed that was associated with expansion of several T cell clones after a 10 day culture with the HLA A11-restricted EBV EBNA 4NP AVFDRKSDAK (FIG. 3A) and HLA B8-restricted EBV EBNA 3A FLRGRAYGL epitopes (FIG. 3B). Notably, while there was no IFNγ ELISpot signal for the HLA A11-restricted EBV EBNA-4 epitope, IVTDFSVIK, 9 T cell clones showed clear expansion (FIG. 3C). These ELISpot results were recapitulated in uncultured T cells. One of the features of this assay format that provides robust statistical specificity is that, for a set the T cell clones expanded upon stimulation with a given peptide, cultures with all the other peptides in the assay represent negative controls. As seen in FIGS. 3A-3C, the absence of amplification of the clonotypes in the other cultures indeed demonstrates the specificity of peptide-specific clonotypic expansion.

FEST associated biostatistics platform: A high throughput statistical analysis platform was developed, to combine with the experimental approach of the FEST assays in order to efficiently evaluate the specificity of the clonotypic expansion and therefore antigen-specific T cell recognition. To optimize data analysis and to streamline a stringent statistical analysis unlikely to result in false positives, TCR sequencing data were uploaded into a web-based biostatistics application that integrates the clonotypic amplification in each peptide-stimulated culture to determine the positivity and specificity of antigen-specific T cell recognition (statapps.one.jhmi.edu/FEST). A clonotype was considered antigen-specific if it 1) was significantly expanded in the relevant culture compared to T cells cultured without peptide at FDR<0.01, 2) was significantly expanded in the relevant culture compared to T cells cultured with every other peptide at FDR<0.01, 3) had greater than 10 reads, and 4) had an odds ratio >10 compared to the "no peptide" control. These criteria are stringent and were chosen to minimize false positives, given the sensitivity of the assay platform. In the analyses below, clones satisfying these criteria were considered to be FEST assay positive and were saved as an output of analysis (Table 3). However, each parameter can be adapted according to the investigator preferences. The web analysis platform also generates heatmaps showing odds ratio compared to the "no peptide" control for each peptide to which antigen recognition was detected and for all specifically and significantly expanded clones detected across all cultures. The FEST assays, comprised of an experimental T cell culture and computerized analytical tool, allows for efficient monitoring and analysis of antigen-specific T cell responses in a high throughput, turnkey fashion.

Specificity of the FEST assay: The high sensitivity of the FEST assay might be associated with decreased specificity and an increased false positive rate. To address this, the composition of the EBV EBNA 4NP-specific repertoire in healthy donor JH014 was first evaluated by performing duplicate sorting and TCR CDR3 Vβ sequencing experiments (sort #1 and sort #2) on pentamer-positive ($pMHC^+$) $CD8^+$ T cells. The EBV EBNA 4NP-specific population was detected at 0.2% of total T cells in both experiments (FIGS. 4A-4D, 7). TCR sequencing of $pMHC^+$ T cells demonstrated dominance of Vβ 28-01 within this antigen-specific population (FIG. 4B, Table 2), which is consistent with prior findings that different T cell clonotypes specific for the same antigen often preferentially utilize the same Vβ gene segment (Price, D. A. et al. *J Exp Med* 206, 923-936, doi: 10.1084/jem.20081127 (2009); Valkenburg, S. A. et al. *Proc Natl Acad Sci USA* 113, 4440-4445, doi:10.1073/pnas.1603106113 (2016); Du, V. Y. et al. *J Immunol* 196, 3276-3286, doi:10.4049/jimmunol.1502411 (2016); Kloverpris, H. N. et al. *J Immunol* 194, 5329-5345, doi:10.4049/jimmunol.1400854 (2015); Hill, B. J. et al. *J Immunol* 193, 5626-5636, doi:10.4049/jimmunol.1401017 (2014)). In comparison to 92.5% of T cells utilizing Vβ 28-01 in $pMHC^+$ T cells, only 7.0% of $pMHC^-$ $CD8^+$ T cells used this gene segment.

Two hundred thirteen and 104 unique CDR3 sequences were identified from sort #1 and sort #2, respectively, however only 9 of these sequences were shared between the two replicate $pMHC^+$ populations (FIG. 8, Table 2), with consistency in frequency between 4 of the most dominant clones, making up 90.0% and 88.9% of the total pentamer-positive T cells from each sort experiment. All 4 of these clones used the Vβ 28-01 gene. The remaining $pMHC^+$ T cells expressed over 40 different Vβ genes, with no clone making up more than 0.9% of the total pentamer-positive population (0.002% of total T cells).

Figures 4A, 4B:
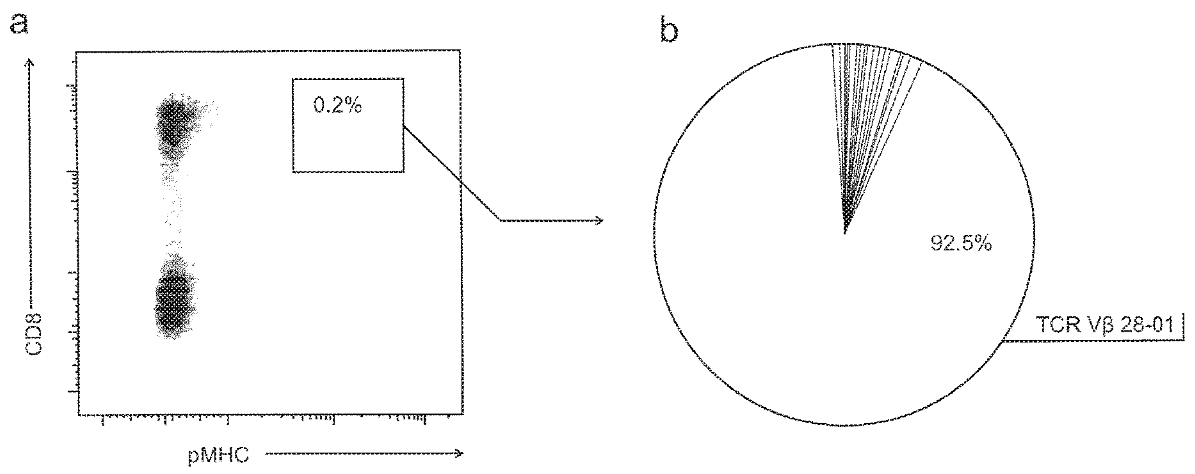
FIGS. 4A-4D show that FEST assays detect antigen-specific T cell responses with high specificity. T cells from healthy donor JH014 were stained with an EBV EBNA 4NP (Table 1) pentamer (FIG. 4A). TCR Vβ CDR3 sequencing was performed on epitope-specific T cells and the Vβ gene segment usage was evaluated (FIG. 4B). Clonotypes identified in the pentamer-sorted population were compared with those found in the same peptide-stimulated 10 day culture before (FIG. 4C, top) and after (FIG. 4C, bottom) the FEST biostatistical filtering to identify antigen-specific clones. The frequency (%) of each clonotype in the pMHC$^+$ population, in bulk uncultured T cells, and after the 10 day culture is also shown (FIG. 4D).
Figures 4C, 4D:
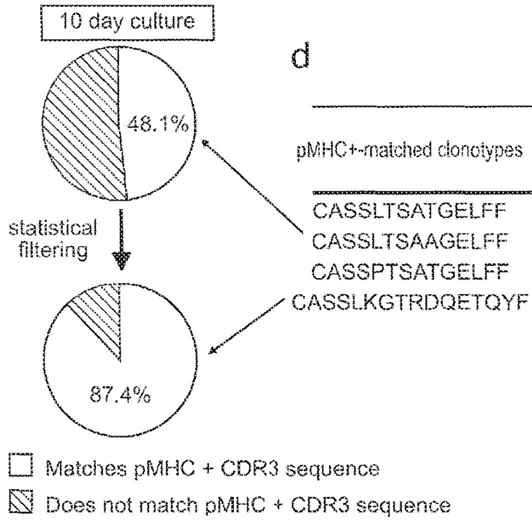
Figure 8:
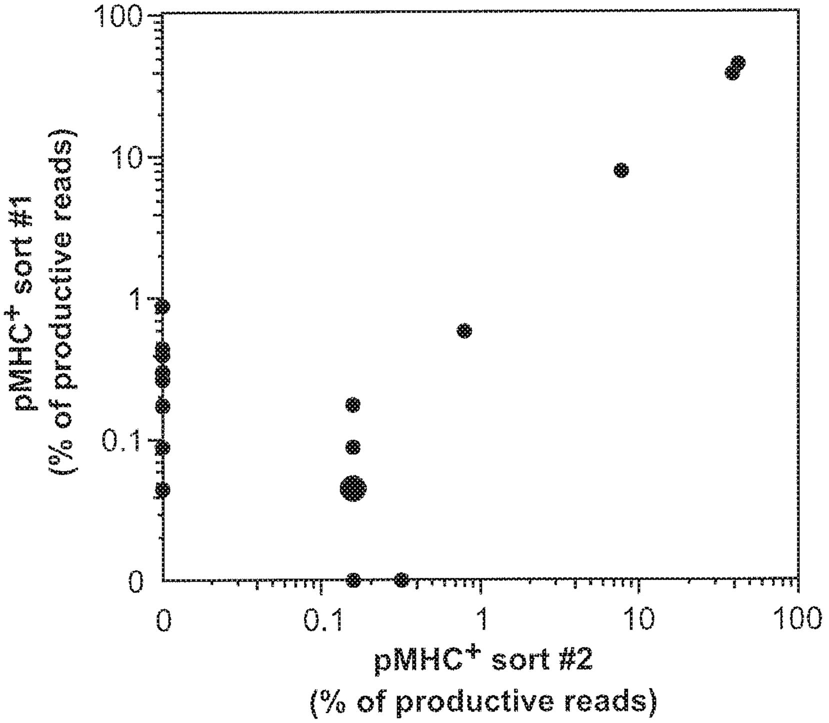
FIG. 8 are scatterplots showing the TCR Vβ CDR3 sequences observed in replicate pMHC$^+$ sort experiments. Replicate sorting and CDR3 sequencing experiments were performed on EBV EBNA 4NP-positive T cells from healthy donor JH014. Data are shown as the frequency (percent of total productive reads) of each clone detected in each sort. Each circle represents a unique Vβ CDR3 sequence, with the large circle representing 3 overlapping datapoints.

To evaluate the specificity of the FEST assay, the 9 common $pMHC^+$ CDR3 Vβ sequences identified in sorts #1 and #2 were first compared with those identified in bulk T cells after a 10 day culture and stimulation with the EBV EBNA 4NP epitope. Four unique clones, representing 48.1% of the T cell culture matched $pMHC^+$ CDR3 Vβ sequences. When the FEST associated biostatistical filtering was applied as described above to the clonotypic amplifications in this same 10 day culture, the specificity of these 4 clones were confirmed, which now made up 87.4% of the T cells that were identified as being antigen-positive by the FEST analysis (FIG. 4C). Of note, all 4 dominant clones used the Vβ 28-01 gene and matched the most frequent clones detected in the $pMHC^+$ populations (FIGS. 4D, 8 and Table 2). Thirty eight low frequency clonotypes that were positive by FEST analysis but absent in the $pMHC^+$ T cell fraction were neither in the uncultured nor 10 day cultured $pMHC^-$ $CD8^+$ T cell population, suggesting the presence of in vitro artifacts. To minimize these artifacts, $CD8^+$ T cells were isolated at the end of the 10 day culture before DNA isolation and TCR sequencing.

Because each peptide-stimulated culture serves as a negative control for all other cultures, the confidence in the specificity of T cell recognition can be improved by increasing the number of distinct peptide cultures. With 46 cultures, the estimated specificity of a unique clonotype would be nearly 98% (45/46), and a one-sided 95% confidence interval would run from 90%-100%. Therefore, with at least 46 cultures there is 95% confidence that specificity is above 90%. With 93 cultures, a unique clonotype has an estimated specificity of approximately 99% (95% C.I.=(95%-100%)).

Figures 5A, 5B, 5C:
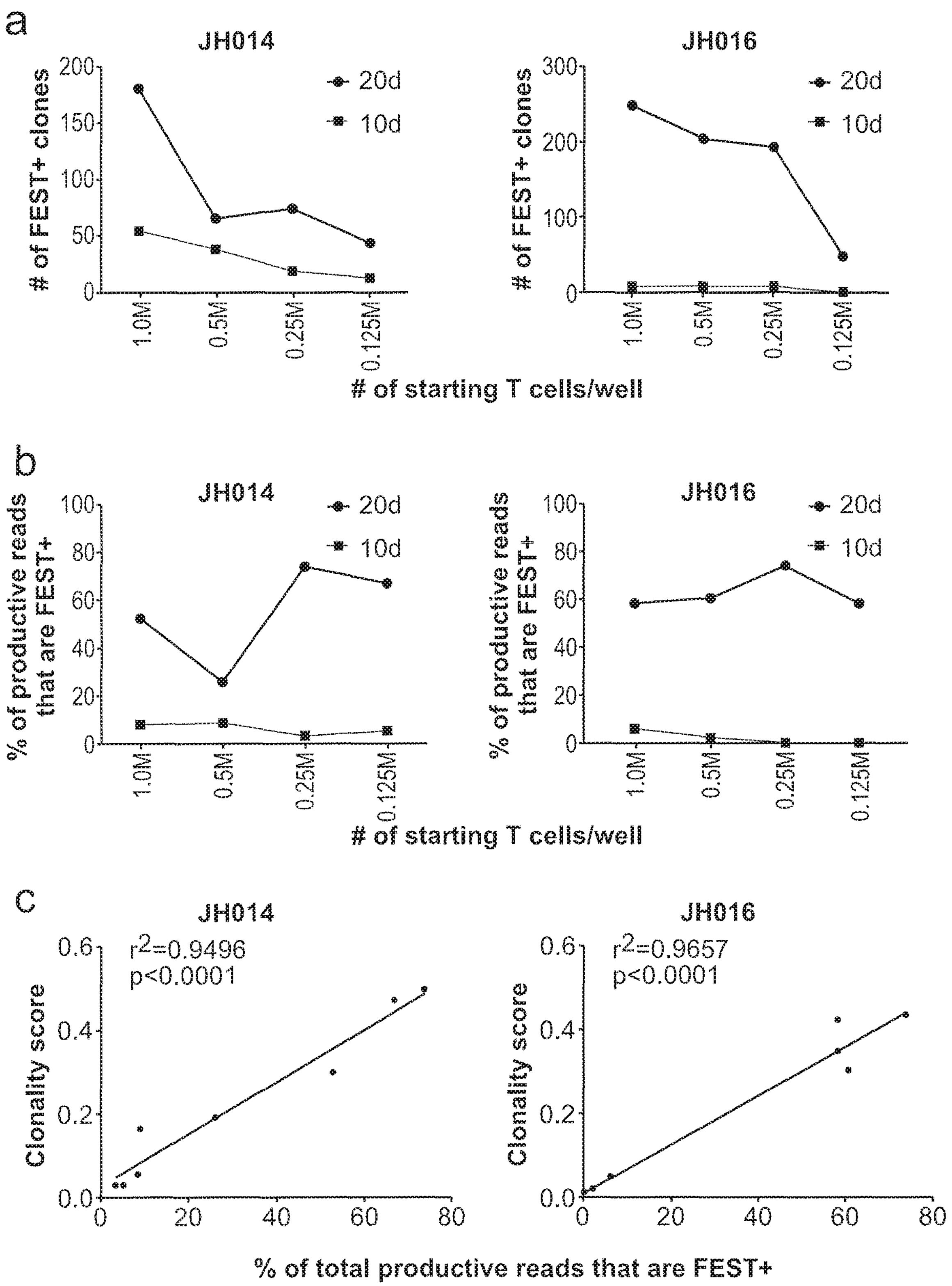
FIGS. 5A-5C are graphs showing the sensitivity of the FEST assay. Titrating numbers of T cells from healthy donors JH014 and JH016 were stimulated with a known EBV and flu peptide epitope, respectively, for 10 days or 20 days after a peptide re-stimulation on day 10. FEST-positive clones were identified in each condition. The number of FEST-positive clones (FIG. 5A), as well as the percent of the culture/productive reads that consisted of FEST-positive clones (FIG. 5B) are shown for each titrating cell number and culture length. The correlation between clonality and the percent of productive reads that were FEST-positive is shown for each donor (FIG. 5C).

Sensitivity of the FEST assay: The FEST assays rely on the identification of antigen-specific Vb CDR3 clonotypes and on their frequency following a 10 day in vitro expansion. Sensitivity of the FEST assays (i.e the detection of low frequency clonotypes) is expected to be highly dependent on the starting number of $CD8^+$ T cells in the 10 day culture. It was sought to determine 1) the optimal number of starting T cells required to accurately capture the breadth of the antigen-specific repertoire and 2) if clonotypes that were undetectable after a 10 day culture could be detected in 20 day cultures using a peptide restimulation step. Titrating numbers of T cells (from $1.25\times10^5$ to $1.0\times10^6$) obtained from two healthy donors were cultured for 10 and 20 days. T cells from donor JH014 were stimulated with the HLA A11-restricted EBV EBNA 4NP AVFDRKSDAK epitope shown in FIG. 3A and T cells from donor JH016 were stimulated with the HLA A2-restricted influenza M peptide GILGFVFTL. Peptide epitopes were chosen based on previously-documented reactivity in these two donors. The absolute number of unique clones that were expanded decreased as the starting cell number was decreased (FIG. 5A). Therefore, a higher number of starting cells results in the identification of a higher number of unique antigen-specific clonotypes that can then be tracked in peripheral blood lymphocytes or tissue. In both donors, the percent of productive reads (frequency of total T cells in the culture) that were significantly expanded compared to the "no peptide" control was consistently higher after a 20 day culture regardless of starting T cell number (FIG. 5B). This provides evidence that significantly expanded clones make up a greater percentage of the total T cell population after 20 days compared to 10 days. Indeed, there was a direct correlation between the percent of total productive reads that were significantly expanded and the clonality metric of the cultures (FIG. 5C), showing that clones expanded and detected via the FEST analytic platform directly contribute to the clonality of the culture. The percent of T cells that were significantly expanded in cultures without peptide stimulation had no correlation with clonality, highlighting the ability of the 10 day peptide-stimulated culture to specifically enrich for antigen-specific T cells. Despite the observance of more unique clones and a higher percent of clones that are FEST positive in the 20 day assay, clones were still expanded in all 10 day peptide cultures even at the lowest starting cell number of $1.25\times10^5$. Therefore, a 10 day culture with as few as $1.25\times10^5$ starting T cells per condition is sufficient to accurately screen a library of peptides for recognition of peripheral T cells with frequencies as low as 0.008% (10 cells in 125,000), with the sensitivity increasing to 0.001% when starting with $1.0\times10^6$ T cells (10 cells in $1.0\times10^6$).

Figure 9:
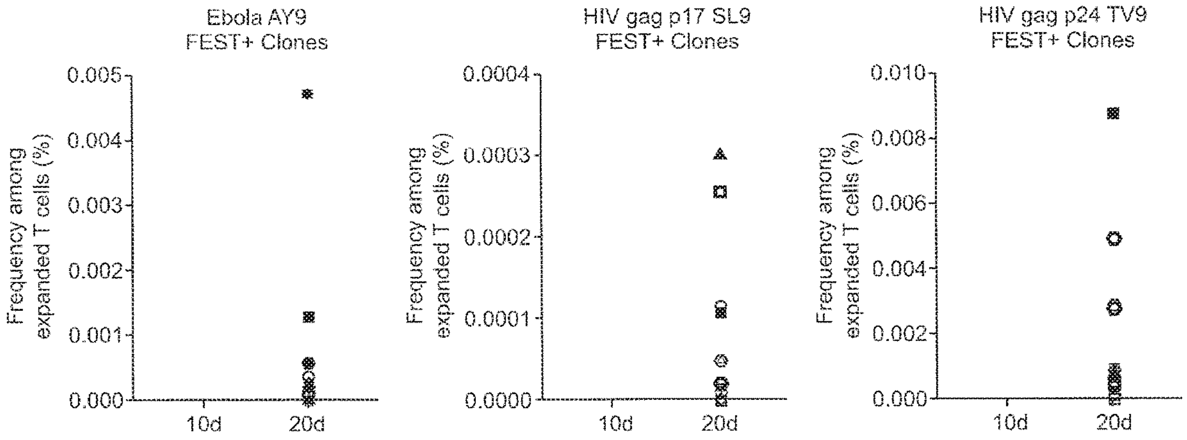
FIG. 9 are graphs showing the FEST-positive expansions detected to HIV-1 and ebola epitopes after 10-day and 20-day cultures. T cells from a healthy donor were cultured for 10 days in the presence of the HLA A*11:01-restricted ebolavirus $AY9_{AAGIAWIPY}$ (left), the HLA A*02:01-restricted HIV-1 $SL9_{SLYNTVATL}$ (middle), and the HLA A*02:01-restricted HIV-1 $TV9_{TLNAWVKVV}$ (right) epitopes, followed by TCR sequencing of the expanded T cells. In tandem cultures, cells were restimulated with irradiated peptide-loaded, autologous T cell-depleted PBMC and were cultured for an additional 10 days followed by TCR sequencing of the expanded T cells. Within each graph, each symbol represents a unique significantly and specifically expanded T cell clone as determined by the FEST analysis platform. Data are shown as the percent among all T cells after expansion in the relevant culture

The possibility that the 20 day culture was identifying clones expanded from naïve precursors and was not quantifying the endogenous recall response, was next assessed. T cells from healthy donor JH014 were cultured with two well-documented HIV-1 and one Ebola HLA A*02:01-restricted peptides. After 10 days, there were no clones that significantly expanded in response to any of the peptides compared to the no peptide control. Strikingly, after a restimulation and 20 days of culture, there was significant expansion of 61, 108, and 111 clones in response to the HIV-1 gag SL9, HIV-1 gag TV9, and ebola AY9 epitopes, respectively (FIG. 9). These data demonstrate that a restimulation and 20 day culture can result in the detection of primary T cell responses and is therefore not suitable when evaluating the endogenous memory repertoire, but may inform on the repertoire that is available for vaccination.

Validation of MANAFEST to detect anti-tumor immune responses in patients receiving anti-PD-1: While T cell responses to viral antigens are often immunodominant (Motozono, C. et al. *J Immunol* 192, 3428-3434, doi:10.4049/jimmunol.1302667 (2014); Wu, C. et al. *Proc Natl Acad Sci USA* 108, 9178-9183, doi:10.1073/pnas.1105624108 (2011); Steven, N. M. et al. *J Exp Med* 185, 1605-1617 (1997); Betts, M. R. et al. *Blood* 107, 4781-4789, doi:10.1182/blood-2005-12, 4818 (2006)), MANA-specific T cells could potentially be diverse and subdominant as well as functionally compromised (low cytokine production). It was therefore considered that the breadth and magnitude of the endogenous immune response in cancer patients may be substantially underestimated using ELISpot or multimer-based assays and that improved characterization of this response could be attained by using the FEST assay approach. Moreover, immune monitoring of the clinical response to checkpoint blockade requires T cell clonotype tracking in tissue and longitudinal peripheral blood samples to confirm the amplification of MANA-specific TCR Vβ clonotypes upon treatment, a parameter that is not achievable by ELISpot. As a proof of principle, MANAFEST was performed on cells obtained from JH124, a patient with stage IIB squamous NSCLC who achieved a complete pathological response following two doses of nivolumab (anti-PD-1 therapy). Whole exome sequencing was performed in pre-treatment tumor and matched normal tissue and tumor-specific alterations were analyzed using a neoantigen prediction pipeline to identify candidate MANAs specific to the patient's HLA haplotype. T cells obtained 4 weeks post initiation of nivolumab were cultured for 10 days with one of 47 putative MANAs (Table 3) and resulting expanded T cells were isolated for TCR Vβ CDR3 sequencing and MANAFEST analysis. TCR sequencing data was also used from tumor infiltrating lymphocytes to identify intra-tumoral clones.

Figure 6A:
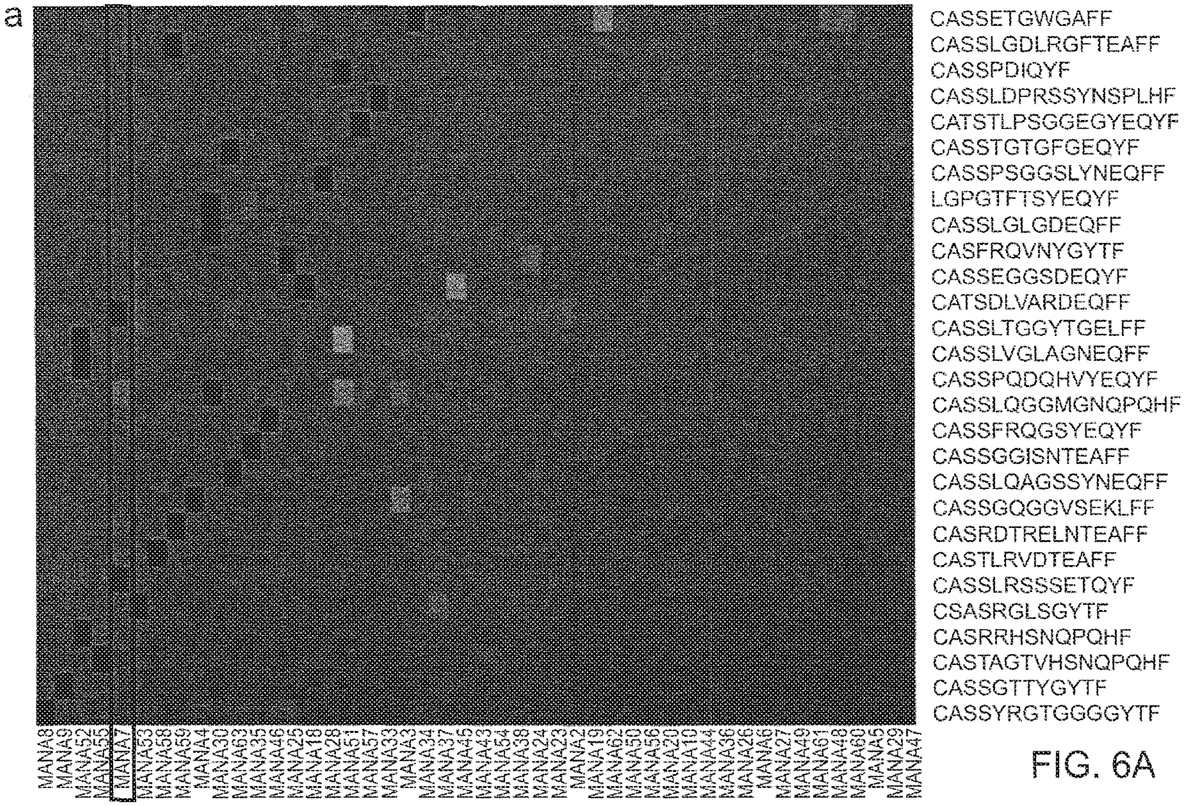
FIGS. 6A-6D show that the MANAFEST assay identifies multiple recognized MANAs and provides TCR barcodes to enable tracking of the anti-tumor immune response in tissue and peripheral blood. Recognition of candidate MANAs was evaluated by the MANAFEST assay in a patient with NSCLC being treated with anti-PD-1. A heatmap generated by the FEST analysis platform shows all MANA/clone pairs to which significant antigen-specific expansion was detected, with expansions to MANA #7 outlined in red (FIG. 6A). T cell clonotypes specific for MANA #7 as determined by the FEST analysis platform are shown as the frequency after culture (FIG. 6B), as well as in the primary tumor (FIG. 6C), and in longitudinal pre- and post-treatment peripheral blood T cells (FIG. 6D). Data are shown as the percent among all TCR reads detected.
Figure 6B:
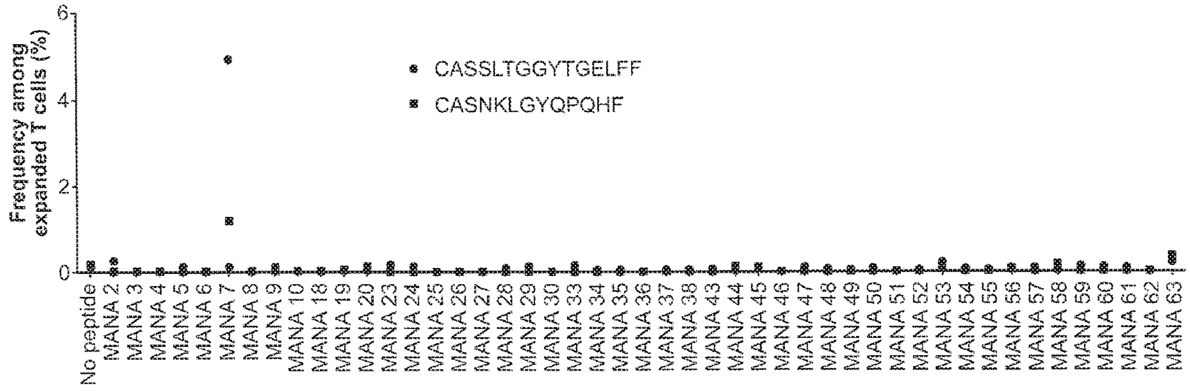
Figures 6C, 6D:
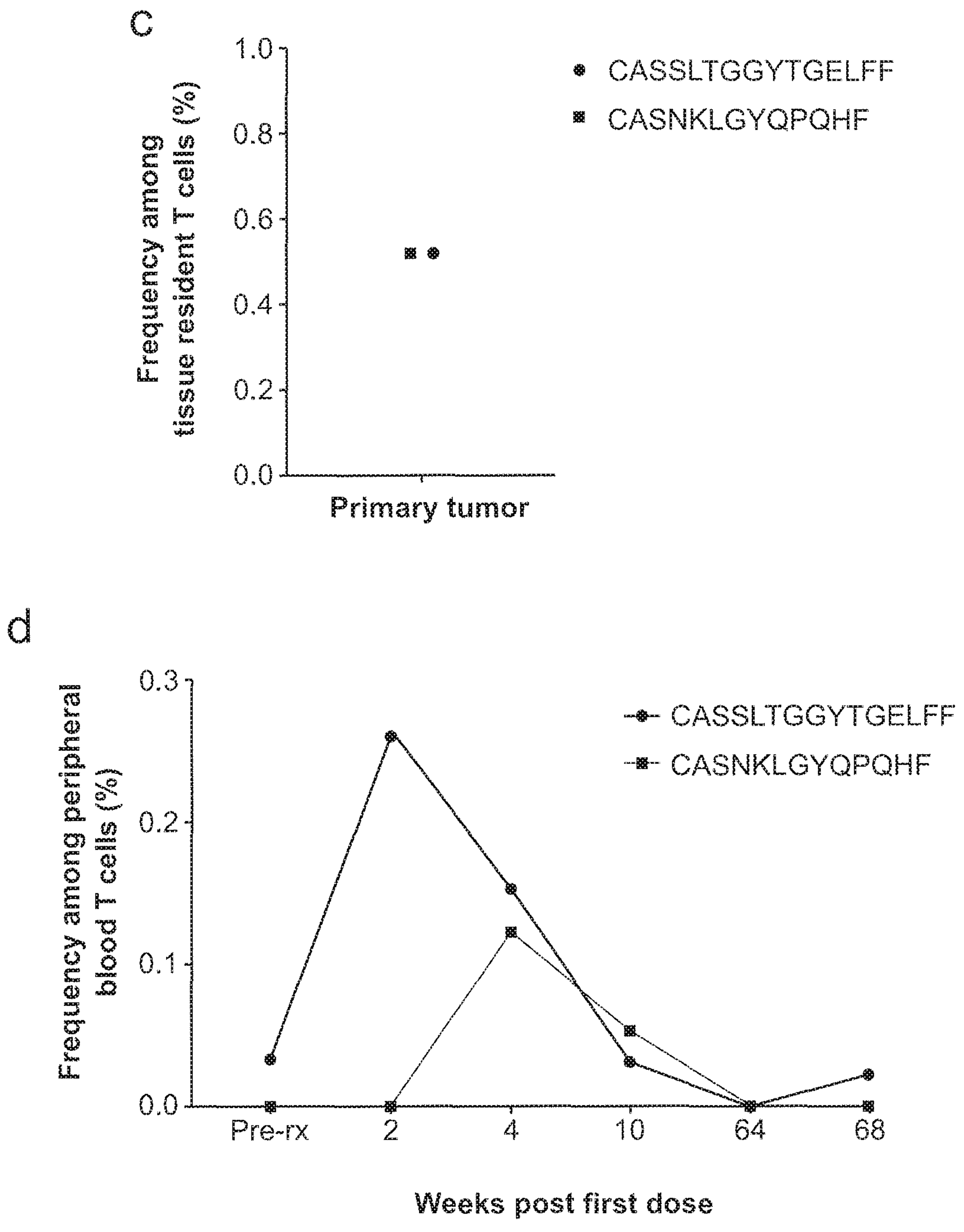
Figure 7:
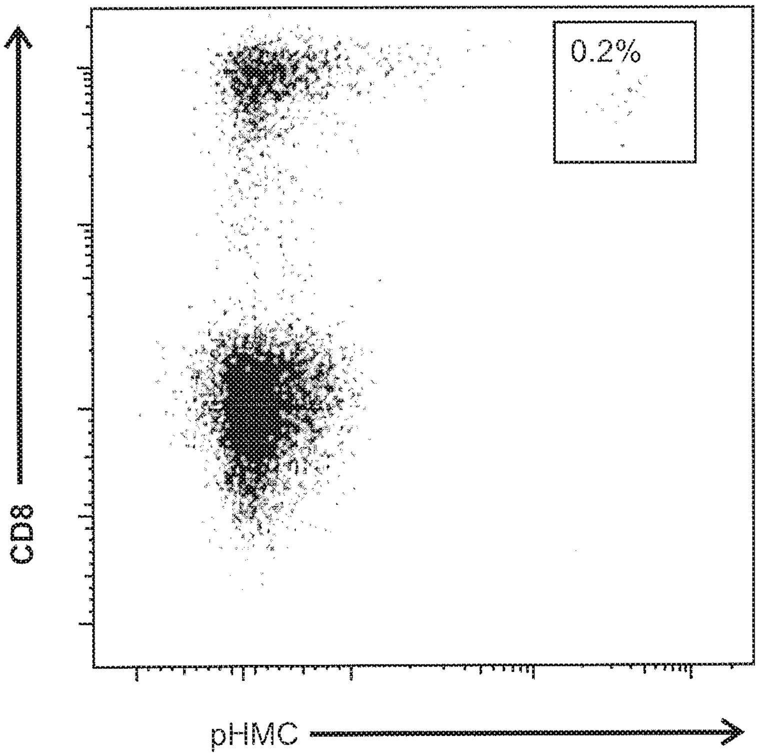
FIG. 7 is a scatterplot showing the replicate pMHC$^+$ CD8$^+$ T cell sort. Additional flow cytometry and sorting experiment on EBV EBNA 4NP-pentamer positive (pMHC$^+$) T cells, followed by TCR Vb CDR3 sequencing of antigen-specific cells.

Twenty-one out of 47 putative MANAs induced significant and specific T cell expansions and can be visualized as a heatmap output from the MANAFEST Web Application (FIG. 6A). Of the 28 clones that were expanded in response to these 21 MANAs, 2 were detected in the primary tumor and were both specific for the putative HLA A*25:01-restricted EVIVPLSGW MANA derived from a somatic sequence alteration in the ARVCF gene (FIGS. 6B, 6C and Table 3). Longitudinal analysis of these clones demonstrated a peripheral expansion upon nivolumab administration that decreased by 10 weeks post-first dose and was reminiscent of acute responses to viral infections (FIG. 6D). Aside from the frequency after culture, in tissue, and in serial peripheral blood samples, additional parameters are outputted from the FEST analysis that can be correlated with treatment response (see output for patient JH124 in Tables 4, 5 and 6). These parameters include the magnitude of in vitro expansion compared to uncultured T cells and to the "no peptide" control condition, the number of clones that are significantly expanded in response to a given candidate MANA, and the sum frequency of FEST-positive clones in response to each MANA after culture.

Discussion

The rapid development of personalized cancer immunotherapies as well as the imperative to develop biomarkers predictive of immunotherapy responses calls for routine high throughput assays that monitor the anti-tumor immune response (Couzin-Frankel, J. *Science* 342, 1432-1433, doi: 10.1126/science.342.6165.1432 (2013)). These assays will likely be a critical biomarker for the efficiency of the immunotherapeutic treatment and can also determine the eligibility of patients for immunotherapy based on detection of a preexisting anti-tumor immune response (Topalian, S. L., et al. *Nat Rev Cancer* 16, 275-287, doi:10.1038/nrc.2016.36 (2016)). With the recent development of NGS technologies it has become feasible to characterize mutations in the tumor exome and the TCR recognizing the neoantigens derived from these mutations (Kirsch, I., et al. *Mol Oncol* 9, 2063-2070, doi:10.1016/j.molonc.2015.09.003 (2015); Vogelstein, B. et al. Cancer genome landscapes. *Science* 339, 1546-1558, doi:10.1126/science.1235122 (2013)). Because amplification of selective TCRVb clonotypes in tumor tissue has been proposed as a surrogate biomarker of MANA recognition (Pasetto, A. et al. *Cancer Immunol Res* 4, 734-743, doi:10.1158/2326-6066.CIR-16-0001 (2016)), the MANAFEST assay introduced herein, is based on tumor exome-guided identification of putative MANAs and the measure of the MANA-specific TCR clonotypic amplification following patient T cell stimulation. It was shown that epitope-triggered clonal expansion can be observed in the absence of detectable IFNg production, and that ELISpot likely underestimates the peripheral T cell response. Furthermore, TCR sequencing underscores the diversity of the T cell response to a single HLA-restricted epitope. Altogether, these results validate TCR sequencing of a 10 day peptide-stimulated culture as the experimental core of the functional expansion of specific T-cells (FEST) assays to monitor antigen-specific T cell responses.

In comparison with existing methods, the FEST assays are highly sensitive and specific, and enable the tracking of antigen-specific TCR clonotype dynamics in T cell DNA derived from tissues and peripheral blood. These methods can be used to detect virus- and MANA-specific responses with greater sensitivity and throughput than current methods, and can be expanded to a variety of antigens including tumor associated antigens (TAAFEST), viral antigens (VIRAFEST), bacterial antigens (BactiFEST), and autoantigens (AutoFEST). This assay works independently of the limitations often met in traditional tests such as the low frequency and functional state of the T cells (ELISpot), HLA availability for multimer approaches (combinatorial encoding multimer), and the inadequacy of routine high throughput clinical monitoring (ELISpot). The molecular characterization of each TCR clonotype amplified in response to the specific MANA provides a convenient T cell clone-associated barcode, or “molecular tag”, to enable tracking of anti-tumor T cells in a multitude of fresh, fixed, and frozen cell and tissue types. This approach can inform on the spatiotemporal distribution of the anti-mutanome in serial peripheral blood samples or in differential geographic regions of the tumor. The MANAFEST method has already been used to detect and monitor peripheral and intratumoral MANA-specific T cell responses in NSCLC patients with acquired resistance to checkpoint blockade (Anagnostou, V. et al. *Cancer Discov* 7, 264-276, doi:10.1158/2159-8290.CD-16-0828 (2017)) and a colorectal cancer patient with a sustained partial response to pembrolizumab (Le, D. T. et al. *Science* 357, 409-413, doi:10.1126/science.aan6733 (2017)).

Consequently, FEST-based monitoring provides critical information in terms of the intensity (magnitude of expansion), diversity (distinct unique CDR3 sequences), dynamics (unique sequence reads at different time points), and geographic distribution (tissue-resident and periphery) of the anti-tumor immune response at a magnitude that will never be reached with any of the traditional assays. In comparison with traditional existing methods, such as ELISpot and multimer approaches, it is shown herein, that the setup of the test is easily feasible, using direct incubation of peptides with patient T cells, does not require specialized equipment such as a multiparameter flow cytometer or an ELISpot reader, permits a higher throughput, and also facilitates a multi-center standardization for data sharing, databasing, and computational identification of biomarkers. The throughput of this assay can be dramatically increased by identifying clonotypic amplifications to pools prior to testing individual peptides present in positive pools.

Additionally, because the test does not require the derivation of autologous antigen presenting cells as required for the TMG approach, relatively fewer numbers of PBMC and therefore smaller samples are necessary to detect MANA-specific T cells with high sensitivity. Although whole exome sequencing and TCR sequencing are currently costly methods, NGS has become relatively affordable and routine in patients receiving immunotherapy and clinical use of whole exome sequencing may be envisaged in the future. In the context of widespread use of immunotherapy, the characteristics aforementioned may facilitate the compatibility with clinical practice (liquid biopsy) and improved patient comfort (non-invasive sampling). Importantly, the computational pipeline to predict HLA-restricted MANAs and the web-based biostatistics used to identify immunogenic MANAs by FEST-based assays allow flexibility in the decision making regarding the selection of MANAs to accommodate high or low mutational density and in the determination of a positive MANA-specific response by modifying the desired alpha and odds ratio threshold.

While the assays described here evaluated MHC class I-restricted responses, this assay can be easily adapted to assess $CD4^{+}$/MHC class II-restricted responses as well. Additionally, because antigen-specific $T_{reg}$ are of particular interest in cancer patients, this T cell subpopulation can be assayed using the FEST approach.

Importantly, the scientific application and translational perspectives of MANAFEST are indispensable, owing to the capacity for molecular characterization of the TCR sequences associated with MANA recognition that can be coordinated across patients or histologies and between institutions to identify common genomic features associated with immunogenicity of tumors and common structural motifs of the TCR (Faham, M. et al. *Arthritis Rheumatol*, doi:10.1002/art.40028 (2016)). A central repository of these data would help define molecular motifs that could inform on the capacity of cancer patients to mount immune responses to their cancer and on their eligibility for immune checkpoint modulation. The MANAFEST assay is therefore expected to become a unique tool that could serve as a pan-cancer predictive biomarker of response to immunotherapy.

TABLE 1

Viral peptide epitopes tested in healthy donor JH014
(Table discloses SEQ ID NOS 1-13, respectively, in order of appearance)

| Peptide Name | Source | Protein | AA Sequence | HLA Restriction |
|---|---|---|---|---|
| Flu M | influenza | matrix | GILGFVFTL | A2 |
| Flu A | influenza | polymorase acidic | FMYSDFHFI | A2 |
| EBV LMP2A | human herpesvirus 4 | latent membrane protein 2A | CLGGLLTMV | A2 |
| EBV BMLF1 | human herpesvirus 4 | BMLF1 | GLCTLVAML | A2 |
| HcMV pp65 | human cytomegalovirus | phosphoprotein 65 | NLVPMVATV | A*02: 01 |
| Flu M | influenza | matrix | SIIPSGPLK | A11 |
| EBV EBNA 4NP | human herpesvirus 4 | Epstein-Barr nuclear antigen 1 | AVFDRKSDAK | A11 |
| EBV 1 | human herpesvirus 4 | Epstein-Barr nuclear antigen 1 | IVTDFSVIK | A11 |
| EBV 2 | human herpesvirus 4 | BRLF1 | ATIGTAMYK | A11 |
| Flu NP | influenza | nucleoprotein | ELRSRYWAI | B8 |
| EBV BZLF-1 | human herpesvirus 4 | BZLF1 | RAKFKQLL | B8 |
| EBV EBNA 3A | human herpesvirus 4 | Epstein-Barr nuclear antigen 3 | FLRGRAYGL | B8 |
| EBV EBNA 3 | human herpesvirus 4 | Epstein-Barr nuclear antigen 3 | QAKWRLQTL | B8 |

TABLE 2

Clonotypes detected in pentamer-sorted T cells
(Table discloses SEQ ID NOS 14-223, respectively, in order of appearance)

| CDR3 Amino Add Sequence* | Vβ Gene | CDR3 Frequency in EBV EBNA 4NP pMHC + sort #1 | CDR3 Frequency In EBV EBNA 4NP pMHC + sort #2 |
|---|---|---|---|
| **CASSLTSATGELFF** | TCRBV28-01*01 | 43.982301 | 41.706161 |
| **CASSLTSAAGELFF** | TCRBV28-01*01 | 37.654867 | 38.704581 |
| **CASSPTSATGELFF** | TCRBV28-01*01 | 7.787611 | 7.740916 |
| **CASSLKGTRDQETQYF** | TCRBV28-01*01 | 0.57521 | 0.789889 |
| CASSRHHNKETQYF | TCRBV28-01*01 | 0.044248 | 0.157978 |
| CSAKLAGYQTGELFF | TCRBV20 | 0.176991 | 0.157978 |
| CSARTLGPGDEQYF | TCRBV20 | 0.044248 | 0.157978 |
| CSVEIGGEQYF | TCRBV29-01*01 | 0.044248 | 0.157978 |
| CSVLGGTSGAQETQYF | TCRBV29-01*01 | 0.088496 | 0.157978 |
| CASSIPNPIWHHQPQHF | TCRBV03 | 0 | 0.315956 |
| CASSKATSSQSRANVLTF | TCRBV07-04*01 | 0 | 0.315956 |
| CASSLGGMDYGYTF | TCRBV05-06*01 | 0 | 0.315956 |
| CASSLGVGYTF | TCRBV07-09 | 0 | 0.315956 |
| CASSLRQGTTEAFF | TCRBV28-01*01 | 0 | 0.315956 |
| CSASAGLVTEAFF | TCRBV20 | 0 | 0.315956 |
| CARGQGDGYTF | TCRBV30-01*01 | 0 | 0.157978 |
| CASNREPNSPLHF | TCRBV13-01*01 | 0 | 0.157978 |
| CASQLGLGYEQYF | TCRBV27-01*01 | 0 | 0.157978 |
| CASRAPDLAPYEQYF | TCRBV28-01*01 | 0 | 0.157978 |
| CASRGYDREAFF | TCRBV06-06 | 0 | 0.157978 |

TABLE 2 -continued

Clonotypes detected in pentamer-sorted T cells
(Table discloses SEQ ID NOS 14-223, respectively, in order of appearance)

| CDR3 Amino Add Sequence* | Vβ Gene | CDR3 Frequency in EBV EBNA 4NP pMHC + sort #1 | CDR3 Frequency In EBV EBNA 4NP pMHC + sort #2 |
|---|---|---|---|
| CASRLKQSRANVLTF | TCRBV09-01 | 0 | 0.157978 |
| CASRPTGVLEQYF | TCRBV03 | 0 | 0.157978 |
| CASSAQGVIGDEQFF | TCRBV09-01 | 0 | 0.157978 |
| CASSCDHLHARNTIYF | TCRBV03 | 0 | 0.157978 |
| CASSDQGSDYEQYF | TCRBV02-01*01 | 0 | 0.157978 |
| CASSFGLAGLKTGELFF | TCRBV06 | 0 | 0.157978 |
| CASSFGQMNTEAFF | TCRBV11-02*02 | 0 | 0.157978 |
| CASSFGSHTEAFF | TCRBV06-06 | 0 | 0.157978 |
| CASSFLTQETQYF | TCRBV13-01*01 | 0 | 0.157978 |
| CASSFPGEASYEQYF | TCRBV28-01*01 | 0 | 0.157978 |
| CASSGADSNSPLHF | TCRBV03 | 0 | 0.157978 |
| CASSGGTADEQFF | TCRBV13-01*01 | 0 | 0.157978 |
| CASSLLASGNTIYF | TCRBV07-01*01 | 0 | 0.157978 |
| CASSLNSQGQSRANVLTF | TCRBV07-01*01 | 0 | 0.157978 |
| CASSLQGTSGRDNEQFF | TCRBV27-01*01 | 0 | 0.157978 |
| CASSLTPGQMNTEAFF | TCRBV05-06*01 | 0 | 0.157978 |
| CASSNQGLWHHQPQHF | TCRBV03 | 0 | 0.157978 |
| CASSNTGTVYGYTF | TCRBV06-05*01 | 0 | 0.157978 |
| CASSPDWGTGELFF | TCRBV04-01*01 | 0 | 0.157978 |
| CASSPGGLAKNIQYF | TCRBV28-01*01 | 0 | 0.157978 |
| CASSPGTANQPQHF | TCRBV09-01 | 0 | 0.157978 |
| CASSQDGGTVEQYF | TCRBV04-02*01 | 0 | 0.157978 |
| CASSQEDEYNEQFF | TCRBV04-01*01 | 0 | 0.157978 |
| CASSQEFNQPQHF | TCRBV03 | 0 | 0.157978 |
| CASSQHTQQSRANVLTF | TCRBV23-01*01 | 0 | 0.157978 |
| CASSQQETYEQYF | TCRBV06-05*01 | 0 | 0.157978 |
| CASSRASSYEQYF | TCRBV27-01*01 | 0 | 0.157978 |
| CASSRFVTMTSRANVLTF | TCRBV07-09 | 0 | 0.157978 |
| CASSSRGNEQFF | TCRBV09-01 | 0 | 0.157978 |
| CASSTLGQLNTEAFF | TCRBV09-01 | 0 | 0.157978 |
| CASSTTTGPSDNEQFF | TCRBV18-01*01 | 0 | 0.157978 |
| CASSWVANIQYF | TCRBV28-01*01 | 0 | 0.157978 |
| CASTLRRNEQYF | TCRBV06-06 | 0 | 0.157978 |
| CASVGPPNYGYTF | TCRBV11-02*02 | 0 | 0.157978 |
| CATGNKDEQYF | TCRBV30-01*02 | 0 | 0.157978 |
| CATRGGQGKGLADYNEQFF | TCRBV24 | 0 | 0.157978 |
| CESQGKRKTQYF | TCRBV09-01 | 0 | 0.157978 |
| CSAKPAGYQTGELFF | TCRBV20 | 0 | 0.157978 |

TABLE 2 -continued

Clonotypes detected in pentamer-sorted T cells
(Table discloses SEQ ID NOS 14-223, respectively, in order of appearance)

| CDR3 Amino Add Sequence* | Vβ Gene | CDR3 Frequency in EBV EBNA 4NP pMHC + sort #1 | CDR3 Frequency In EBV EBNA 4NP pMHC + sort #2 |
|---|---|---|---|
| CSAREGQGRARQETQYF | TCRBV20 | 0 | 0.157978 |
| CSASSDKNIQYF | TCRBV20 | 0 | 0.157978 |
| CSATSGYSYEQYF | TCRBV0 | 0 | 0.157978 |
| CSGLSDWAQYF | TCRBV29-01*01 | 0 | 0.157978 |
| CSVARSGKNYEQYF | TCRBV29-01*01 | 0 | 0.157978 |
| CSVEEAASGSPYEQYF | TCRBV29-01*01 | 0 | 0.157978 |
| CSVGTGGTNEKLFF | TCRBV29-01*01 | 0 | 0.157978 |
| CSVLGVLNTEAFF | TCRBV29-01*01 | 0 | 0.157978 |
| CSVVLGAGYEQYF | TCRBV29*01*01 | 0 | 0.157978 |
| RAIRVQGDWTEAFF | TCRBV10-03*01 | 0 | 0.157978 |
| CAIRGTSGRTGELFF | TCRBV10-03*01 | 0.044248 | 0 |
| CAISGDSSGANVLTF | TCRBV10-03*01 | 0.044248 | 0 |
| CAISPQVGEQYF | TCRBV10-03*01 | 0.044248 | 0 |
| CAPNGGGNTIYF | TCRBV30-01*01 | 0.044248 | 0 |
| CASATGVRAYEQYF | TCRBV09-01 | 0.044248 | 0 |
| CASGPDRTYEQYF | TCRBV02-01*01 | 0.044248 | 0 |
| CASGPFPRDSSYNEQFF | TCRBV06 | 0.044248 | 0 |
| CASGQGNQDTQYF | TCRBV06-06 | 0.044248 | 0 |
| CASHGAPGRAGKATQYF | TCRBV03 | 0.044248 | 0 |
| CASLGGIEAFF | TCRBV16-01 | 0.044248 | 0 |
| CASMRREVYEQFF | TCRBV07-09 | 0.044248 | 0 |
| CASNRSTQSRANVLTF | TCRBV05-02*01 | 0.044248 | 0 |
| CASQTSGSYEQYF | TCRBV28-01*01 | 0.044248 | 0 |
| CASRATMGTGQETQYF | TCRBV06 | 0.044248 | 0 |
| CASRDGDTGELFF | TCRBV06-01*01 | 0.088496 | 0 |
| CASRGRQAYEQYF | TCRBV02-01*01 | 0.044248 | 0 |
| CASRRIRELLTDTQYF | TCRBV28-01*01 | 0.044248 | 0 |
| CASRRPGLDNYGYTF | TCRBV28-01*01 | 0.044248 | 0 |
| CASRRSGLDNYGYTF | TCRBV28-01*01 | 0.044248 | 0 |
| CASRTAGEPHEQYF | TCRBV13-01*01 | 0.088496 | 0 |
| CASSAGLNTEAFF | TCRBV06-04 | 0.088496 | 0 |
| CASSALGNQPQHF | TCRBV03 | 0.088496 | 0 |
| CASSAPGHVGHGYTF | TCRBV25-01*01 | 0.088496 | 0 |
| CASSEATGRSEKLFF | TCRBV02-01*01 | 0.044248 | 0 |
| CASSEGFGEKLFF | TCRBV25-01*01 | 0.088496 | 0 |
| CASSFAGGGNTEAFF | TCRBV05-01*01 | 0.044248 | 0 |
| CASSFATSGFTDTQYF | TCRBV12 | 0.044248 | 0 |

TABLE 2 -continued

Clonotypes detected in pentamer-sorted T cells
(Table discloses SEQ ID NOS 14-223, respectively, in order of appearance)

| CDR3 Amino Add Sequence* | Vβ Gene | CDR3 Frequency in EBV EBNA 4NP pMHC + sort #1 | CDR3 Frequency In EBV EBNA 4NP pMHC + sort #2 |
|---|---|---|---|
| CASSFDGSLNTEAFF | TCRBV06 | 0.044248 | 0 |
| CASSFGDSAYNEQFF | TCRBV06-06 | 0.044248 | 0 |
| CASSFGGAHTGELFF | TCRBV06 | 0.044248 | 0 |
| CASSFKNRIGTEAFF | TCRBV13-01*01 | 0.044248 | 0 |
| CASSFLLHMISTDTQYF | TCRBV05-06*01 | 0.265487 | 0 |
| CASSFRTSGIDTQYF | TCRBV28-00*01 | 0.044248 | 0 |
| CASSGGGSGSDTQYF | TCRB3V06-04 | 0.044248 | 0 |
| CASSIGLLEQFF | TCRBV07-02*01 | 0.044248 | 0 |
| CASSIVDPIIHHNSPLHF | TCRBV03 | 0.044248 | 0 |
| CASSIVGSWGSNQPQHF | TCRBV19-01 | 0.044248 | 0 |
| CASSKGHPFHTYNSPLHF | TCRBV03 | 0.044248 | 0 |
| CASSLDNSYEQYF | TCRBV07-06*01 | 0.044248 | 0 |
| CASSLDRAGQPQHF | TCRBV06 | 0.088496 | 0 |
| CASSLEAGSYNEQFF | TCRBV07-06*01 | 0.044248 | 0 |
| CASSLELASSYEQYF | TCRBV07-06*01 | 0.044248 | 0 |
| CASSLGAWWEQYF | TCRBV07-06*01 | 0.044248 | 0 |
| CASSLGLGYYGYTF | TCRBV07-02*01 | 0.044248 | 0 |
| CASSLGRGLEQYF | TCRBV07-07*01 | 0.044248 | 0 |
| CASSLGRWERGETQYF | TCRBV09-01 | 0.044248 | 0 |
| CASSLGVDGLAYEQYF | TCRBV07-02*01 | 0.044248 | 0 |
| CASSLGVSPTDTQYF | TCRBV07-09 | 0.044248 | 0 |
| CASSLLGNSYNEQFF | TCRBV27-01*01 | 0.044248 | 0 |
| CASSLPPTGQETQYF | TCRBV07-02*01 | 0.044248 | 0 |
| CASSLSRGARTYEQYF | TCRBV27-01*01 | 0.044248 | 0 |
| CASSLVVESYEQYF | TCRBV07-09 | 0.044248 | 0 |
| CASSPDFGRLSYEQYF | TCRBV27-01*01 | 0.044248 | 0 |
| CASSPFGRGQDTQYF | TCRBV11-02*02 | 0.088496 | 0 |
| CASSPGETYEQYF | TCRBV06 | 0.176991 | 0 |
| CASSPGGQPFGYEQYF | TCRBV09-01 | 0.044248 | 0 |
| CASSPGISEQYF | TCRBV04-02*01 | 0.044248 | 0 |
| CASSPPGGVKEKLFF | TCRBV04-01*01 | 0.044248 | 0 |
| CASSPPNTGELFF | TCRBV07-07*01 | 0.088496 | 0 |
| CASSPRGTEAFF | TCRBV06 | 0.044248 | 0 |
| CASSPRTRGGGLNEQFF | TCRBV07-03*01 | 0.044248 | 0 |
| CASSPSGGLYF | TCRBV06 | 0.044248 | 0 |
| CASSPSGGNNYEQYF | TCRBV28-01*01 | 0.044248 | 0 |
| CASSPSPGQLTYEQYF | TCRBV28-01*01 | 0.088496 | 0 |
| CASSPWTGSEQYF | TCRBV05-08*01 | 0.088496 | 0 |

TABLE 2 -continued

Clonotypes detected in pentamer-sorted T cells
(Table discloses SEQ ID NOS 14-223, respectively, in order of appearance)

| CDR3 Amino Add Sequence* | Vβ Gene | CDR3 Frequency in EBV EBNA 4NP pMHC + sort #1 | CDR3 Frequency In EBV EBNA 4NP pMHC + sort #2 |
|---|---|---|---|
| CASSQAAGDQPQHF | TCRBV03 | 0.044248 | 0 |
| CASSQDLRGTRKNIQYF | TCRBV11-02*02 | 0.044248 | 0 |
| CASSQGRDAYEQYF | TVRBV04-03*01 | 0.044248 | 0 |
| CASSQKRDYEQYF | TCRBV19-01 | 0.044248 | 0 |
| CASSQLTSGDYNEQFF | TCRBV04-03*01 | 0.088496 | 0 |
| CASSQRDPNSPLHF | TCRBV14-01*01 | 0.044248 | 0 |
| CASSRAIATIRTEAFF | TCRBV21-01*01 | 0.088496 | 0 |
| CASSRGRGDGRTIYF | TCRBV14-01*01 | 0.044248 | 0 |
| CASSRKTVLNTEAFF | TCRBV04-03*01 | 0.044248 | 0 |
| CASSRVGQSYEQYF | TCRBV12 | 0.044248 | 0 |
| CASSSFRVHLYEQYF | TCTBV28-01*01 | 0.044248 | 0 |
| CASSSLRGGLTNTGELFF | TCRBV07-07*01 | 0.044248 | 0 |
| CASSSNHPQSRANVLTF | TCRBV07-08*01 | 0.088496 | 0 |
| CASSSQTSGSWTGELFF | TCRBV07-06*01 | 0.044748 | 0 |
| CASSSSISGPRSIYF | TCRBV05-06*01 | 0.044248 | 0 |
| CASSSSQSRANVLTF | TCRBV07-04*01 | 0.044248 | 0 |
| CASSSTGGTDTQYF | TCRBV07-07*01 | 0.044248 | 0 |
| CASSSTGVGETQYF | TCRBV06-05*01 | 0.044248 | 0 |
| CASSSTLAGYEQYV | TCRBV14-01*01 | 0.044248 | 0 |
| CASSSTSGLAKNIQYF | TCRBV07-09 | 0.044248 | 0 |
| CASSSVRGIQPPLHF | TCRBV11-02*02 | 0.309735 | 0 |
| CASSSVRGTQPPLHF | TCRBV11-02*02 | 0.044248 | 0 |
| CASSTLDRGVAGYTF | TCRBV27-01*01 | 0.884956 | 0 |
| CASSVAGAGELFF | TCRBV09-01 | 0.044248 | 0 |
| CASSVGGDQPQHF | TCRBV09-01 | 0.044248 | 0 |
| CASSVGVGVSGNTIYF | TCRBV09-01 | 0.044248 | 0 |
| CASSWAGGINEQFF | TCRBV12 | 0.044248 | 0 |
| CASSWDGNEAFF | TCRBV13-01*01 | 0.044248 | 0 |
| CASSYDRTGADTEAFF | TCRBV06 | 0.044248 | 0 |
| CASSYMGSGANVLTF | TCRBV06-05*01 | 0.044248 | 0 |
| CASSYSGRISRGYTS | TCRBV06-05*01 | 0.044248 | 0 |
| CASSYSRPGSGRAKDTQYF | TCRBV06 | 0.044248 | 0 |
| CASSYTRMPPTFNEKLFF | TCRBV06-09*01 | 0.088496 | 0 |
| CASTGGNRGVNEQFF | TCRBV25-01*01 | 0.39823 | 0 |
| CASTGGNRGVNERFF | TCRBV25-01*01 | 0.044248 | 0 |
| CASTLSQLGPLYYEQYF | TCRBV04-01*01 | 0.044248 | 0 |
| CASTPDRAVWNTEAFF | TCRBV09-01 | 0.044248 | 0 |

TABLE 2 -continued

Clonotypes detected in pentamer-sorted T cells
(Table discloses SEQ ID NOS 14-223, respectively, in order of appearance)

| CDR3 Amino Add Sequence* | Vβ Gene | CDR3 Frequency in EBV EBNA 4NP pMHC + sort #1 | CDR3 Frequency In EBV EBNA 4NP pMHC + sort #2 |
|---|---|---|---|
| CASTPGMGGYYEQYF | TCRBV09-01 | 0.044248 | 0 |
| CASTSGTANNEQFF | TCRBV27-01*01 | 0.044248 | 0 |
| CASTYGSGDYEQYF | TCRBV19-01 | 0.044248 | 0 |
| CATSAPGGYNEQFF | TCRBV24 | 0.044248 | 0 |
| CATSDSLAKNIQYF | TCRBV24 | 0.044248 | 0 |
| CATSDSQVLAGLNQETQYF | TCRBV24 | 0.044248 | 0 |
| CATSGYRELAFF | TCRBV15-01*01 | 0.044248 | 0 |
| CATSRDPLQEQFF | TCRBV15-01*01 | 0.088496 | 0 |
| CATSRDSNNEQFF | TCRBV15-01*01 | 0.044248 | 0 |
| CATSRDYEQYF | TCRBV15-01*01 | 0.044248 | 0 |
| CATSRGLAGGFEQFF | TCRBV15-01*01 | 0.044248 | 0 |
| CATSSLLASPNEQFF | TCRBV15-01*01 | 0.442478 | 0 |
| CAWGDMIRSQYF | TCRBV30-01*01 | 0.044248 | 0 |
| CAWSEDRDEQYF | TCRBV30-01*01 | 0.044248 | 0 |
| CAWSERDGGEQFF | TCRBV30-01*01 | 0.044248 | 0 |
| CAWSGDAGGYTLHF | TCRBV30-01*01 | 0.044248 | 0 |
| CAWSPGTGSQYF | TCRBV30-01*01 | 0.088496 | 0 |
| CAWTRTDTQYF | TCRBV30-01*01 | 0.044248 | 0 |
| CSAAPSGYSPLHF | TCRBV20 | 0.044248 | 0 |
| CSAGGQGSYSYGYTF | TCRBV29-01*01 | 0.044248 | 0 |
| CSAHLIGGRYNEQFF | TCRBV20 | 0.044248 | 0 |
| CSARDNRAEISPLHF | TCRBV20 | 0.044248 | 0 |
| CSARDQDEKLFF | TCRBV20 | 0.088496 | 0 |
| CSARDQGQHAPYEQYF | TCRBV20 | 0.044248 | 0 |
| CSARGLAGGGQFF | TCRBV20 | 0.044248 | 0 |
| CSARNRVNTGELFF | TCRBV20 | 0.044248 | 0 |
| CSARQLPYGYTF | TCRBV20 | 0.044248 | 0 |
| CSARVGVNQPQHF | TCRBV20 | 0.044248 | 0 |
| CSARVMTSGSMRETQYF | TCRBV20 | 0.265487 | 0 |
| CSARATMTSRSMREAQYF | TCRBV20 | 0.044248 | 0 |
| CSASEAAGANVLTF | TCRBV20 | 0.044248 | 0 |
| CSASPGTSTQTQYF | TCRBV20 | 0.044248 | 0 |
| CSASVTGTAYEQYF | TCRBV20 | 0.044248 | 0 |
| CSVAVTGTGEQYF | TCRBV29-01*01 | 0.044248 | 0 |
| CSVERGTEAFF | TCRBV29-01*01 | 0.044248 | 0 |
| CSVGPGLASPLHF | TCRBV29-01*01 | 0.088496 | 0 |
| CSVSGRSYNEQFF | TCRBV29-01*01 | 0.044248 | 0 |
| CSVTGTDYSYEQYF | TCRBV29-01*01 | 0.044248 | 0 |

TABLE 2 -continued

Clonotypes detected in pentamer-sorted T cells
(Table discloses SEQ ID NOS 14-223, respectively, in order of appearance)

| CDR3 Amino Add Sequence* | Vβ Gene | CDR3 Frequency in EBV EBNA 4NP pMHC + sort #1 | CDR3 Frequency In EBV EBNA 4NP pMHC + sort #2 |
|---|---|---|---|
| CSVVQGAGYTF | TCRBV29-01*01 | 0.088496 | 0 |
| RASSGADSNSPLHF | TCRBV03 | 0.044248 | 0 |

*Bolded clonotypes
were positive by FEST analysis

TABLE 3

Candidate MANAs tested by MANAFEST is patient JH124

| Candidate MANA ID | Candidate MANA Amino Acid Sequence | SEQ ID NO | Predicted HLA Restriction | Gene Symbol | % mutant reads | Candidate MANA Predicted MHC Class I Affinity | Candidate MANA Affinity % Rank | Candidate MANA Binding Classification |
|---|---|---|---|---|---|---|---|---|
| MANA 2 | HVIENIYF | 224 | HLA-A*25:01 | OPA1 | 46% | 171.5 | 0.1 | SB |
| MANA 3 | DVAAHLQPL | 225 | HLA-A*25:01 | HMGXB4 | 35% | 185 | 0.1 | SB |
| MANA 4 | ETPNLDLM | 226 | HLA-A*25:01 | GALNS | 73% | 1085.7 | 0.5 | SB |
| MANA 5 | SVFNTWNPM | 227 | HLA-A*25:01 | PLEK | 49% | 738 | 0.3 | SB |
| MANA 5 | SVFNTWNPM | 227 | HLA-C*12:03 | PLEK | 49% | 21.6 | 0.3 | SB |
| MANA 6 | EVQQFLRY | 228 | HLA-A*25:01 | LARGE | 38% | 665.3 | 0.3 | SB |
| MANA 7 | EVIVPLSGW | 229 | HLA-A*25:01 | ARVCF | 39% | 339.7 | 0.17 | SB |
| MANA 8 | ETMQCSELY | 230 | HLA-A*25:01 | KLHL29 | 79% | 85.2 | 0.05 | SB |
| MANA 9 | ETMQCSELYHM | 231 | HLA-A*25:01 | KLHL29 | 79% | 208.9 | 0.12 | SB |
| MANA 10 | ETMQCSEL | 232 | HLA-A*25:01 | KLHL29 | 79% | 773.2 | 0.4 | SB |
| MANA 18 | ITRTVSANTV | 233 | HLA-A*30:01 | TNC | 40% | 43.4 | 0.8 | SB |
| MANA 19 | ATKNNKVIMA | 234 | HLA-A*30:01 | PSMC5 | 36% | 28.4 | 0.5 | SB |
| MANA 20 | VAHFQLQMLK | 235 | HLA-A*30:01 | SLC4A2 | 25% | 49.5 | 1 | SB |
| MANA 23 | EEDTFSYLI | 236 | HLA-B*38:01 | ANKLE2 | 44% | 1421.3 | 0.5 | SB |
| MANA 24 | AHFQLQML | 237 | HLA-B*38:01 | SLC4A2 | 25% | 628.5 | 0.25 | SB |
| MANA 24 | AHFQLQML | 237 | HLA-B*39:01 | SLC4A2 | 25% | 83.9 | 0.4 | SB |
| MANA 25 | LHAMIQAAGKL | 238 | HLA-B*38:01 | CHD6 | 34% | 777.4 | 0.3 | SB |
| MANA 26 | LHEAQPWFEFL | 239 | HLA-B*38:01 | SPG11 | 31% | 517.6 | 0.2 | SB |

TABLE 3-continued

| Candidate MANAs tested by MANAFEST is patient JH124 | | | | | | | | |
|---|---|---|---|---|---|---|---|---|
| MANA 27 | LHEAQPWFEF | 240 | HLA-B*38:01 | SPG11 | 31% | 822.9 | 0.3 | SB |
| MANA 28 | EHLSCPDNFL | 241 | HLA-B*38:01 | ATG5 | 33% | 583.5 | 0.25 | SB |
| MANA 29 | NHARIDAAKV | 242 | HLA-B*38:01 | CDKN2A | 67% | 1323.2 | 0.5 | SB |
| MANA 30 | QHQPNPFEV | 243 | HLA-B*38:01 | SGK223 | 54% | 978.5 | 0.4 | SB |
| MANA 33 | TQLEKEAL | 244 | HLA-B*39:01 | NIN | 70% | 106 | 0.5 | SB |
| MANA 34 | TRARNEYLLSL | 245 | HLA-B*39:01 | ARHGAP 4 | 23% | 56.4 | 0.25 | SB |
| MANA 35 | NPMWVVLL | 246 | HLA-B*39:01 | PLEK | 49% | 60.8 | 0.3 | SB |
| MANA 36 | KHILVWAL | 247 | HLA-B*39:01 | C22orf39 | 14% | 81.4 | 0.4 | SB |
| MANA 36 | KHILVWAL | 247 | HLA-B*38:01 | C22orf39 | 14% | 406.1 | 0.17 | SB |
| MANA 37 | SQSDYIPM | 248 | HLA-B*39:01 | GAB2 | 39% | 44.4 | 0.2 | SB |
| MANA 38 | VHDYFSVI | 249 | HLA-B*39:01 | SACS | 14% | 114.7 | 0.5 | SB |
| MANA 43 | IYFPAAQTM | 250 | HLA-C*12:03 | OPAI | 46% | 18.6 | 0.25 | SB |
| MANA 44 | FSYLIWSNPRY | 251 | HLA-C*12:03 | ANKLE2 | 44% | 32.8 | 0.5 | SB |
| MANA 45 | YSWSAQRQAL | 252 | HLA-C*12:03 | GAK | 18% | 39.2 | 0.8 | SB |
| MANA 46 | FAVWTLAETI | 253 | HLA-C*12:03 | IPO4 | 39% | 17.4 | 0.2 | SB |
| MANA 47 | FASLALARRYL | 254 | HLA-C*12:03 | TMEM64 | 45% | 17.1 | 0.2 | SB |
| MANA 48 | DVIQQDELDSY | 255 | HLA-A*25:01 | PVRL3 | 39% | 151 | 0.1 | SB |
| MANA 49 | KNRSSGTVSA | 256 | HLA-A*30:01 | HBP1 | 24% | 27.5 | 0.5 | SB |
| MANA 50 | KLKRFNLSA | 257 | HLA-A*30:01 | APEH | 48% | 8.6 | 0.1 | SB |
| MANA 51 | KSFAVWTLA | 258 | HLA-A*30:01 | IPO4 | 39% | 23.6 | 0.4 | SB |
| MANA 52 | KWRLSLCTV | 259 | HLA-A*30:01 | C3orf17 | 44% | 31.6 | 0.8 | SB |
| MANA 53 | RSRPVAATAK | 260 | HLA-A*30:01 | IQCB1 | 45% | 3 | 0.01 | SB |
| MANA 54 | RSRPVAATA | 261 | HLA-A*30:01 | IQCB1 | 45% | 4.8 | 0.03 | SB |
| MANA 55 | TAKQAHLTTL K | 262 | HLA-A*30:01 | IQCB1 | 45% | 33.6 | 0.8 | SB |
| MANA 56 | SHCPSAMGI | 263 | HLA-B*38:01 | NFKBIL1 | 47% | 925.8 | 0.4 | SB |
| MANA 57 | FHASEGWL | 264 | HLA-B*39:01 | CENPBD 1 | 75% | 54.5 | 0.25 | SB |

TABLE 3-continued

Candidate MANAs tested by MANAFEST is patient JH124

| | | | | | | | | |
|---|---|---|---|---|---|---|---|---|
| MANA 58 | THEVIVPL | 265 | HLA-B*39:01 | ARVCF | 39% | 42.5 | 0.2 | SB |
| MANA 59 | SRHCLQPL | 266 | HLA-B*39:01 | FRS3 | 43% | 58.5 | 0.25 | SB |
| MANA 60 | FASLALARRY . | 267 | HLA-C*12:03 | TMEM64 | 45% | 41.7 | 0.8 | SB |
| MANA 61 | SVFNTWNPMWV | 268 | HLA-C*12:03 | PLEK | 49% | 32.8 | 0.5 | SB |
| MANA 62 | LTHEVIVPL | 269 | HLA-C*12:03 | ARVCF | 39% | 36.7 | 0.5 | SB |
| MANA 63 | YTVMARKSPV | 270 | HLA-C*12:03 | RAD54L2 | 74% | 34.5 | 0.5 | SB |

| Candidate MANA ID | WT Amino Acid Sequence | SEQ ID NO | WT Predicted MHC Class I Affinity | WT Affinity % Rank | WT Binding Classification | Median Tumor Expression* |
|---|---|---|---|---|---|---|
| MANA 2 | HVIENIYL | 271 | 686.2 | 0.3 | SB | 2671.6 |
| MANA 3 | DVAAHLQLL | 272 | 551.1 | 0.25 | SB | 857.6 |
| MANA 4 | ETPNLDRM | 273 | 1796.9 | 0.8 | WB | 779.5 |
| MANA 5 | SVFNTWKPM | 274 | 2722 | 1 | WB | 516.3 |
| MANA 5 | SVFNTWKPM | 274 | 56.3 | 0.8 | WB | 516.3 |
| MANA 6 | EAQQFLRY | 275 | 3442.6 | 1.5 | WB | 365.8 |
| MANA 7 | EVIVPHSGW | 276 | 1530.2 | 0.8 | WB | 253.7 |
| MANA 8 | EAMQCSELY | 277 | 900.2 | 0.4 | SB | 207.2 |
| MANA 9 | EAMQCSELYHM | 278 | 2362.4 | 0.8 | WB | 207.2 |
| MANA 10 | EAMQCSEL | 279 | 5586.5 | 2 | WB | 207.2 |
| MANA 18 | ITRTVSGNTV | 280 | 69.9 | 1.5 | WB | 6942.8 |
| MANA 19 | ATKNIKVIMA | 281 | 23.2 | 0.4 | SB | 2784.6 |
| MANA 20 | VAHFQRQMLK | 282 | 28.7 | 0.5 | SB | 1906.6 |
| MANA 23 | EEDTFSDLI | 283 | 2976.8 | 1 | WB | 1946.6 |
| MANA 24 | AHFQRQML | 284 | 1933 | 0.8 | WB | 1906.6 |
| MANA 24 | AHFQRQML | 284 | 129.8 | 0.8 | WB | 1906.6 |
| MANA 25 | LQAMIQAAGKL | 285 | 8269.3 | 4 | NB | 1380.9 |
| MANA 26 | LHEAHPWFEFL | 286 | 448.7 | 0.17 | SB | 1306 |
| MANA 27 | LHEAHPWFEF | 287 | 626.8 | 0.25 | SB | 1306 |
| MANA 28 | EHLSYPDNFL | 288 | 465.8 | 0.17 | SB | 998 |
| MANA 29 | NHARIDAAEG | 289 | 17959.6 | 15 | NB | 576.8 |

TABLE 3-continued

Candidate MANAs tested by MANAFEST is patient JH124

| | | | | | | |
|---|---|---|---|---|---|---|
| MANA 30 | LHQPNPFEV | 290 | 745.4 | 0.3 | SB | 542.1 |
| MANA 33 | TQQEKEAL | 291 | 162.7 | 0.8 | WB | 1078.6 |
| MANA 34 | TKARNEYLLSL | 292 | 142 | 0.8 | WB | 538.9 |
| MANA 35 | KPMWVVLL | 293 | 334.1 | 1.5 | WB | 516.3 |
| MANA 36 | KHILVWAP | 294 | 10929.7 | 15 | NB | 441.3 |
| MANA 36 | KHILVWAP | 294 | 19040.8 | 15 | NB | 441.3 |
| MANA 37 | SQSVYIPM | 295 | 127.9 | 0.8 | WB | 375.9 |
| MANA 38 | VHDDFSVI | 296 | 177.5 | 0.8 | WB | 358.2 |
| MANA 43 | IYLPAAQTM | 297 | 174.5 | 2 | WB | 2671.6 |
| MANA 44 | FSDLIWSNPRY | 298 | 833 | 6 | NB | 1946.6 |
| MANA 45 | YSWSAQRRAL | 299 | 30.5 | 0.4 | SB | 1492.1 |
| MANA 46 | FAVGTLAETI | 300 | 24.7 | 0.3 | SB | 1293.3 |
| MANA 47 | FASLALVRRYL | 301 | 19.2 | 0.25 | SB | 653 |
| MANA 48 | DVLQQDELDSY | 302 | 3171.1 | 1.5 | WB | 93.3 |
| MANA 49 | KNHSSGTVSA | 303 | 180.6 | 3 | WB | 1549.7 |
| MANA 50 | KLKSFNLSA | 304 | 9.3 | 0.12 | SB | 1448.6 |
| MANA 51 | KSFAVGTLA | 305 | 57 | 1 | WB | 1293.3 |
| MANA 52 | KWRLSHCTV | 306 | 22.8 | 0.4 | SB | 1213.3 |
| MANA 53 | RSRPVAAKAK | 307 | 4.1 | 0.03 | SB | 722.9 |
| MANA 54 | RSRPVAAKA | 308 | 5.3 | 0.05 | SB | 722.9 |
| MANA 55 | KAKQAHLTTLK | 309 | 4.8 | 0.03 | SB | 722.9 |
| MANA 56 | SRCPSAMGI | 310 | 15334.5 | 9 | NB | 400.2 |
| MANA 57 | FHASQGWL | 311 | 31.9 | 0.12 | SB | 292.7 |
| MANA 58 | THEVIVPH | 312 | 9995.6 | 15 | NB | 253.7 |
| MANA 59 | GRHCLQPL | 313 | 365.5 | 1.5 | WB | 120.4 |
| MANA 60 | FASLALVRRY | 314 | 32.8 | 0.5 | SB | 653 |

TABLE 3-continued

| Candidate MANAs tested by MANAFEST is patient JH124 | | | | | | |
|---|---|---|---|---|---|---|
| MANA 61 | SVFNTWKPMWV | 315 | 71 | 1 | WB | 516.3 |
| MANA 62 | LTHEVIVPH | 316 | 747.9 | 6 | NB | 253.7 |
| MANA 63 | VYRYGQKKPC | 317 | 38060.3 | 50 | NB | 172.4 |

TABLE 4

| | positive_clones | sum_freq |
|---|---|---|
| JH124_04 | 1 | 2.737226 |
| JH124_07 | 2 | 8.590604 |
| JH124_08 | 1 | 6.757391 |
| JH124_09 | 1 | 6.359032 |
| JH124_18 | 1 | 1.067236 |
| JH124_25 | 1 | 1.070579 |
| JH124_28 | 1 | 0.804455 |
| JH124_30 | 3 | 3.697834 |
| JH124_33 | 1 | 0.705581 |
| JH124_34 | 1 | 3.039874 |
| JH124_35 | 1 | 2.122642 |

TABLE 4-continued

| | positive_clones | sum_freq |
|---|---|---|
| JH124_46 | 1 | 2.004008 |
| JH124_51 | 1 | 0.668449 |
| JH124_52 | 3 | 6.909895 |
| JH124_53 | 1 | 3.774238 |
| JH124_54 | 1 | 0.74206 |
| JH124_55 | 1 | 4.546692 |
| JH124_57 | 1 | 0.755192 |
| JH124_58 | 1 | 3.218391 |
| JH124_59 | 2 | 6.101104 |
| JH124_63 | 2 | 2.952381 |

TABLE 5

| | SEQ ID NO | Condition | JH124 baseline percent | FC: JH124 baseline | JH124_NoPep percent | FC: JH124 NoPep |
|---|---|---|---|---|---|---|
| CASSGQGGVSEKLFF | 318 | JH124_04 | 0 | 29 | 0 | 34 |
| CASSLTGGYTGELFF | 319 | JH124_07 | 0.093458 | 53 | 0.079365 | 62 |
| CASSLRSSSETQYF | 320 | JH124_07 | 0 | 39 | 0 | 46 |
| CASSLQAGSSYNEQFF | 321 | JH124_63 | 0 | 23 | 0 | 28 |
| CASSPSGGSLYNEQFF | 322 | JH124_63 | 0 | 8 | 0 | 10 |
| CASSGGISNTEAFF | 323 | JH124_35 | 0 | 23 | 0 | 27 |
| CATSTLPSGGEGYEQYF | 324 | JH124_54 | 0.186916 | 4 | 0 | 9 |
| CASSGTTYGYTF | 325 | JH124_09 | 0 | 68 | 0 | 80 |
| CSASRGLSGYTF | 326 | JH124_53 | 0 | 40 | 0 | 48 |
| LGPGTFTSYEQYF | 327 | JH124_28 | 0 | 9 | 0 | 10 |
| CASSTGTGFGEQYF | 328 | JH124_57 | 0 | 8 | 0 | 10 |
| CASSEGGSDEQYF | 329 | JH124_25 | 0 | 11 | 0 | 13 |
| CASSLDPRSSYNSPLHF | 330 | JH124_33 | 0 | 8 | 0 | 9 |
| CASTAGTVHSNQPQHF | 331 | JH124_55 | 0 | 49 | 0 | 57 |
| CASRDTRELNTEAFF | 332 | JH124_59 | 0 | 34 | 0 | 40 |
| CASSLGDLRGFTEAFF | 333 | JH124_59 | 0 | 31 | 0.15873 | 18 |
| CATSDLVARDEQFF | 334 | JH124_18 | 0 | 11 | 0 | 13 |
| CASSYRGTGGGGYTF | 335 | JH124_08 | 0 | 72 | 0 | 85 |
| CASSLQGGMGNQPQHF | 336 | JH124_30 | 0 | 22 | 0 | 26 |
| CASSLGLGDEQFF | 337 | JH124_30 | 0 | 11 | 0 | 13 |
| CASFRQVNYGYTF | 338 | JH124_30 | 0 | 7 | 0 | 8 |
| CASSFRQGSYEQYF | 339 | JH124_46 | 0 | 21 | 0 | 25 |

TABLE 5-continued

| | SEQ ID NO | Condition | JH124 baseline percent | FC: JH124 baseline | JH124_NoPep percent | FC: JH124 NoPep |
|---|---|---|---|---|---|---|
| CASSPDIQYF | 340 | JH124_51 | 0 | 7 | 0 | 8 |
| CASSETGWGAFF | 341 | JH124_34 | 0.186916 | 16 | 0.238095 | 13 |
| CASRRHSNQPQHF | 342 | JH124_52 | 0 | 46 | 0 | 55 |
| CASSLVGLAGNEQFF | 343 | JH124_52 | 0 | 19 | 0 | 22 |
| CASSPQDQHVYEQYF | 344 | JH124_52 | 0 | 9 | 0 | 10 |
| CASTLRVDTEAFF | 345 | JH124_58 | 0 | 34 | 0 | 41 |

TABLE 6

| | condition | JH124_PBMC_ 68w_ abundance | JH124 Base line abundance | JH124_PBMC_ 64w_ abundance | JH124_NoPep abundance | JH124_10_ abundance |
|---|---|---|---|---|---|---|
| CASSGQGGVSEKLFF (SEQ ID NO: 318) | JH124_04 | 0 | 0 | 0 | 0 | 0 |
| CASSLTGGYTGELFF (SEQ ID NO: 319) | JH124_07 | 1 | 1 | 0 | 1 | 0 |
| CASSLRSSSETQYF (SEQ ID NO: 320) | JH124_07 | 0 | 0 | 0 | 0 | 0 |
| CASSLQAGSSYNEQFF (SEQ ID NO: 321) | JH124_63 | 0 | 0 | 0 | 0 | 0 |
| CASSPSGGSLYNEQFF (SEQ ID NO: 322) | JH124_63 | 0 | 0 | 0 | 0 | 0 |
| CASSGGISNTEAFF (SEQ ID NO: 323) | JH124_35 | 0 | 0 | 0 | 0 | 0 |
| CATSTLPSGGEGYEQYF (SEQ ID NO: 324) | JH124_54 | 0 | 2 | 0 | 0 | 0 |
| CASSGTTYGYTF (SEQ ID NO: 325) | JH124_09 | 4 | 0 | 11 | 0 | 0 |
| CSASRGLSGYTF (SEQ ID NO: 326) | JH124_53 | 0 | 0 | 0 | 0 | 0 |
| LGPGTFTSYEQYF (SEQ ID NO: 327) | JH124_28 | 0 | 0 | 2 | 0 | 0 |
| CASSTGTGFGEQYF (SEQ ID NO: 328) | JH124_57 | 0 | 0 | 0 | 0 | 0 |
| CASSEGGSDEQYF (SEQ ID NO: 329) | JH124_25 | 0 | 0 | 0 | 0 | 0 |
| CASSLDPRSSYNSPLHF (SEQ ID NO: 330) | JH124_33 | 0 | 0 | 0 | 0 | 0 |
| CASTAGTVHSNQPQHF (SEQ ID NO: 331) | JH124_55 | 0 | 0 | 0 | 0 | 0 |
| CASRDTRELNTEAFF (SEQ ID NO: 332) | JH124_59 | 0 | 0 | 0 | 0 | 0 |
| CASSLGDLRGFTEAFF (SEQ ID NO: 333) | JH124_59 | 0 | 0 | 0 | 2 | 0 |

TABLE 6-continued

| | | | | | | |
|---|---|---|---|---|---|---|
| CATSDLVARDEQFF (SEQ ID NO: 334) | JH124_18 | 0 | 0 | 0 | 0 | 0 |
| CASSYRGTGGGGYTF (SEQ ID NO: 335) | JH124_08 | 1 | 0 | 0 | 0 | 0 |
| CASSLQGGMGNQPQHF (SEQ ID NO: 336) | JH124_30 | 2 | 0 | 1 | 0 | 0 |
| CASSLGLGDEQFF (SEQ ID NO: 337) | JH124_30 | 0 | 0 | 1 | 0 | 0 |
| CASFRQVNYGYTF (SEQ ID NO: 338) | JH124_30 | 0 | 0 | 0 | 0 | 0 |
| CASSFRQGSYEQYF (SEQ ID NO: 339) | JH124_46 | 0 | 0 | 0 | 0 | 0 |
| CASSPDIQYF (SEQ ID NO: 340) | JH124_51 | 0 | 0 | 0 | 0 | 0 |
| CASSETGWGAFF (SEQ ID NO: 341) | JH124_34 | 8 | 2 | 27 | 3 | 0 |
| CASRRHSNQPQHF (SEQ ID NO: 342) | JH124_52 | 0 | 0 | 0 | 0 | 0 |
| CASSLVGLAGNEQFF (SEQ ID NO: 343) | JH124_52 | 0 | 0 | 0 | 0 | 0 |
| CASSPQDQHVYEQYF (SEQ ID NO: 344) | JH124_52 | 0 | 0 | 0 | 0 | 0 |
| CASTLRVDTEAFF (SEQ ID NO: 345) | JH124_58 | 0 | 0 | 0 | 0 | 0 |

| | condition | JH124_49 abundance | JH124_50 abundance | JH124_04_ abundance | JH124_07_ abundance | JH124_19_ abundance | JH124_05_ abundance | JH124_27_ abundance |
|---|---|---|---|---|---|---|---|---|
| CASSGQGGVSEKLFF (SEQ ID NO: 318) | JH124_04 | 0 | 0 | 60 | 0 | 0 | 0 | 0 |
| CASSLTGGYTGELFF (SEQ ID NO: 319) | JH124_07 | 1 | 2 | 0 | 110 | 0 | 4 | 0 |
| CASSLRSSSETQYF (SEQ ID NO: 320) | JH124_07 | 0 | 0 | 0 | 82 | 0 | 0 | 0 |
| CASSLQAGSSYNEQFF (SEQ ID NO: 321) | JH124_63 | 0 | 0 | 0 | 0 | 0 | 0 | 0 |

TABLE 6-continued

| | | | | | | | | |
|---|---|---|---|---|---|---|---|---|
| CASSPSGGSLYNEQFF (SEQ ID NO: 322) | JH124_63 | 0 | 0 | 0 | 0 | 0 | 0 | 0 |
| CASSGGISNTEAFF (SEQ ID NO: 323) | JH124_35 | 0 | 0 | 0 | 0 | 1 | 0 | 0 |
| CATSTLPSGGEGYEQYF (SEQ ID NO: 324) | JH124_54 | 0 | 0 | 0 | 0 | 0 | 0 | 0 |
| CASSGTTYGYTF (SEQ ID NO: 325) | JH124_09 | 0 | 0 | 0 | 0 | 0 | 0 | 0 |
| CSASRGLSGYTF (SEQ ID NO: 326) | JH124_53 | 0 | 0 | 0 | 0 | 0 | 0 | 0 |
| LGPGTFTSYEQYF (SEQ ID NO: 327) | JH124_28 | 0 | 0 | 0 | 0 | 0 | 0 | 0 |
| CASSTGTGFGEQYF (SEQ ID NO: 328) | JH124_57 | 0 | 0 | 0 | 0 | 0 | 0 | 0 |
| CASSEGGSDEQYF (SEQ ID NO: 329) | JH124_25 | 0 | 0 | 0 | 0 | 0 | 0 | 0 |
| CASSLDPRSSYNSPLHF (SEQ ID NO: 330) | JH124_33 | 0 | 0 | 0 | 0 | 0 | 0 | 0 |
| CASTAGTVHSNQPQHF (SEQ ID NO: 331) | JH124_55 | 0 | 0 | 0 | 0 | 0 | 0 | 0 |
| CASRDTRELNTEAFF (SEQ ID NO: 332) | JH124_59 | 0 | 0 | 0 | 0 | 0 | 0 | 0 |
| CASSLGDLRGFTEAFF (SEQ ID NO: 333) | JH124_59 | 0 | 0 | 0 | 0 | 0 | 0 | 0 |
| CATSDLVARDEQFF (SEQ ID NO: 334) | JH124_18 | 0 | 0 | 0 | 0 | 0 | 0 | 0 |
| CASSYRGTGGGGYTF (SEQ ID NO: 335) | JH124_08 | 0 | 0 | 0 | 0 | 0 | 0 | 0 |
| CASSLQGGMGNQPQHF (SEQ ID NO: 336) | JH124_30 | 0 | 1 | 0 | 3 | 0 | 0 | 0 |
| CASSLGLGDEQFF (SEQ ID NO: 337) | JH124_30 | 0 | 0 | 0 | 0 | 0 | 0 | 0 |
| CASFRQVNYGYTF (SEQ ID NO: 338) | JH124_30 | 0 | 0 | 0 | 0 | 0 | 0 | 0 |
| CASSFRQGSYEQYF (SEQ ID NO: 339) | JH124_46 | 0 | 0 | 0 | 0 | 0 | 0 | 0 |

TABLE 6-continued

| | | | | | | | | |
|---|---|---|---|---|---|---|---|---|
| CASSPDIQYF (SEQ ID NO: 340) | JH124_51 | 0 | 0 | 0 | 0 | 0 | 0 | 0 |
| CASSETGWGAFF (SEQ ID NO: 341) | JH124_34 | 1 | 4 | 0 | 0 | 1 | 1 | 2 |
| CASRRHSNQPQHF (SEQ ID NO: 342) | JH124_52 | 0 | 0 | 0 | 0 | 0 | 0 | 0 |
| CASSLVGLAGNEQFF (SEQ ID NO: 343) | JH124_52 | 0 | 0 | 0 | 0 | 0 | 0 | 0 |
| CASSPQDQHVYEQYF (SEQ ID NO: 344) | JH124_52 | 0 | 0 | 0 | 0 | 0 | 0 | 0 |
| CASTLRVDTEAFF (SEQ ID NO: 345) | JH124_58 | 0 | 0 | 0 | 0 | 0 | 0 | 0 |

| | condition | JH124_63_ abundance | JH124_35_ abundance | JH124_54_ abundance | JH124_61_ abundance | JH124_09_ abundance | JH124_45_ abundance |
|---|---|---|---|---|---|---|---|
| CASSGQGGVSEKLFF (SEQ ID NO: 318) | JH124_04 | 0 | 0 | 0 | 0 | 0 | 0 |
| CASSLTGGYTGELFF (SEQ ID NO: 319) | JH124_07 | 4 | 1 | 2 | 1 | 2 | 4 |
| CASSLRSSSETQYF (SEQ ID NO: 320) | JH124_07 | 0 | 0 | 0 | 0 | 0 | 0 |
| CASSLQAGSSYNEQFF (SEQ ID NO: 321) | JH124_63 | 46 | 0 | 0 | 0 | 0 | 0 |
| CASSPSGGSLYNEQFF (SEQ ID NO: 322) | JH124_63 | 16 | 0 | 0 | 0 | 0 | 0 |
| CASSGGISNTEAFF (SEQ ID NO: 323) | JH124_35 | 0 | 54 | 0 | 0 | 0 | 0 |
| CATSTLPSGGEGYEQYF (SEQ ID NO: 324) | JH124_54 | 0 | 0 | 25 | 0 | 0 | 0 |
| CASSGTTYGYTF (SEQ ID NO: 325) | JH124_09 | 0 | 0 | 0 | 0 | 113 | 0 |
| CSASRGLSGYTF (SEQ ID NO: 326) | JH124_53 | 0 | 0 | 0 | 0 | 0 | 0 |
| LGPGTFTSYEQYF (SEQ ID NO: 327) | JH124_28 | 0 | 0 | 0 | 0 | 0 | 0 |

TABLE 6-continued

| | | | | | | | |
|---|---|---|---|---|---|---|---|
| CASSTGTGFGEQYF (SEQ ID NO: 328) | JH124_57 | 0 | 0 | 0 | 0 | 0 | 0 |
| CASSEGGSDEQYF (SEQ ID NO: 329) | JH124_25 | 0 | 0 | 0 | 0 | 0 | 0 |
| CASSLDPRSSYNSPLHF (SEQ ID NO: 330) | JH124_33 | 0 | 0 | 0 | 0 | 0 | 0 |
| CASTAGTVHSNQPQHF (SEQ ID NO: 331) | JH124_55 | 0 | 0 | 3 | 0 | 0 | 0 |
| CASRDTRELNTEAFF (SEQ ID NO: 332) | JH124_59 | 0 | 0 | 0 | 0 | 0 | 0 |
| CASSLGDLRGFTEAFF (SEQ ID NO: 333) | JH124_59 | 0 | 0 | 0 | 0 | 0 | 0 |
| CATSDLVARDEQFF (SEQ ID NO: 334) | JH124_18 | 0 | 0 | 0 | 0 | 0 | 8 |
| CASSYRGTGGGGYTF (SEQ ID NO: 335) | JH124_08 | 0 | 0 | 0 | 0 | 0 | 0 |
| CASSLQGGMGNQPQHF (SEQ ID NO: 336) | JH124_30 | 0 | 0 | 1 | 0 | 0 | 0 |
| CASSLGLGDEQFF (SEQ ID NO: 337) | JH124_30 | 0 | 1 | 0 | 0 | 0 | 0 |
| CASFRQVNYGYTF (SEQ ID NO: 338) | JH124_30 | 0 | 0 | 0 | 0 | 0 | 0 |
| CASSFRQGSYEQYF (SEQ ID NO: 339) | JH124_46 | 0 | 0 | 0 | 0 | 0 | 0 |
| CASSPDIQYF (SEQ ID NO: 340) | JH124_51 | 0 | 0 | 0 | 0 | 0 | 0 |
| CASSETGWGAFF (SEQ ID NO: 341) | JH124_34 | 0 | 0 | 0 | 0 | 1 | 1 |
| CASRRHSNQPQHF (SEQ ID NO: 342) | JH124_52 | 0 | 0 | 0 | 0 | 0 | 0 |
| CASSLVGLAGNEQFF (SEQ ID NO: 343) | JH124_52 | 0 | 0 | 0 | 0 | 0 | 0 |
| CASSPQDQHVYEQYF (SEQ ID NO: 344) | JH124_52 | 0 | 0 | 0 | 0 | 0 | 0 |
| CASTLRVDTEAFF (SEQ ID NO: 345) | JH124_58 | 0 | 0 | 0 | 0 | 0 | 0 |

TABLE 6-continued

| | condition | JH124_53_ abundance | JH124_06_ abundance | JH124_28_ abundance | JH124_36_ abundance | JH124_47_ abundance | JH124_62_ abundance |
|---|---|---|---|---|---|---|---|
| CASSGQGGVSEKLFF (SEQ ID NO: 318) | JH124_04 | 0 | 0 | 0 | 0 | 0 | 0 |
| CASSLTGGYTGELFF (SEQ ID NO: 319) | JH124_07 | 0 | 0 | 1 | 0 | 3 | 0 |
| CASSLRSSSETQYF (SEQ ID NO: 320) | JH124_07 | 0 | 0 | 0 | 0 | 0 | 0 |
| CASSLQAGSSYNEQFF (SEQ ID NO: 321) | JH124_63 | 0 | 0 | 0 | 0 | 0 | 0 |
| CASSPSGGSLYNEQFF (SEQ ID NO: 322) | JH124_63 | 0 | 0 | 0 | 0 | 0 | 0 |
| CASSGGISNTEAFF (SEQ ID NO: 323) | JH124_35 | 0 | 0 | 0 | 0 | 0 | 0 |
| CATSTLPSGGEGYEQYF (SEQ ID NO: 324) | JH124_54 | 0 | 0 | 0 | 0 | 0 | 0 |
| CASSGTTYGYTF (SEQ ID NO: 325) | JH124_09 | 0 | 0 | 2 | 0 | 0 | 0 |
| CSASRGLSGYTF (SEQ ID NO: 326) | JH124_53 | 109 | 0 | 0 | 0 | 0 | 0 |
| LGPGTFTSYEQYF (SEQ ID NO: 327) | JH124_28 | 0 | 0 | 13 | 0 | 0 | 0 |
| CASSTGTGFGEQYF (SEQ ID NO: 328) | JH124_57 | 0 | 0 | 0 | 0 | 0 | 0 |
| CASSEGGSDEQYF (SEQ ID NO: 329) | JH124_25 | 0 | 0 | 0 | 0 | 0 | 0 |
| CASSLDPRSSYNSPLHF (SEQ ID NO: 330) | JH124_33 | 0 | 0 | 0 | 0 | 0 | 0 |
| CASTAGTVHSNQPQHF (SEQ ID NO: 331) | JH124_55 | 0 | 0 | 0 | 0 | 0 | 0 |
| CASRDTRELNTEAFF (SEQ ID NO: 332) | JH124_59 | 0 | 0 | 0 | 0 | 0 | 0 |
| CASSLGDLRGFTEAFF (SEQ ID NO: 333) | JH124_59 | 0 | 0 | 0 | 0 | 0 | 0 |

TABLE 6-continued

| | | | | | | | |
|---|---|---|---|---|---|---|---|
| CATSDLVARDEQFF (SEQ ID NO: 334) | JH124_18 | 0 | 0 | 0 | 0 | 0 | 0 |
| CASSYRGTGGGGYTF (SEQ ID NO: 335) | JH124_08 | 0 | 0 | 0 | 0 | 0 | 0 |
| CASSLQGGMGNQPQHF (SEQ ID NO: 336) | JH124_30 | 0 | 0 | 0 | 0 | 0 | 0 |
| CASSLGLGDEQFF (SEQ ID NO: 337) | JH124_30 | 0 | 0 | 0 | 0 | 0 | 0 |
| CASFRQVNYGYTF (SEQ ID NO: 338) | JH124_30 | 0 | 0 | 0 | 0 | 0 | 0 |
| CASSFRQGSYEQYF (SEQ ID NO: 339) | JH124_46 | 0 | 0 | 0 | 0 | 0 | 0 |
| CASSPDIQYF (SEQ ID NO: 340) | JH124_51 | 0 | 0 | 0 | 0 | 0 | 0 |
| CASSETGWGAFF (SEQ ID NO: 341) | JH124_34 | 0 | 1 | 0 | 1 | 0 | 4 |
| CASRRHSNQPQHF (SEQ ID NO: 342) | JH124_52 | 0 | 0 | 0 | 0 | 0 | 0 |
| CASSLVGLAGNEQFF (SEQ ID NO: 343) | JH124_52 | 0 | 0 | 0 | 0 | 0 | 0 |
| CASSPQDQHVYEQYF (SEQ ID NO: 344) | JH124_52 | 0 | 0 | 0 | 0 | 0 | 0 |
| CASTLRVDTEAFF (SEQ ID NO: 345) | JH124_58 | 0 | 0 | 0 | 0 | 0 | 0 |

| | condition | JH124_02_ abundance | JH124_26_ abundance | JH124_37_ abundance | JH124_57_ abundance | JH124_25_ abundance | JH124_33_ abundance | JH124_38_ abundance |
|---|---|---|---|---|---|---|---|---|
| CASSGQGGVSEKLFF (SEQ ID NO: 318) | JH124_04 | 0 | 0 | 0 | 0 | 0 | 0 | 0 |
| CASSLTGGYTGELFF (SEQ ID NO: 319) | JH124_07 | 2 | 0 | 1 | 1 | 0 | 2 | 1 |
| CASSLRSSSETQYF (SEQ ID NO: 320) | JH124_07 | 0 | 0 | 0 | 0 | 0 | 0 | 0 |
| CASSLQAGSSYNEQFF (SEQ ID NO: 321) | JH124_63 | 0 | 0 | 0 | 0 | 0 | 0 | 0 |
| CASSPSGGSLYNEQFF (SEQ ID NO: 322) | JH124_63 | 0 | 0 | 0 | 0 | 0 | 0 | 0 |

TABLE 6-continued

| | | | | | | | | |
|---|---|---|---|---|---|---|---|---|
| CASSGGISNTEAFF (SEQ ID NO: 323) | JH124_35 | 0 | 0 | 0 | 0 | 0 | 0 | 0 |
| CATSTLPSGGEGYEQYF (SEQ ID NO: 324) | JH124_54 | 0 | 1 | 0 | 1 | 0 | 0 | 0 |
| CASSGTTYGYTF (SEQ ID NO: 325) | JH124_09 | 0 | 0 | 0 | 0 | 0 | 0 | 0 |
| CSASRGLSGYTF (SEQ ID NO: 326) | JH124_53 | 0 | 0 | 5 | 0 | 0 | 0 | 0 |
| LGPGTFTSYEQYF (SEQ ID NO: 327) | JH124_28 | 0 | 0 | 0 | 0 | 0 | 0 | 0 |
| CASSTGTGFGEQYF (SEQ ID NO: 328) | JH124_57 | 0 | 0 | 0 | 12 | 0 | 0 | 0 |
| CASSEGGSDEQYF (SEQ ID NO: 329) | JH124_25 | 0 | 0 | 0 | 0 | 27 | 0 | 0 |
| CASSLDPRSSYNSPLHF (SEQ ID NO: 330) | JH124_33 | 0 | 0 | 0 | 0 | 0 | 11 | 0 |
| CASTAGTVHSNQPQHF (SEQ ID NO: 331) | JH124_55 | 0 | 0 | 0 | 0 | 0 | 0 | 0 |
| CASRDTRELNTEAFF (SEQ ID NO: 332) | JH124_59 | 0 | 0 | 0 | 0 | 0 | 0 | 0 |
| CASSLGDLRGFTEAFF (SEQ ID NO: 333) | JH124_59 | 0 | 0 | 0 | 0 | 0 | 0 | 0 |
| CATSDLVARDEQFF (SEQ ID NO: 334) | JH124_18 | 0 | 0 | 0 | 0 | 0 | 0 | 0 |
| CASSYRGTGGGGYTF (SEQ ID NO: 335) | JH124_08 | 0 | 0 | 0 | 0 | 6 | 0 | 2 |
| CASSLQGGMGNQPQHF (SEQ ID NO: 336) | JH124_30 | 0 | 0 | 0 | 1 | 1 | 0 | 0 |
| CASSLGLGDEQFF (SEQ ID NO: 337) | JH124_30 | 0 | 0 | 0 | 0 | 0 | 0 | 0 |
| CASFRQVNYGYTF (SEQ ID NO: 338) | JH124_30 | 0 | 0 | 0 | 0 | 0 | 0 | 0 |
| CASSFRQGSYEQYF (SEQ ID NO: 339) | JH124_46 | 0 | 0 | 0 | 0 | 0 | 0 | 0 |

TABLE 6-continued

| | | | | | | | | |
|---|---|---|---|---|---|---|---|---|
| CASSPDIQYF (SEQ ID NO: 340) | JH124_51 | 0 | 0 | 0 | 0 | 0 | 0 | 0 |
| CASSETGWGAFF (SEQ ID NO: 341) | JH124_34 | 0 | 1 | 0 | 1 | 0 | 0 | 0 |
| CASRRHSNQPQHF (SEQ ID NO: 342) | JH124_52 | 0 | 0 | 0 | 0 | 0 | 0 | 0 |
| CASSLVGLAGNEQFF (SEQ ID NO: 343) | JH124_52 | 0 | 0 | 0 | 0 | 0 | 0 | 0 |
| CASSPQDQHVYEQYF (SEQ ID NO: 344) | JH124_52 | 0 | 0 | 0 | 0 | 0 | 0 | 0 |
| CASTLRVDTEAFF (SEQ ID NO: 345) | JH124_58 | 0 | 0 | 0 | 0 | 0 | 0 | 0 |
| | condition | JH124_60_ abundance | JH124_03_ abundance | JH124_24_ abundance | JH124_48_ abundance | JH124_43_ abundance | JH124_55_ abundance | |
| CASSGQGGVSEKLFF (SEQ ID NO: 318) | JH124_04 | 0 | 5 | 0 | 0 | 0 | 0 | |
| CASSLTGGYTGELFF (SEQ ID NO: 319) | JH124_07 | 3 | 0 | 3 | 1 | 1 | 1 | |
| CASSLRSSSETQYF (SEQ ID NO: 320) | JH124_07 | 0 | 0 | 0 | 0 | 0 | 0 | |
| CASSLQAGSSYNEQFF (SEQ ID NO: 321) | JH124_63 | 0 | 0 | 0 | 0 | 0 | 0 | |
| CASSPSGGSLYNEQFF (SEQ ID NO: 322) | JH124_63 | 0 | 0 | 0 | 0 | 0 | 0 | |
| CASSGGISNTEAFF (SEQ ID NO: 323) | JH124_35 | 0 | 0 | 0 | 0 | 0 | 0 | |
| CATSTLPSGGEGYEQYF (SEQ ID NO: 324) | JH124_54 | 0 | 0 | 0 | 0 | 0 | 0 | |
| CASSGTTYGYTF (SEQ ID NO: 325) | JH124_09 | 0 | 0 | 0 | 0 | 0 | 0 | |
| CSASRGLSGYTF (SEQ ID NO: 326) | JH124_53 | 0 | 0 | 0 | 0 | 0 | 0 | |
| LGPGTFTSYEQYF (SEQ ID NO: 327) | JH124_28 | 0 | 0 | 0 | 0 | 0 | 0 | |
| CASSTGTGFGEQYF (SEQ ID NO: 328) | JH124_57 | 0 | 0 | 0 | 0 | 0 | 0 | |

TABLE 6-continued

| | | | | | | | |
|---|---|---|---|---|---|---|---|
| CASSEGGSDEQYF (SEQ ID NO: 329) | JH124_25 | 0 | 0 | 2 | 0 | 0 | 0 |
| CASSLDPRSSYNSPLHF (SEQ ID NO: 330) | JH124_33 | 0 | 0 | 0 | 0 | 0 | 0 |
| CASTAGTVHSNQPQHF (SEQ ID NO: 331) | JH124_55 | 0 | 0 | 0 | 0 | 1 | 167 |
| CASRDTRELNTEAFF (SEQ ID NO: 332) | JH124_59 | 0 | 0 | 0 | 0 | 0 | 0 |
| CASSLGDLRGFTEAFF (SEQ ID NO: 333) | JH124_59 | 0 | 0 | 0 | 0 | 0 | 0 |
| CATSDLVARDEQFF (SEQ ID NO: 334) | JH124_18 | 0 | 0 | 0 | 0 | 0 | 0 |
| CASSYRGTGGGGYTF (SEQ ID NO: 335) | JH124_08 | 0 | 0 | 0 | 0 | 0 | 0 |
| CASSLQGGMGNQPQHF (SEQ ID NO: 336) | JH124_30 | 0 | 2 | 0 | 0 | 0 | 0 |
| CASSLGLGDEQFF (SEQ ID NO: 337) | JH124_30 | 0 | 0 | 0 | 0 | 0 | 0 |
| CASFRQVNYGYTF (SEQ ID NO: 338) | JH124_30 | 0 | 0 | 0 | 0 | 0 | 0 |
| CASSFRQGSYEQYF (SEQ ID NO: 339) | JH124_46 | 0 | 0 | 0 | 0 | 0 | 0 |
| CASSPDIQYF (SEQ ID NO: 340) | JH124_51 | 0 | 0 | 0 | 0 | 0 | 0 |
| CASSETGWGAFF (SEQ ID NO: 341) | JH124_34 | 9 | 0 | 0 | 4 | 1 | 0 |
| CASRRHSNQPQHF (SEQ ID NO: 342) | JH124_52 | 0 | 0 | 0 | 0 | 0 | 0 |
| CASSLVGLAGNEQFF (SEQ ID NO: 343) | JH124_52 | 0 | 0 | 0 | 0 | 0 | 0 |
| CASSPQDQHVYEQYF (SEQ ID NO: 344) | JH124_52 | 0 | 0 | 0 | 0 | 0 | 0 |
| CASTLRVDTEAFF (SEQ ID NO: 345) | JH124_58 | 0 | 0 | 0 | 0 | 0 | 0 |

TABLE 6-continued

| | condition | JH124_59_ abundance | JH124_18_ abundance | JH124_44_ abundance | JH124_56_ abundance | JH124_08_ abundance | JH124_29_ abundance | JH124_30_ abundance |
|---|---|---|---|---|---|---|---|---|
| CASSGQGGVSEKLFF (SEQ ID NO: 318) | JH124_04 | 0 | 0 | 0 | 0 | 0 | 0 | 0 |
| CASSLTGGYTGELFF (SEQ ID NO: 319) | JH124_07 | 4 | 0 | 0 | 3 | 0 | 2 | 0 |
| CASSLRSSSETQYF (SEQ ID NO: 320) | JH124_07 | 0 | 0 | 0 | 0 | 0 | 0 | 0 |
| CASSLQAGSSYNEQFF (SEQ ID NO: 321) | JH124_63 | 0 | 0 | 0 | 0 | 0 | 0 | 0 |
| CASSPSGGSLYNEQFF (SEQ ID NO: 322) | JH124_63 | 0 | 0 | 0 | 0 | 0 | 0 | 0 |
| CASSGGISNTEAFF (SEQ ID NO: 323) | JH124_35 | 0 | 0 | 0 | 0 | 0 | 0 | 0 |
| CATSTLPSGGEGYEQYF (SEQ ID NO: 324) | JH124_54 | 0 | 0 | 0 | 0 | 0 | 0 | 0 |
| CASSGTTYGYTF (SEQ ID NO: 325) | JH124_09 | 0 | 0 | 0 | 0 | 0 | 0 | 0 |
| CSASRGLSGYTF (SEQ ID NO: 326) | JH124_53 | 0 | 0 | 0 | 0 | 0 | 0 | 0 |
| LGPGTFTSYEQYF (SEQ ID NO: 327) | JH124_28 | 0 | 0 | 0 | 0 | 0 | 0 | 0 |
| CASSTGTGFGEQYF (SEQ ID NO: 328) | JH124_57 | 0 | 0 | 0 | 0 | 0 | 0 | 0 |
| CASSEGGSDEQYF (SEQ ID NO: 329) | JH124_25 | 0 | 0 | 0 | 0 | 0 | 0 | 0 |
| CASSLDPRSSYNSPLHF (SEQ ID NO: 330) | JH124_33 | 0 | 0 | 0 | 0 | 0 | 0 | 0 |
| CASTAGTVHSNQPQHF (SEQ ID NO: 331) | JH124_55 | 0 | 0 | 0 | 0 | 0 | 0 | 0 |
| CASRDTRELNTEAFF (SEQ ID NO: 332) | JH124_59 | 109 | 0 | 0 | 0 | 0 | 0 | 0 |
| CASSLGDLRGFTEAFF (SEQ ID NO: 333) | JH124_59 | 101 | 0 | 0 | 0 | 0 | 0 | 0 |
| CATSDLVARDEQFF (SEQ ID NO: 334) | JH124_18 | 0 | 10 | 0 | 0 | 0 | 0 | 0 |

TABLE 6-continued

| | | | | | | | | |
|---|---|---|---|---|---|---|---|---|
| CASSYRGTGGGGYTF (SEQ ID NO: 335) | JH124_08 | 0 | 0 | 0 | 1 | 144 | 0 | 0 |
| CASSLQGGMGNQPQHF (SEQ ID NO: 336) | JH124_30 | 0 | 0 | 0 | 0 | 0 | 0 | 39 |
| CASSLGLGDEQFF (SEQ ID NO: 337) | JH124_30 | 0 | 0 | 0 | 0 | 0 | 0 | 19 |
| CASFRQVNYGYTF (SEQ ID NO: 338) | JH124_30 | 0 | 0 | 0 | 0 | 0 | 0 | 12 |
| CASSFRQGSYEQYF (SEQ ID NO: 339) | JH124_46 | 0 | 0 | 0 | 0 | 0 | 0 | 0 |
| CASSPDIQYF (SEQ ID NO: 340) | JH124_51 | 0 | 0 | 0 | 0 | 0 | 0 | 0 |
| CASSETGWGAFF (SEQ ID NO: 341) | JH124_34 | 1 | 1 | 0 | 0 | 1 | 0 | 1 |
| CASRRHSNQPQHF (SEQ ID NO: 342) | JH124_52 | 0 | 0 | 0 | 0 | 0 | 0 | 0 |
| CASSLVGLAGNEQFF (SEQ ID NO: 343) | JH124_52 | 0 | 0 | 0 | 0 | 0 | 0 | 0 |
| CASSPQDQHVYEQYF (SEQ ID NO: 344) | JH124_52 | 0 | 0 | 0 | 0 | 0 | 0 | 0 |
| CASTLRVDTEAFF (SEQ ID NO: 345) | JH124_58 | 0 | 0 | 0 | 0 | 0 | 0 | 0 |

| | condition | JH124_46_ abundance | JH124_20_ abundance | JH124_23_ abundance | JH124_51_ abundance | JH124_34_ abundance | JH124_52_ abundance |
|---|---|---|---|---|---|---|---|
| CASSGQGGVSEKLFF (SEQ ID NO: 318) | JH124_04 | 0 | 0 | 0 | 0 | 0 | 0 |
| CASSLTGGYTGELFF (SEQ ID NO: 319) | JH124_07 | 0 | 0 | 3 | 0 | 1 | 1 |
| CASSLRSSSETQYF (SEQ ID NO: 320) | JH124_07 | 0 | 0 | 0 | 0 | 0 | 0 |
| CASSLQAGSSYNEQFF (SEQ ID NO: 321) | JH124_63 | 0 | 0 | 0 | 0 | 0 | 0 |
| CASSPSGGSLYNEQFF (SEQ ID NO: 322) | JH124_63 | 0 | 0 | 0 | 0 | 0 | 0 |

TABLE 6-continued

| | | | | | | | |
|---|---|---|---|---|---|---|---|
| CASSGGISNTEAFF (SEQ ID NO: 323) | JH124_35 | 0 | 0 | 0 | 0 | 0 | 0 |
| CATSTLPSGGEGYEQYF (SEQ ID NO: 324) | JH124_54 | 0 | 0 | 0 | 0 | 0 | 0 |
| CASSGTTYGYTF (SEQ ID NO: 325) | JH124_09 | 0 | 0 | 0 | 0 | 0 | 0 |
| CSASRGLSGYTF (SEQ ID NO: 326) | JH124_53 | 0 | 0 | 0 | 0 | 0 | 0 |
| LGPGTFTSYEQYF (SEQ ID NO: 327) | JH124_28 | 0 | 0 | 0 | 0 | 0 | 0 |
| CASSTGTGFGEQYF (SEQ ID NO: 328) | JH124_57 | 0 | 0 | 0 | 0 | 0 | 0 |
| CASSEGGSDEQYF (SEQ ID NO: 329) | JH124_25 | 0 | 0 | 0 | 0 | 0 | 0 |
| CASSLDPRSSYNSPLHF (SEQ ID NO: 330) | JH124_33 | 0 | 0 | 0 | 0 | 0 | 0 |
| CASTAGTVHSNQPQHF (SEQ ID NO: 331) | JH124_55 | 0 | 0 | 0 | 0 | 0 | 0 |
| CASRDTRELNTEAFF (SEQ ID NO: 332) | JH124_59 | 0 | 0 | 0 | 0 | 0 | 0 |
| CASSLGDLRGFTEAFF (SEQ ID NO: 333) | JH124_59 | 0 | 0 | 0 | 0 | 0 | 0 |
| CATSDLVARDEQFF (SEQ ID NO: 334) | JH124_18 | 0 | 0 | 0 | 0 | 0 | 0 |
| CASSYRGTGGGGYTF (SEQ ID NO: 335) | JH124_08 | 0 | 0 | 0 | 0 | 0 | 2 |
| CASSLQGGMGNQPQHF (SEQ ID NO: 336) | JH124_30 | 0 | 0 | 0 | 5 | 0 | 2 |
| CASSLGLGDEQFF (SEQ ID NO: 337) | JH124_30 | 0 | 0 | 0 | 0 | 0 | 0 |
| CASFRQVNYGYTF (SEQ ID NO: 338) | JH124_30 | 0 | 0 | 0 | 0 | 0 | 0 |
| CASSFRQGSYEQYF (SEQ ID NO: 339) | JH124_46 | 40 | 0 | 0 | 0 | 0 | 0 |
| CASSPDIQYF (SEQ ID NO: 340) | JH124_51 | 0 | 0 | 0 | 15 | 0 | 0 |

TABLE 6-continued

| | | | | | | | |
|---|---|---|---|---|---|---|---|
| CASSETGWGAFF (SEQ ID NO: 341) | JH124_34 | 0 | 0 | 0 | 2 | 77 | 3 |
| CASRRHSNQPQHF (SEQ ID NO: 342) | JH124_52 | 0 | 0 | 0 | 0 | 0 | 157 |
| CASSLVGLAGNEQFF (SEQ ID NO: 343) | JH124_52 | 0 | 0 | 0 | 7 | 0 | 64 |
| CASSPQDQHVYEQYF (SEQ ID NO: 344) | JH124_52 | 0 | 0 | 0 | 0 | 0 | 29 |
| CASTLRVDTEAFF (SEQ ID NO: 345) | JH124_58 | 0 | 0 | 0 | 0 | 0 | 0 |

| | condition | JH124_58_ abundance | JH124_PBMC_2w_ abundance | JH124_PBMC_10w_ abundance | JH124_PBMC_4w__ abundance |
|---|---|---|---|---|---|
| CASSGQGGVSEKLFF (SEQ ID NO: 318) | JH124_04 | 0 | 0 | 0 | 0 |
| CASSLTGGYTGELFF (SEQ ID NO: 319) | JH124_07 | 0 | 10 | 4 | 10 |
| CASSLRSSSETQYF (SEQ ID NO: 320) | JH124_07 | 0 | 0 | 0 | 0 |
| CASSLQAGSSYNEQFF (SEQ ID NO: 321) | JH124_63 | 0 | 0 | 0 | 0 |
| CASSPSGGSLYNEQFF (SEQ ID NO: 322) | JH124_63 | 0 | 0 | 0 | 0 |
| CASSGGISNTEAFF (SEQ ID NO: 323) | JH124_35 | 0 | 0 | 0 | 0 |
| CATSTLPSGGEGYEQYF (SEQ ID NO: 324) | JH124_54 | 0 | 0 | 0 | 0 |
| CASSGTTYGYTF (SEQ ID NO: 325) | JH124_09 | 0 | 8 | 27 | 10 |
| CSASRGLSGYTF (SEQ ID NO: 326) | JH124_53 | 0 | 0 | 0 | 0 |
| LGPGTFTSYEQYF (SEQ ID NO: 327) | JH124_28 | 0 | 0 | 0 | 3 |
| CASSTGTGFGEQYF (SEQ ID NO: 328) | JH124_57 | 0 | 0 | 0 | 0 |

TABLE 6-continued

| | | | | | |
|---|---|---|---|---|---|
| CASSEGGSDEQYF (SEQ ID NO: 329) | JH124_25 | 0 | 0 | 0 | 0 |
| CASSLDPRSSYNSPLHF (SEQ ID NO: 330) | JH124_33 | 0 | 0 | 0 | 0 |
| CASTAGTVHSNQPQHF (SEQ ID NO: 331) | JH124_55 | 0 | 0 | 0 | 0 |
| CASRDTRELNTEAFF (SEQ ID NO: 332) | JH124_59 | 0 | 0 | 0 | 0 |
| CASSLGDLRGFTEAFF (SEQ ID NO: 333) | JH124_59 | 0 | 0 | 0 | 0 |
| CATSDLVARDEQFF (SEQ ID NO: 334) | JH124_18 | 0 | 0 | 0 | 0 |
| CASSYRGTGGGGYTF (SEQ ID NO: 335) | JH124_08 | 0 | 0 | 0 | 0 |
| CASSLQGGMGNQPQHF (SEQ ID NO: 336) | JH124_30 | 0 | 0 | 11 | 7 |
| CASSLGLGDEQFF (SEQ ID NO: 337) | JH124_30 | 0 | 0 | 2 | 0 |
| CASFRQVNYGYTF (SEQ ID NO: 338) | JH124_30 | 0 | 0 | 0 | 0 |
| CASSFRQGSYEQYF (SEQ ID NO: 339) | JH124_46 | 0 | 0 | 0 | 0 |
| CASSPDIQYF (SEQ ID NO: 340) | JH124_51 | 0 | 0 | 0 | 0 |
| CASSETGWGAFF (SEQ ID NO: 341) | JH124_34 | 1 | 0 | 0 | 0 |
| CASRRHSNQPQHF (SEQ ID NO: 342) | JH124_52 | 0 | 0 | 0 | 0 |
| CASSLVGLAGNEQFF (SEQ ID NO: 343) | JH124_52 | 0 | 0 | 0 | 0 |
| CASSPQDQHVYEQYF (SEQ ID NO: 344) | JH124_52 | 0 | 0 | 0 | 0 |
| CASTLRVDTEAFF (SEQ ID NO: 345) | JH124_58 | 42 | 0 | 0 | 0 |

TABLE 6-continued

| | condition | JH124_PBMC_ PreRx_abundance | JH124_Tumor_ abundance | JH124_PBMC_68w_ percent | JH124_baseline percent | JH124_PBMC_64w_ percent |
|---|---|---|---|---|---|---|
| CASSGQGGVSEKLFF (SEQ ID NO: 318) | JH124_04 | 0 | 0 | 0 | 0 | 0 |
| CASSLTGGYTGELFF (SEQ ID NO: 319) | JH124_07 | 2 | 5 | 0.002048131 | 0.093457944 | 0 |
| CASSLRSSSETQYF (SEQ ID NO: 320) | JH124_07 | 0 | 0 | 0 | 0 | 0 |
| CASSLQAGSSYNEQFF (SEQ ID NO: 321) | JH124_63 | 0 | 0 | 0 | 0 | 0 |
| CASSPSGGSLYNEQFF (SEQ ID NO: 322) | JH124_63 | 0 | 0 | 0 | 0 | 0 |
| CASSGGISNTEAFF (SEQ ID NO: 323) | JH124_35 | 0 | 0 | 0 | 0 | 0 |
| CATSTLPSGGEGYEQYF (SEQ ID NO: 324) | JH124_54 | 0 | 0 | 0 | 0.186915888 | 0 |
| CASSGTTYGYTF (SEQ ID NO: 325) | JH124_09 | 0 | 0 | 0.008192524 | 0 | 0.016853072 |
| CSASRGLSGYTF (SEQ ID NO: 326) | JH124_53 | 0 | 0 | 0 | 0 | 0 |
| LGPGTFTSYEQYF (SEQ ID NO: 327) | JH124_28 | 3 | 0 | 0 | 0 | 0.003064195 |
| CASSTGTGFGEQYF (SEQ ID NO: 328) | JH124_57 | 0 | 0 | 0 | 0 | 0 |
| CASSEGGSDEQYF (SEQ ID NO: 329) | JH124_25 | 0 | 0 | 0 | 0 | 0 |
| CASSLDPRSSYNSPLHF (SEQ ID NO: 330) | JH124_33 | 0 | 0 | 0 | 0 | 0 |
| CASTAGTVHSNQPQHF (SEQ ID NO: 331) | JH124_55 | 0 | 0 | 0 | 0 | 0 |
| CASRDTRELNTEAFF (SEQ ID NO: 332) | JH124_59 | 0 | 0 | 0 | 0 | 0 |
| CASSLGDLRGFTEAFF (SEQ ID NO: 333) | JH124_59 | 0 | 0 | 0 | 0 | 0 |
| CATSDLVARDEQFF (SEQ ID NO: 334) | JH124_18 | 0 | 0 | 0 | 0 | 0 |

TABLE 6-continued

| | | | | | | |
|---|---|---|---|---|---|---|
| CASSYRGTGGGGYTF (SEQ ID NO: 335) | JH124_08 | 0 | 0 | 0.002048131 | 0 | 0 |
| CASSLQGGMGNQPQHF (SEQ ID NO: 336) | JH124_30 | 2 | 0 | 0.004096262 | 0 | 0.001532097 |
| CASSLGLGDEQFF (SEQ ID NO: 337) | JH124_30 | 2 | 0 | 0 | 0 | 0.001532097 |
| CASFRQVNYGYTF (SEQ ID NO: 338) | JH124_30 | 0 | 0 | 0 | 0 | 0 |
| CASSFRQGSYEQYF (SEQ ID NO: 339) | JH124_46 | 0 | 0 | 0 | 0 | 0 |
| CASSPDIQYF (SEQ ID NO: 340) | JH124_51 | 0 | 0 | 0 | 0 | 0 |
| CASSETGWGAFF (SEQ ID NO: 341) | JH124_34 | 0 | 0 | 0.016385049 | 0.186915888 | 0.041366631 |
| CASRRHSNQPQHF (SEQ ID NO: 342) | JH124_52 | 0 | 0 | 0 | 0 | 0 |
| CASSLVGLAGNEQFF (SEQ ID NO: 343) | JH124_52 | 0 | 0 | 0 | 0 | 0 |
| CASSPQDQHVYEQYF (SEQ ID NO: 344) | JH124_52 | 0 | 0 | 0 | 0 | 0 |
| CASTLRVDTEAFF (SEQ ID NO: 345) | JH124_58 | 0 | 0 | 0 | 0 | 0 |
| | condition | JH124_NoPep_ percent | JH124_10_ percent | JH124_49_ percent | JH124_50_ percent | JH124_04_ percent |
| CASSGQGGVSEKLFF (SEQ ID NO: 318) | JH124_04 | 0 | 0 | 0 | 0 | 2.737226 |
| CASSLTGGYTGELFF (SEQ ID NO: 319) | JH124_07 | 0.079365079 | 0 | 0.038153 | 0.075047 | 0 |
| CASSLRSSSETQYF (SEQ ID NO: 320) | JH124_07 | 0 | 0 | 0 | 0 | 0 |
| CASSLQAGSSYNEQFF (SEQ ID NO: 321) | JH124_63 | 0 | 0 | 0 | 0 | 0 |
| CASSPSGGSLYNEQFF (SEQ ID NO: 322) | JH124_63 | 0 | 0 | 0 | 0 | 0 |

TABLE 6-continued

| | | | | | | |
|---|---|---|---|---|---|---|
| CASSGGISNTEAFF (SEQ ID NO: 323) | JH124_35 | 0 | 0 | 0 | 0 | 0 |
| CATSTLPSGGEGYEQYF (SEQ ID NO: 324) | JH124_54 | 0 | 0 | 0 | 0 | 0 |
| CASSGTTYGYTF (SEQ ID NO: 325) | JH124_09 | 0 | 0 | 0 | 0 | 0 |
| CSASRGLSGYTF (SEQ ID NO: 326) | JH124_53 | 0 | 0 | 0 | 0 | 0 |
| LGPGTFTSYEQYF (SEQ ID NO: 327) | JH124_28 | 0 | 0 | 0 | 0 | 0 |
| CASSTGTGFGEQYF (SEQ ID NO: 328) | JH124_57 | 0 | 0 | 0 | 0 | 0 |
| CASSEGGSDEQYF (SEQ ID NO: 329) | JH124_25 | 0 | 0 | 0 | 0 | 0 |
| CASSLDPRSSYNSPLHF (SEQ ID NO: 330) | JH124_33 | 0 | 0 | 0 | 0 | 0 |
| CASTAGTVHSNQPQHF (SEQ ID NO: 331) | JH124_55 | 0 | 0 | 0 | 0 | 0 |
| CASRDTRELNTEAFF (SEQ ID NO: 332) | JH124_59 | 0 | 0 | 0 | 0 | 0 |
| CASSLGDLRGFTEAFF (SEQ ID NO: 333) | JH124_59 | 0.158730159 | 0 | 0 | 0 | 0 |
| CATSDLVARDEQFF (SEQ ID NO: 334) | JH124_18 | 0 | 0 | 0 | 0 | 0 |
| CASSYRGTGGGGYTF (SEQ ID NO: 335) | JH124_08 | 0 | 0 | 0 | 0 | 0 |
| CASSLQGGMGNQPQHF (SEQ ID NO: 336) | JH124_30 | 0 | 0 | 0 | 0.037523 | 0 |
| CASSLGLGDEQFF (SEQ ID NO: 337) | JH124_30 | 0 | 0 | 0 | 0 | 0 |
| CASFRQVNYGYTF (SEQ ID NO: 338) | JH124_30 | 0 | 0 | 0 | 0 | 0 |
| CASSFRQGSYEQYF (SEQ ID NO: 339) | JH124_46 | 0 | 0 | 0 | 0 | 0 |
| CASSPDIQYF (SEQ ID NO: 340) | JH124_51 | 0 | 0 | 0 | 0 | 0 |

TABLE 6-continued

| | | | | | | |
|---|---|---|---|---|---|---|
| CASSETGWGAFF (SEQ ID NO: 341) | JH124_34 | 0.238095238 | 0 | 0.038153 | 0.150094 | 0 |
| CASRRHSNQPQHF (SEQ ID NO: 342) | JH124_52 | 0 | 0 | 0 | 0 | 0 |
| CASSLVGLAGNEQFF (SEQ ID NO: 343) | JH124_52 | 0 | 0 | 0 | 0 | 0 |
| CASSPQDQHVYEQYF (SEQ ID NO: 344) | JH124_52 | 0 | 0 | 0 | 0 | 0 |
| CASTLRVDTEAFF (SEQ ID NO: 345) | JH124_58 | 0 | 0 | 0 | 0 | 0 |

| | condition | JH124_19_ percent | JH124_05_ percent | JH124_27_ percent | JH124_63_ percent | JH124_35_ percent | JH124_54_ percent |
|---|---|---|---|---|---|---|---|
| CASSGQGGVSEKLFF (SEQ ID NO: 318) | JH124_04 | 0 | 0 | 0 | 0 | 0 | 0 |
| CASSLTGGYTGELFF (SEQ ID NO: 319) | JH124_07 | 0 | 0.128991 | 0 | 0.190476 | 0.039308 | 0.059365 |
| CASSLRSSSETQYF (SEQ ID NO: 320) | JH124_07 | 0 | 0 | 0 | 0 | 0 | 0 |
| CASSLQAGSSYNEQFF (SEQ ID NO: 321) | JH124_63 | 0 | 0 | 0 | 2.190476 | 0 | 0 |
| CASSPSGGSLYNEQFF (SEQ ID NO: 322) | JH124_63 | 0 | 0 | 0 | 0.761905 | 0 | 0 |
| CASSGGISNTEAFF (SEQ ID NO: 323) | JH124_35 | 0.031786 | 0 | 0 | 0 | 2.122642 | 0 |
| CATSTLPSGGEGYEQYF (SEQ ID NO: 324) | JH124_54 | 0 | 0 | 0 | 0 | 0 | 0.74206 |
| CASSGTTYGYTF (SEQ ID NO: 325) | JH124_09 | 0 | 0 | 0 | 0 | 0 | 0 |
| CSASRGLSGYTF (SEQ ID NO: 326) | JH124_53 | 0 | 0 | 0 | 0 | 0 | 0 |
| LGPGTFTSYEQYF (SEQ ID NO: 327) | JH124_28 | 0 | 0 | 0 | 0 | 0 | 0 |
| CASSTGTGFGEQYF (SEQ ID NO: 328) | JH124_57 | 0 | 0 | 0 | 0 | 0 | 0 |

TABLE 6-continued

| | | | | | | | |
|---|---|---|---|---|---|---|---|
| CASSEGGSDEQYF (SEQ ID NO: 329) | JH124_25 | 0 | 0 | 0 | 0 | 0 | 0 |
| CASSLDPRSSYNSPLHF (SEQ ID NO: 330) | JH124_33 | 0 | 0 | 0 | 0 | 0 | 0 |
| CASTAGTVHSNQPQHF (SEQ ID NO: 331) | JH124_55 | 0 | 0 | 0 | 0 | 0 | 0.089047 |
| CASRDTRELNTEAFF (SEQ ID NO: 332) | JH124_59 | 0 | 0 | 0 | 0 | 0 | 0 |
| CASSLGDLRGFTEAFF (SEQ ID NO: 333) | JH124_59 | 0 | 0 | 0 | 0 | 0 | 0 |
| CATSDLVARDEQFF (SEQ ID NO: 334) | JH124_18 | 0 | 0 | 0 | 0 | 0 | 0 |
| CASSYRGTGGGGYTF (SEQ ID NO: 335) | JH124_08 | 0 | 0 | 0 | 0 | 0 | 0 |
| CASSLQGGMGNQPQHF (SEQ ID NO: 336) | JH124_30 | 0 | 0 | 0 | 0 | 0 | 0.029682 |
| CASSLGLGDEQFF (SEQ ID NO: 337) | JH124_30 | 0 | 0 | 0 | 0 | 0.039308 | 0 |
| CASFRQVNYGYTF (SEQ ID NO: 338) | JH124_30 | 0 | 0 | 0 | 0 | 0 | 0 |
| CASSFRQGSYEQYF (SEQ ID NO: 339) | JH124_46 | 0 | 0 | 0 | 0 | 0 | 0 |
| CASSPDIQYF (SEQ ID NO: 340) | JH124_51 | 0.031786 | 0.032248 | 0.078958 | 0 | 0 | 0 |
| CASSETGWGAFF (SEQ ID NO: 341) | JH124_34 | 0 | 0 | 0 | 0 | 0 | 0 |
| CASRRHSNQPQHF (SEQ ID NO: 342) | JH124_52 | 0 | 0 | 0 | 0 | 0 | 0 |
| CASSLVGLAGNEQFF (SEQ ID NO: 343) | JH124_52 | 0 | 0 | 0 | 0 | 0 | 0 |
| CASSPQDQHVYEQYF (SEQ ID NO: 344) | JH124_52 | 0 | 0 | 0 | 0 | 0 | 0 |
| CASTLRVDTEAFF (SEQ ID NO: 345) | JH124_58 | 0 | 0 | 0 | 0 | 0 | 0 |

TABLE 6-continued

| | condition | JH124_61_ percent | JH124_09_ percent | JH124_45_ percent | JH124_53_ percent | JH124_06_ percent | JH124_28_ percent |
|---|---|---|---|---|---|---|---|
| CASSGQGGVSEKLFF (SEQ ID NO: 318) | JH124_04 | 0 | 0 | 0 | 0 | 0 | 0 |
| CASSLTGGYTGELFF (SEQ ID NO: 319) | JH124_07 | 0.069589 | 0.112549 | 0.083857 | 0.207756 | 0 | 0.061881 |
| CASSLRSSSETQYF (SEQ ID NO: 320) | JH124_07 | 0 | 0 | 0 | 0 | 0 | 0 |
| CASSLQAGSSYNEQFF (SEQ ID NO: 321) | JH124_63 | 0 | 0 | 0 | 0 | 0 | 0 |
| CASSPSGGSLYNEQFF (SEQ ID NO: 322) | JH124_63 | 0 | 0 | 0 | 0 | 0 | 0 |
| CASSGGISNTEAFF (SEQ ID NO: 323) | JH124_35 | 0 | 0 | 0 | 0 | 0 | 0 |
| CATSTLPSGGEGYEQYF (SEQ ID NO: 324) | JH124_54 | 0 | 0 | 0 | 0 | 0 | 0 |
| CASSGTTYGYTF (SEQ ID NO: 325) | JH124_09 | 0 | 6.359032 | 0 | 0 | 0 | 0.123762 |
| CSASRGLSGYTF (SEQ ID NO: 326) | JH124_53 | 0 | 0 | 0 | 3.774238 | 0 | 0 |
| LGPGTFTSYEQYF (SEQ ID NO: 327) | JH124_28 | 0 | 0 | 0 | 0 | 0 | 0.804455 |
| CASSTGTGFGEQYF (SEQ ID NO: 328) | JH124_57 | 0 | 0 | 0 | 0 | 0 | 0 |
| CASSEGGSDEQYF (SEQ ID NO: 329) | JH124_25 | 0 | 0 | 0 | 0 | 0 | 0 |
| CASSLDPRSSYNSPLHF (SEQ ID NO: 330) | JH124_33 | 0 | 0 | 0 | 0 | 0 | 0 |
| CASTAGTVHSNQPQHF (SEQ ID NO: 331) | JH124_55 | 0 | 0 | 0 | 0 | 0 | 0 |
| CASSGQGGVSEKLFF (SEQ ID NO: 332) | JH124_59 | 0 | 0 | 0 | 0 | 0 | 0 |
| CASSLTGGYTGELFF (SEQ ID NO: 333) | JH124_59 | 0 | 0 | 0 | 0 | 0 | 0 |
| CASSLRSSSETQYF (SEQ ID NO: 334) | JH124_18 | 0 | 0 | 0.167715 | 0 | 0 | 0 |

TABLE 6-continued

| | | | | | | | |
|---|---|---|---|---|---|---|---|
| CASSLQAGSSYNEQFF (SEQ ID NO: 335) | JH124_08 | 0 | 0 | 0 | 0 | 0 | 0 |
| CASSPSGGSLYNEQFF (SEQ ID NO: 336) | JH124_30 | 0 | 0 | 0 | 0 | 0 | 0 |
| CASSGGISNTEAFF (SEQ ID NO: 337) | JH124_30 | 0 | 0 | 0 | 0 | 0 | 0 |
| CATSTLPSGGEGYEQYF (SEQ ID NO: 338) | JH124_30 | 0 | 0 | 0 | 0 | 0 | 0 |
| CASSGTTYGYTF (SEQ ID NO: 339) | JH124_46 | 0 | 0 | 0 | 0 | 0 | 0 |
| CSASRGLSGYTF (SEQ ID NO: 340) | JH124_51 | 0 | 0 | 0 | 0 | 0 | 0 |
| LGPGTFTSYEQYF (SEQ ID NO: 341) | JH124_34 | 0 | 0.056275 | 0.020964 | 0 | 0.075131 | 0 |
| CASSTGTGFGEQYF (SEQ ID NO: 342) | JH124_52 | 0 | 0 | 0 | 0 | 0 | 0 |
| CASSEGGSDEQYF (SEQ ID NO: 343) | JH124_52 | 0 | 0 | 0 | 0 | 0 | 0 |
| CASSLDPRSSYNSPLHF (SEQ ID NO: 344) | JH124_52 | 0 | 0 | 0 | 0 | 0 | 0 |
| CASTAGTVHSNQPQHF (SEQ ID NO: 345) | JH124_58 | 0 | 0 | 0 | 0 | 0 | 0 |

| | condition | JH124_47_ percent | JH124_62_ percent | JH124_02_ percent | JH124_26_ percent | JH124_37_ percent | JH124_57_ percent | JH124_25_ percent |
|---|---|---|---|---|---|---|---|---|
| CASSGQGGVSEKLFF (SEQ ID NO: 318) | JH124_04 | 0 | 0 | 0 | 0 | 0 | 0 | 0 |
| CASSLTGGYTGELFF (SEQ ID NO: 319) | JH124_07 | 0.105005 | 0 | 0.252845 | 0 | 0.035063 | 0.062933 | 0 |
| CASSLRSSSETQYF (SEQ ID NO: 320) | JH124_07 | 0 | 0 | 0 | 0 | 0 | 0 | 0 |
| CASSLQAGSSYNEQFF (SEQ ID NO: 321) | JH124_63 | 0 | 0 | 0 | 0 | 0 | 0 | 0 |
| CASSPSGGSLYNEQFF (SEQ ID NO: 322) | JH124_63 | 0 | 0 | 0 | 0 | 0 | 0 | 0 |

TABLE 6-continued

| | | | | | | | | |
|---|---|---|---|---|---|---|---|---|
| CASSGGISNTEAFF (SEQ ID NO: 323) | JH124_35 | 0 | 0 | 0 | 0 | 0 | 0 | 0 |
| CATSTLPSGGEGYEQYF (SEQ ID NO: 324) | JH124_54 | 0 | 0 | 0 | 0.055835 | 0 | 0.062933 | 0 |
| CASSGTTYGYTF (SEQ ID NO: 325) | JH124_09 | 0 | 0 | 0 | 0 | 0 | 0 | 0 |
| CSASRGLSGYTF (SEQ ID NO: 326) | JH124_53 | 0 | 0 | 0 | 0 | 0.175316 | 0 | 0 |
| LGPGTFTSYEQYF (SEQ ID NO: 327) | JH124_28 | 0 | 0 | 0 | 0 | 0 | 0 | 0 |
| CASSTGTGFGEQYF (SEQ ID NO: 328) | JH124_57 | 0 | 0 | 0 | 0 | 0 | 0.755192 | 0 |
| CASSEGGSDEQYF (SEQ ID NO: 329) | JH124_25 | 0 | 0 | 0 | 0 | 0 | 0 | 1.070579 |
| CASSLDPRSSYNSPLHF (SEQ ID NO: 330) | JH124_33 | 0 | 0 | 0 | 0 | 0 | 0 | 0 |
| CASTAGTVHSNQPQHF (SEQ ID NO: 331) | JH124_55 | 0 | 0 | 0 | 0 | 0 | 0 | 0 |
| CASRDTRELNTEAFF (SEQ ID NO: 332) | JH124_59 | 0 | 0 | 0 | 0 | 0 | 0 | 0 |
| CASSLGDLRGFTEAFF (SEQ ID NO: 333) | JH124_59 | 0 | 0 | 0 | 0 | 0 | 0 | 0 |
| CATSDLVARDEQFF (SEQ ID NO: 334) | JH124_18 | 0 | 0 | 0 | 0 | 0 | 0 | 0 |
| CASSYRGTGGGGYTF (SEQ ID NO: 335) | JH124_08 | 0 | 0 | 0 | 0 | 0 | 0 | 0.237906 |
| CASSLQGGMGNQPQHF (SEQ ID NO: 336) | JH124_30 | 0 | 0 | 0 | 0 | 0 | 0.062933 | 0.039651 |
| CASSLGLGDEQFF (SEQ ID NO: 337) | JH124_30 | 0 | 0 | 0 | 0 | 0 | 0 | 0 |
| CASFRQVNYGYTF (SEQ ID NO: 338) | JH124_30 | 0 | 0 | 0 | 0 | 0 | 0 | 0 |
| CASSFRQGSYEQYF (SEQ ID NO: 339) | JH124_46 | 0 | 0 | 0 | 0 | 0 | 0 | 0 |
| CASSPDIQYF (SEQ ID NO: 340) | JH124_51 | 0 | 0 | 0 | 0 | 0 | 0 | 0 |

TABLE 6-continued

| | | | | | | | | |
|---|---|---|---|---|---|---|---|---|
| CASSETGWGAFF (SEQ ID NO: 341) | JH124_34 | 0 | 0.470588 | 0 | 0.055835 | 0 | 0.062933 | 0 |
| CASRRHSNQPQHF (SEQ ID NO: 342) | JH124_52 | 0 | 0 | 0 | 0 | 0 | 0 | 0 |
| CASSLVGLAGNEQFF (SEQ ID NO: 343) | JH124_52 | 0 | 0 | 0 | 0 | 0 | 0 | 0 |
| CASSPQDQHVYEQYF (SEQ ID NO: 344) | JH124_52 | 0 | 0 | 0 | 0 | 0 | 0 | 0 |
| CASTLRVDTEAFF (SEQ ID NO: 345) | JH124_58 | 0 | 0 | 0 | 0 | 0 | 0 | 0 |

| | condition | JH124_25_ percent | JH124_33_ percent | JH124_38_ percent | JH124_60_ percent | JH124_03_ percent | JH124_24_ percent |
|---|---|---|---|---|---|---|---|
| CASSGQGGVSEKLFF (SEQ ID NO: 318) | JH124_04 | 0 | 0 | 0 | 0 | 0 | 0 |
| CASSLTGGYTGELFF (SEQ ID NO: 319) | JH124_07 | 0 | 0.128287 | 0.035112 | 0.0899526 | 0 | 0.103128 |
| CASSLRSSSETQYF (SEQ ID NO: 320) | JH124_07 | 0 | 0 | 0 | 0 | 0 | 0 |
| CASSLQAGSSYNEQFF (SEQ ID NO: 321) | JH124_63 | 0 | 0 | 0 | 0 | 0 | 0 |
| CASSPSGGSLYNEQFF (SEQ ID NO: 322) | JH124_63 | 0 | 0 | 0 | 0 | 0 | 0 |
| CASSGGISNTEAFF (SEQ ID NO: 323) | JH124_35 | 0 | 0 | 0 | 0 | 0 | 0 |
| CATSTLPSGGEGYEQYF (SEQ ID NO: 324) | JH124_54 | 0 | 0 | 0 | 0 | 0 | 0 |
| CASSGTTYGYTF (SEQ ID NO: 325) | JH124_09 | 0 | 0 | 0 | 0 | 0 | 0 |
| CSASRGLSGYTF (SEQ ID NO: 326) | JH124_53 | 0 | 0 | 0 | 0 | 0 | 0 |
| LGPGTFTSYEQYF (SEQ ID NO: 327) | JH124_28 | 0 | 0 | 0 | 0 | 0 | 0 |
| CASSTGTGFGEQYF (SEQ ID NO: 328) | JH124_57 | 0 | 0 | 0 | 0 | 0 | 0 |

TABLE 6-continued

| | | | | | | | |
|---|---|---|---|---|---|---|---|
| CASSEGGSDEQYF (SEQ ID NO: 329) | JH124_25 | 1.070579 | 0 | 0 | 0 | 0 | 0.068752 |
| CASSLDPRSSYNSPLHF (SEQ ID NO: 330) | JH124_33 | 0 | 0.705581 | 0 | 0 | 0 | 0 |
| CASTAGTVHSNQPQHF (SEQ ID NO: 331) | JH124_55 | 0 | 0 | 0 | 0 | 0 | 0 |
| CASRDTRELNTEAFF (SEQ ID NO: 332) | JH124_59 | 0 | 0 | 0 | 0 | 0 | 0 |
| CASSLGDLRGFTEAFF (SEQ ID NO: 333) | JH124_59 | 0 | 0 | 0 | 0 | 0 | 0 |
| CATSDLVARDEQFF (SEQ ID NO: 334) | JH124_18 | 0 | 0 | 0 | 0 | 0 | 0 |
| CASSYRGTGGGGYTF (SEQ ID NO: 335) | JH124_08 | 0.237906 | 0 | 0.070225 | 0 | 0 | 0 |
| CASSLQGGMGNQPQHF (SEQ ID NO: 336) | JH124_30 | 0.039651 | 0 | 0 | 0 | 0.122624 | 0 |
| CASSLGLGDEQFF (SEQ ID NO: 337) | JH124_30 | 0 | 0 | 0 | 0 | 0 | 0 |
| CASFRQVNYGYTF (SEQ ID NO: 338) | JH124_30 | 0 | 0 | 0 | 0 | 0 | 0 |
| CASSFRQGSYEQYF (SEQ ID NO: 339) | JH124_46 | 0 | 0 | 0 | 0 | 0 | 0 |
| CASSPDIQYF (SEQ ID NO: 340) | JH124_51 | 0 | 0 | 0 | 0 | 0 | 0 |
| CASSETGWGAFF (SEQ ID NO: 341) | JH124_34 | 0 | 0 | 0 | 0.268577 | 0 | 0 |
| CASRRHSNQPQHF (SEQ ID NO: 342) | JH124_52 | 0 | 0 | 0 | 0 | 0 | 0 |
| CASSLVGLAGNEQFF (SEQ ID NO: 343) | JH124_52 | 0 | 0 | 0 | 0 | 0 | 0 |
| CASSPQDQHVYEQYF (SEQ ID NO: 344) | JH124_52 | 0 | 0 | 0 | 0 | 0 | 0 |
| CASTLRVDTEAFF (SEQ ID NO: 345) | JH124_58 | 0 | 0 | 0 | 0 | 0 | 0 |

TABLE 6-continued

| | condition | JH124_48_ percent | JH124_43_ percent | JH124_55_ percent | JH124_59_ percent | JH124_18_ percent | JH124_44_ percent |
|---|---|---|---|---|---|---|---|
| CASSGQGGVSEKLFF (SEQ ID NO: 318) | JH124_04 | 0.067935 | 0.049044 | 0.027226 | 0.116212 | 0 | 0 |
| CASSLTGGYTGELFF (SEQ ID NO: 319) | JH124_07 | 0 | 0 | 0 | 0 | 0 | 0 |
| CASSLRSSSETQYF (SEQ ID NO: 320) | JH124_07 | 0 | 0 | 0 | 0 | 0 | 0 |
| CASSLQAGSSYNEQFF (SEQ ID NO: 321) | JH124_63 | 0 | 0 | 0 | 0 | 0 | 0 |
| CASSPSGGSLYNEQFF (SEQ ID NO: 322) | JH124_63 | 0 | 0 | 0 | 0 | 0 | 0 |
| CASSGGISNTEAFF (SEQ ID NO: 323) | JH124_35 | 0 | 0 | 0 | 0 | 0 | 0 |
| CATSTLPSGGEGYEQYF (SEQ ID NO: 324) | JH124_54 | 0 | 0 | 0 | 0 | 0 | 0 |
| CASSGTTYGYTF (SEQ ID NO: 325) | JH124_09 | 0 | 0 | 0 | 0 | 0 | 0 |
| CSASRGLSGYTF (SEQ ID NO: 326) | JH124_53 | 0 | 0 | 0 | 0 | 0 | 0 |
| LGPGTFTSYEQYF (SEQ ID NO: 327) | JH124_28 | 0 | 0 | 0 | 0 | 0 | 0 |
| CASSTGTGFGEQYF (SEQ ID NO: 328) | JH124_57 | 0 | 0 | 0 | 0 | 0 | 0 |
| CASSEGGSDEQYF (SEQ ID NO: 329) | JH124_25 | 0 | 0 | 0 | 0 | 0 | 0 |
| CASSLDPRSSYNSPLHF (SEQ ID NO: 330) | JH124_33 | 0 | 0 | 0 | 0 | 0 | 0 |
| CASTAGTVHSNQPQHF (SEQ ID NO: 331) | JH124_55 | 0 | 0.049044 | 4.546692 | 0 | 0 | 0 |
| CASRDTRELNTEAFF (SEQ ID NO: 332) | JH124_59 | 0 | 0 | 0 | 3.166764 | 0 | 0 |
| CASSLGDLRGFTEAFF (SEQ ID NO: 333) | JH124_59 | 0 | 0 | 0 | 2.93434 | 0 | 0 |
| CATSDLVARDEQFF (SEQ ID NO: 334) | JH124_18 | 0 | 0 | 0 | 0 | 1.067236 | 0 |

TABLE 6-continued

| | | | | | | | |
|---|---|---|---|---|---|---|---|
| CASSYRGTGGGGYTF (SEQ ID NO: 335) | JH124_08 | 0 | 0 | 0 | 0 | 0 | 0 |
| CASSLQGGMGNQPQHF (SEQ ID NO: 336) | JH124_30 | 0 | 0 | 0 | 0 | 0 | 0 |
| CASSLGLGDEQFF (SEQ ID NO: 337) | JH124_30 | 0 | 0 | 0 | 0 | 0 | 0 |
| CASFRQVNYGYTF (SEQ ID NO: 338) | JH124_30 | 0 | 0 | 0 | 0 | 0 | 0 |
| CASSFRQGSYEQYF (SEQ ID NO: 339) | JH124_46 | 0 | 0 | 0 | 0 | 0 | 0 |
| CASSPDIQYF (SEQ ID NO: 340) | JH124_51 | 0 | 0 | 0 | 0 | 0 | 0 |
| CASSETGWGAFF (SEQ ID NO: 341) | JH124_34 | 0.271739 | 0.049044 | 0 | 0.029053 | 0.106724 | 0 |
| CASRRHSNQPQHF (SEQ ID NO: 342) | JH124_52 | 0 | 0 | 0 | 0 | 0 | 0 |
| CASSLVGLAGNEQFF (SEQ ID NO: 343) | JH124_52 | 0 | 0 | 0 | 0 | 0 | 0 |
| CASSPQDQHVYEQYF (SEQ ID NO: 344) | JH124_52 | 0 | 0 | 0 | 0 | 0 | 0 |
| CASTLRVDTEAFF (SEQ ID NO: 345) | JH124_58 | 0 | 0 | 0 | 0 | 0 | 0 |

| | condition | JH124_56_ percent | JH124_08_ percent | JH124_29_ percent | JH124_30_ percent | JH124_46_ percent | JH124_20_ percent |
|---|---|---|---|---|---|---|---|
| CASSGQGGVSEKLFF (SEQ ID NO: 318) | JH124_04 | 0 | 0 | 0 | 0 | 0 | 0 |
| CASSLTGGYTGELFF (SEQ ID NO: 319) | JH124_07 | 0.055177 | 0 | 0.098814 | 0 | 0 | 0 |
| CASSLRSSSETQYF (SEQ ID NO: 320) | JH124_07 | 0 | 0 | 0 | 0 | 0 | 0 |
| CASSLQAGSSYNEQFF (SEQ ID NO: 321) | JH124_63 | 0 | 0 | 0 | 0 | 0 | 0 |
| CASSPSGGSLYNEQFF (SEQ ID NO: 322) | JH124_63 | 0 | 0 | 0 | 0 | 0 | 0 |

TABLE 6-continued

| | | | | | | | |
|---|---|---|---|---|---|---|---|
| CASSGGISNTEAFF (SEQ ID NO: 323) | JH124_35 | 0 | 0 | 0 | 0 | 0 | 0 |
| CATSTLPSGGEGYEQYF (SEQ ID NO: 324) | JH124_54 | 0 | 0 | 0 | 0 | 0 | 0 |
| CASSGTTYGYTF (SEQ ID NO: 325) | JH124_09 | 0 | 0 | 0 | 0 | 0 | 0 |
| CSASRGLSGYTF (SEQ ID NO: 326) | JH124_53 | 0 | 0 | 0 | 0 | 0 | 0 |
| LGPGTFTSYEQYF (SEQ ID NO: 327) | JH124_28 | 0 | 0 | 0 | 0 | 0 | 0 |
| CASSTGTGFGEQYF (SEQ ID NO: 328) | JH124_57 | 0 | 0 | 0 | 0 | 0 | 0 |
| CASSEGGSDEQYF (SEQ ID NO: 329) | JH124_25 | 0 | 0 | 0 | 0 | 0 | 0 |
| CASSLDPRSSYNSPLHF (SEQ ID NO: 330) | JH124_33 | 0 | 0 | 0 | 0 | 0 | 0 |
| CASTAGTVHSNQPQHF (SEQ ID NO: 331) | JH124_55 | 0 | 0 | 0 | 0 | 0 | 0 |
| CASRDTRELNTEAFF (SEQ ID NO: 332) | JH124_59 | 0 | 0 | 0 | 0 | 0 | 0 |
| CASSLGDLRGFTEAFF (SEQ ID NO: 333) | JH124_59 | 0 | 0 | 0 | 0 | 0 | 0 |
| CATSDLVARDEQFF (SEQ ID NO: 334) | JH124_18 | 0 | 0 | 0 | 0 | 0 | 0 |
| CASSYRGTGGGGYTF (SEQ ID NO: 335) | JH124_08 | 0.018392 | 6.757391 | 0 | 0 | 0 | 0 |
| CASSLQGGMGNQPQHF (SEQ ID NO: 336) | JH124_30 | 0 | 0 | 0 | 2.060222 | 0 | 0 |
| CASSLGLGDEQFF (SEQ ID NO: 337) | JH124_30 | 0 | 0 | 0 | 1.003698 | 0 | 0 |
| CASFRQVNYGYTF (SEQ ID NO: 338) | JH124_30 | 0 | 0 | 0 | 0.633914 | 0 | 0 |
| CASSFRQGSYEQYF (SEQ ID NO: 340) | JH124_46 | 0 | 0 | 0 | 0 | 2.004008 | 0 |
| CASSPDIQYF (SEQ ID NO: 341) | JH124_51 | 0 | 0 | 0 | 0 | 0 | 0 |

TABLE 6-continued

| | | | | | | | |
|---|---|---|---|---|---|---|---|
| CASSETGWGAFF (SEQ ID NO: 342) | JH124_34 | 0 | 0.046926 | 0 | 0.052826 | 0 | 0 |
| CASRRHSNQPQHF (SEQ ID NO: 343) | JH124_52 | 0 | 0 | 0 | 0 | 0 | 0 |
| CASSLVGLAGNEQFF (SEQ ID NO: 344) | JH124_52 | 0 | 0 | 0 | 0 | 0 | 0 |
| CASSPQDQHVYEQYF (SEQ ID NO: 345) | JH124_52 | 0 | 0 | 0 | 0 | 0 | 0 |
| CASTLRVDTEAFF (SEQ ID NO: 346) | JH124_58 | 0 | 0 | 0 | 0 | 0 | 0 |

| | condition | JH124_23_ percent | JH124_51_ percent | JH124_34_ percent | JH124_52_ percent | JH124_58_ percent |
|---|---|---|---|---|---|---|
| CASSGQGGVSEKLFF (SEQ ID NO: 318) | JH124_04 | 0 | 0 | 0 | 0 | 0 |
| CASSLTGGYTGELFF (SEQ ID NO: 319) | JH124_07 | 0.177305 | 0 | 0.039479 | 0.02764 | 0 |
| CASSLRSSSETQYF (SEQ ID NO: 320) | JH124_07 | 0 | 0 | 0 | 0 | 0 |
| CASSLQAGSSYNEQFF (SEQ ID NO: 321) | JH124_63 | 0 | 0 | 0 | 0 | 0 |
| CASSPSGGSLYNEQFF (SEQ ID NO: 322) | JH124_63 | 0 | 0 | 0 | 0 | 0 |
| CASSGGISNTEAFF (SEQ ID NO: 323) | JH124_35 | 0 | 0 | 0 | 0 | 0 |
| CATSTLPSGGEGYEQYF (SEQ ID NO: 324) | JH124_54 | 0 | 0 | 0 | 0 | 0 |
| CASSGTTYGYTF (SEQ ID NO: 325) | JH124_09 | 0 | 0 | 0 | 0 | 0 |
| CSASRGLSGYTF (SEQ ID NO: 326) | JH124_53 | 0 | 0 | 0 | 0 | 0 |
| LGPGTFTSYEQYF (SEQ ID NO: 327) | JH124_28 | 0 | 0 | 0 | 0 | 0 |
| CASSTGTGFGEQYF (SEQ ID NO: 328) | JH124_57 | 0 | 0 | 0 | 0 | 0 |

TABLE 6-continued

| | | | | | | |
|---|---|---|---|---|---|---|
| CASSEGGSDEQYF (SEQ ID NO: 329) | JH124_25 | 0 | 0 | 0 | 0 | 0 |
| CASSLDPRSSYNSPLHF (SEQ ID NO: 330) | JH124_33 | 0 | 0 | 0 | 0 | 0 |
| CASTAGTVHSNQPQHF (SEQ ID NO: 331) | JH124_55 | 0 | 0 | 0 | 0 | 0 |
| CASRDTRELNTEAFF (SEQ ID NO: 332) | JH124_59 | 0 | 0 | 0 | 0 | 0 |
| CASSLGDLRGFTEAFF (SEQ ID NO: 333) | JH124_59 | 0 | 0 | 0 | 0 | 0 |
| CATSDLVARDEQFF (SEQ ID NO: 334) | JH124_18 | 0 | 0 | 0 | 0 | 0 |
| CASSYRGTGGGGYTF (SEQ ID NO: 335) | JH124_08 | 0 | 0 | 0 | 0.055279 | 0 |
| CASSLQGGMGNQPQHF (SEQ ID NO: 336) | JH124_30 | 0 | 0.222816 | 0 | 0.055279 | 0 |
| CASSLGLGDEQFF (SEQ ID NO: 337) | JH124_30 | 0 | 0 | 0 | 0 | 0 |
| CASFRQVNYGYTF (SEQ ID NO: 338) | JH124_30 | 0 | 0 | 0 | 0 | 0 |
| CASSFRQGSYEQYF (SEQ ID NO: 339) | JH124_46 | 0 | 0 | 0 | 0 | 0 |
| CASSPDIQYF (SEQ ID NO: 340) | JH124_51 | 0 | 0.668449 | 0 | 0 | 0 |
| CASSETGWGAFF (SEQ ID NO: 341) | JH124_34 | 0 | 0.089127 | 3.039874 | 0.082919 | 0.076628 |
| CASRRHSNQPQHF (SEQ ID NO: 342) | JH124_52 | 0 | 0 | 0 | 4.339414 | 0 |
| CASSLVGLAGNEQFF (SEQ ID NO: 343) | JH124_52 | 0 | 0.311943 | 0 | 1.768933 | 0 |
| CASSPQDQHVYEQYF (SEQ ID NO: 344) | JH124_52 | 0 | 0 | 0 | 0.801548 | 0 |
| CASTLRVDTEAFF (SEQ ID NO: 345) | JH124_58 | 0 | 0 | 0 | 0 | 3.218391 |

TABLE 6-continued

| | condition | JH124_PBMC_2w_percent | JH124_PBMC_10w_percent | JH124_PBMC4w_percent | JH124_PBMC_PreRx_percent | JH124_Tumor percent |
|---|---|---|---|---|---|---|
| CASSGQGGVSEKLFF (SEQ ID NO: 318) | JH124_04 | 0 | 0 | 0 | 0 | 0 |
| CASSLTGGYTGELFF (SEQ ID NO: 319) | JH124_07 | 0.0259175 | 0.002950636 | 0.015061148 | 0.0032341 | 0.520833 |
| CASSLRSSSETQYF (SEQ ID NO: 320) | JH124_07 | 0 | 0 | 0 | 0 | 0 |
| CASSLQAGSSYNEQFF (SEQ ID NO: 321) | JH124_63 | 0 | 0 | 0 | 0 | 0 |
| CASSPSGGSLYNEQFF (SEQ ID NO: 322) | JH124_63 | 0 | 0 | 0 | 0 | 0 |
| CASSGGISNTEAFF (SEQ ID NO: 323) | JH124_35 | 0 | 0 | 0 | 0 | 0 |
| CATSTLPSGGEGYEQYF (SEQ ID NO: 324) | JH124_54 | 0 | 0 | 0 | 0 | 0 |
| CASSGTTYGYTF (SEQ ID NO: 325) | JH124_09 | 0.020734 | 0.019916792 | 0.015061148 | 0.014553452 | 0 |
| CSASRGLSGYTF (SEQ ID NO: 326) | JH124_53 | 0 | 0 | 0 | 0 | 0 |
| LGPGTFTSYEQYF (SEQ ID NO: 327) | JH124_28 | 0 | 0 | 0.004518344 | 0.004851151 | 0 |
| CASSTGTGFGEQYF (SEQ ID NO: 328) | JH124_57 | 0 | 0 | 0 | 0 | 0 |
| CASSEGGSDEQYF (SEQ ID NO: 329) | JH124_25 | 0 | 0 | 0 | 0 | 0 |
| CASSLDPRSSYNSPLHF (SEQ ID NO: 330) | JH124_33 | 0 | 0 | 0 | 0 | 0 |
| CASTAGTVHSNQPQHF (SEQ ID NO: 331) | JH124_55 | 0 | 0 | 0 | 0 | 0 |
| CASRDTRELNTEAFF (SEQ ID NO: 332) | JH124_59 | 0 | 0 | 0 | 0 | 0 |
| CASSLGDLRGFTEAFF (SEQ ID NO: 333) | JH124_59 | 0 | 0 | 0 | 0 | 0 |
| CATSDLVARDEQFF (SEQ ID NO: 334) | JH124_18 | 0 | 0 | 0 | 0 | 0 |

TABLE 6-continued

| | | | | | | |
|---|---|---|---|---|---|---|
| CASSYRGTGGGGYTF (SEQ ID NO: 335) | JH124_08 | 0 | 0 | 0 | 0 | 0 |
| CASSLQGGMGNQPQHF (SEQ ID NO: 336) | JH124_30 | 0 | 0.008114249 | 0.010542804 | 0.0032341 | 0 |
| CASSLGLGDEQFF (SEQ ID NO: 337) | JH124_30 | 0 | 0.001475318 | 0 | 0.0032341 | 0 |
| CASFRQVNYGYTF (SEQ ID NO: 338) | JH124_30 | 0 | 0 | 0 | 0 | 0 |
| CASSFRQGSYEQYF (SEQ ID NO: 339) | JH124_46 | 0 | 0 | 0 | 0 | 0 |
| CASSPDIQYF (SEQ ID NO: 340) | JH124_51 | 0 | 0 | 0 | 0 | 0 |
| CASSETGWGAFF (SEQ ID NO: 341) | JH124_34 | 0 | 0 | 0 | 0 | 0 |
| CASRRHSNQPQHF (SEQ ID NO: 342) | JH124_52 | 0 | 0 | 0 | 0 | 0 |
| CASSLVGLAGNEQFF (SEQ ID NO: 343) | JH124_52 | 0 | 0 | 0 | 0 | 0 |
| CASSPQDQHVYEQYF (SEQ ID NO: 344) | JH124_52 | 0 | 0 | 0 | 0 | 0 |
| CASTLRVDTEAFF (SEQ ID NO: 345) | JH124_58 | 0 | 0 | 0 | 0 | 0 |

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of functionally evaluating a candidate tumor antigen for the ability to induce a T cell response in a subject comprising:

performing next generation sequencing on pre-treatment tumor and matched normal samples;

identifying somatic mutations in matched tumor and normal samples;

wherein (1) distinct paired reads contained the mutation in the tumor; (2) fraction of distinct paired reads containing a particular mutation in the tumor comprise at least 10% of the total distinct read pairs and (3) mismatched bases are not present in >1% of the reads in the matched normal sample nor databases of common germline variants derived from dbSNP and (4) position of the mutation is covered in both the tumor and normal sample;

inputting exome data into a neoantigen prediction pipeline to generate candidate tumor mutation associated neoantigens (MANAs), wherein the neoantigen prediction pipeline assesses immunogenicity of a candidate tumor MANA antigen by analyzing exome data combined with the subject's HLA class I haplotype utilizing a neoantigen prediction platform for evaluating binding of somatic peptides to class I HLA, antigen processing, self-similarity, MHC presentation, and gene expression to generate candidate antigens;

culturing autologous T cells from the subject with the candidate tumor MANA antigen, said candidate tumor MANA antigen comprising a peptide or a protein, in order to stimulate expansion of the T cells;

isolating deoxyribonucleic acid (DNA) from bulk T cells from the culture;

amplifying and sequencing T cell receptor-β (TCR-β) complementarity-determining region 3 (CDR3) DNA to determine frequencies of Vβ CDR23 clonotypes in the bulk T cells;

comparing the frequencies of the Vβ CDR3 clonotypes in the bulk T cells to Vβ CDR3 clonality in T cells cultured in the absence of the candidate tumor MANA antigen and/or in uncultured T cells to identify antigen specific Vβ CDR3 clonotypes;

determining that the candidate tumor MANA antigen has the ability to induce a T cell response if the frequency of antigen specific Vβ CDR3 clonotypes identified in the bulk T cells is higher than the frequency in the T cells cultured in the absence of the candidate tumor MANA antigen and/or uncultured T cells; and incorporating the candidate tumor MANA antigen determined to have the ability to induce a T cell response into an immunogenic treatment composition.

2. The method of claim 1, wherein the autologous T cells from the subject are stimulated to expand with the candidate tumor MANA antigen, said candidate antigen comprising a peptide or whole protein.

3. The method of claim 1, wherein the sample comprises a blood sample or a tumor infiltrating lymphocyte population.

4. The method of claim 1, wherein the subject is a human.

5. The method of claim 1 further comprising sorting CD8+ T cells after culture and expansion of said autologous T cells with said candidate MANA antigen, and wherein the DNA is isolated from bulk CD8+ T cell from the culture.

* * * * *

SEQUENCE LISTING

```
<160> NUMBER OF SEQ ID NOS: 345

<210> SEQ ID NO 1
<211> LENGTH: 9
<212> TYPE: PRT
<213> ORGANISM: Alphainfluenzavirus influenzae

<400> SEQUENCE: 1

Gly Ile Leu Gly Phe Val Phe Thr Leu
1               5


<210> SEQ ID NO 2
<211> LENGTH: 9
<212> TYPE: PRT
<213> ORGANISM: Alphainfluenzavirus influenzae

<400> SEQUENCE: 2

Phe Met Tyr Ser Asp Phe His Phe Ile
1               5


<210> SEQ ID NO 3
<211> LENGTH: 9
<212> TYPE: PRT
<213> ORGANISM: Lymphocryptovirus humangamma4

<400> SEQUENCE: 3

Cys Leu Gly Gly Leu Leu Thr Met Val
1               5


<210> SEQ ID NO 4
<211> LENGTH: 9
<212> TYPE: PRT
<213> ORGANISM: Lymphocryptovirus humangamma4

<400> SEQUENCE: 4

Gly Leu Cys Thr Leu Val Ala Met Leu
1               5


<210> SEQ ID NO 5
<211> LENGTH: 9
<212> TYPE: PRT
<213> ORGANISM: Cytomegalovirus humanbeta5

<400> SEQUENCE: 5

Asn Leu Val Pro Met Val Ala Thr Val
1               5


<210> SEQ ID NO 6
<211> LENGTH: 9
<212> TYPE: PRT
<213> ORGANISM: Alphainfluenzavirus influenzae
```

<400> SEQUENCE: 6

Ser Ile Ile Pro Ser Gly Pro Leu Lys
1 5

<210> SEQ ID NO 7
<211> LENGTH: 10
<212> TYPE: PRT
<213> ORGANISM: Lymphocryptovirus humangamma4

<400> SEQUENCE: 7

Ala Val Phe Asp Arg Lys Ser Asp Ala Lys
1 5 10

<210> SEQ ID NO 8
<211> LENGTH: 9
<212> TYPE: PRT
<213> ORGANISM: Lymphocryptovirus humangamma4

<400> SEQUENCE: 8

Ile Val Thr Asp Phe Ser Val Ile Lys
1 5

<210> SEQ ID NO 9
<211> LENGTH: 9
<212> TYPE: PRT
<213> ORGANISM: Lymphocryptovirus humangamma4

<400> SEQUENCE: 9

Ala Thr Ile Gly Thr Ala Met Tyr Lys
1 5

<210> SEQ ID NO 10
<211> LENGTH: 9
<212> TYPE: PRT
<213> ORGANISM: Alphainfluenzavirus influenzae

<400> SEQUENCE: 10

Glu Leu Arg Ser Arg Tyr Trp Ala Ile
1 5

<210> SEQ ID NO 11
<211> LENGTH: 8
<212> TYPE: PRT
<213> ORGANISM: Lymphocryptovirus humangamma4

<400> SEQUENCE: 11

Arg Ala Lys Phe Lys Gln Leu Leu
1 5

<210> SEQ ID NO 12
<211> LENGTH: 9
<212> TYPE: PRT
<213> ORGANISM: Lymphocryptovirus humangamma4

<400> SEQUENCE: 12

Phe Leu Arg Gly Arg Ala Tyr Gly Leu
1 5

<210> SEQ ID NO 13
<211> LENGTH: 9
<212> TYPE: PRT
<213> ORGANISM: Lymphocryptovirus humangamma4

<400> SEQUENCE: 13

```
Gln Ala Lys Trp Arg Leu Gln Thr Leu
1               5


<210> SEQ ID NO 14
<211> LENGTH: 14
<212> TYPE: PRT
<213> ORGANISM: Homo sapiens

<400> SEQUENCE: 14

Cys Ala Ser Ser Leu Thr Ser Ala Thr Gly Glu Leu Phe Phe
1               5                   10


<210> SEQ ID NO 15
<211> LENGTH: 14
<212> TYPE: PRT
<213> ORGANISM: Homo sapiens

<400> SEQUENCE: 15

Cys Ala Ser Ser Leu Thr Ser Ala Ala Gly Glu Leu Phe Phe
1               5                   10


<210> SEQ ID NO 16
<211> LENGTH: 14
<212> TYPE: PRT
<213> ORGANISM: Homo sapiens

<400> SEQUENCE: 16

Cys Ala Ser Ser Pro Thr Ser Ala Thr Gly Glu Leu Phe Phe
1               5                   10


<210> SEQ ID NO 17
<211> LENGTH: 16
<212> TYPE: PRT
<213> ORGANISM: Homo sapiens

<400> SEQUENCE: 17

Cys Ala Ser Ser Leu Lys Gly Thr Arg Asp Gln Glu Thr Gln Tyr Phe
1               5                   10                  15


<210> SEQ ID NO 18
<211> LENGTH: 14
<212> TYPE: PRT
<213> ORGANISM: Homo sapiens

<400> SEQUENCE: 18

Cys Ala Ser Ser Arg His His Asn Lys Glu Thr Gln Tyr Phe
1               5                   10


<210> SEQ ID NO 19
<211> LENGTH: 15
<212> TYPE: PRT
<213> ORGANISM: Homo sapiens

<400> SEQUENCE: 19

Cys Ser Ala Lys Leu Ala Gly Tyr Gln Thr Gly Glu Leu Phe Phe
1               5                   10                  15


<210> SEQ ID NO 20
<211> LENGTH: 14
<212> TYPE: PRT
<213> ORGANISM: Homo sapiens

<400> SEQUENCE: 20

Cys Ser Ala Arg Thr Leu Gly Pro Gly Asp Glu Gln Tyr Phe
```

1 5 10

<210> SEQ ID NO 21
<211> LENGTH: 11
<212> TYPE: PRT
<213> ORGANISM: Homo sapiens

<400> SEQUENCE: 21

Cys Ser Val Glu Ile Gly Gly Glu Gln Tyr Phe
1 5 10

<210> SEQ ID NO 22
<211> LENGTH: 16
<212> TYPE: PRT
<213> ORGANISM: Homo sapiens

<400> SEQUENCE: 22

Cys Ser Val Leu Gly Gly Thr Ser Gly Ala Gln Glu Thr Gln Tyr Phe
1 5 10 15

<210> SEQ ID NO 23
<211> LENGTH: 17
<212> TYPE: PRT
<213> ORGANISM: Homo sapiens

<400> SEQUENCE: 23

Cys Ala Ser Ser Ile Pro Asn Pro Ile Trp His His Gln Pro Gln His
1 5 10 15

Phe

<210> SEQ ID NO 24
<211> LENGTH: 18
<212> TYPE: PRT
<213> ORGANISM: Homo sapiens

<400> SEQUENCE: 24

Cys Ala Ser Ser Lys Ala Thr Ser Ser Gln Ser Arg Ala Asn Val Leu
1 5 10 15

Thr Phe

<210> SEQ ID NO 25
<211> LENGTH: 14
<212> TYPE: PRT
<213> ORGANISM: Homo sapiens

<400> SEQUENCE: 25

Cys Ala Ser Ser Leu Gly Gly Met Asp Tyr Gly Tyr Thr Phe
1 5 10

<210> SEQ ID NO 26
<211> LENGTH: 11
<212> TYPE: PRT
<213> ORGANISM: Homo sapiens

<400> SEQUENCE: 26

Cys Ala Ser Ser Leu Gly Val Gly Tyr Thr Phe
1 5 10

<210> SEQ ID NO 27
<211> LENGTH: 14
<212> TYPE: PRT
<213> ORGANISM: Homo sapiens

<400> SEQUENCE: 27

Cys Ala Ser Ser Leu Arg Gln Gly Thr Thr Glu Ala Phe Phe
1 5 10

<210> SEQ ID NO 28
<211> LENGTH: 13
<212> TYPE: PRT
<213> ORGANISM: Homo sapiens

<400> SEQUENCE: 28

Cys Ser Ala Ser Ala Gly Leu Val Thr Glu Ala Phe Phe
1 5 10

<210> SEQ ID NO 29
<211> LENGTH: 11
<212> TYPE: PRT
<213> ORGANISM: Homo sapiens

<400> SEQUENCE: 29

Cys Ala Arg Gly Gln Gly Asp Gly Tyr Thr Phe
1 5 10

<210> SEQ ID NO 30
<211> LENGTH: 13
<212> TYPE: PRT
<213> ORGANISM: Homo sapiens

<400> SEQUENCE: 30

Cys Ala Ser Asn Arg Glu Pro Asn Ser Pro Leu His Phe
1 5 10

<210> SEQ ID NO 31
<211> LENGTH: 13
<212> TYPE: PRT
<213> ORGANISM: Homo sapiens

<400> SEQUENCE: 31

Cys Ala Ser Gln Leu Gly Leu Gly Tyr Glu Gln Tyr Phe
1 5 10

<210> SEQ ID NO 32
<211> LENGTH: 15
<212> TYPE: PRT
<213> ORGANISM: Homo sapiens

<400> SEQUENCE: 32

Cys Ala Ser Arg Ala Pro Asp Leu Ala Pro Tyr Glu Gln Tyr Phe
1 5 10 15

<210> SEQ ID NO 33
<211> LENGTH: 12
<212> TYPE: PRT
<213> ORGANISM: Homo sapiens

<400> SEQUENCE: 33

Cys Ala Ser Arg Gly Tyr Asp Arg Glu Ala Phe Phe
1 5 10

<210> SEQ ID NO 34
<211> LENGTH: 15
<212> TYPE: PRT
<213> ORGANISM: Homo sapiens

<400> SEQUENCE: 34

Cys Ala Ser Arg Leu Lys Gln Ser Arg Ala Asn Val Leu Thr Phe

```
1               5                   10                  15


<210> SEQ ID NO 35
<211> LENGTH: 13
<212> TYPE: PRT
<213> ORGANISM: Homo sapiens

<400> SEQUENCE: 35

Cys Ala Ser Arg Pro Thr Gly Val Leu Glu Gln Tyr Phe
1               5                   10


<210> SEQ ID NO 36
<211> LENGTH: 15
<212> TYPE: PRT
<213> ORGANISM: Homo sapiens

<400> SEQUENCE: 36

Cys Ala Ser Ser Ala Gln Gly Val Ile Gly Asp Glu Gln Phe Phe
1               5                   10                  15


<210> SEQ ID NO 37
<211> LENGTH: 16
<212> TYPE: PRT
<213> ORGANISM: Homo sapiens

<400> SEQUENCE: 37

Cys Ala Ser Ser Cys Asp His Leu His Ala Arg Asn Thr Ile Tyr Phe
1               5                   10                  15


<210> SEQ ID NO 38
<211> LENGTH: 14
<212> TYPE: PRT
<213> ORGANISM: Homo sapiens

<400> SEQUENCE: 38

Cys Ala Ser Ser Asp Gln Gly Ser Asp Tyr Glu Gln Tyr Phe
1               5                   10


<210> SEQ ID NO 39
<211> LENGTH: 17
<212> TYPE: PRT
<213> ORGANISM: Homo sapiens

<400> SEQUENCE: 39

Cys Ala Ser Ser Phe Gly Leu Ala Gly Leu Lys Thr Gly Glu Leu Phe
1               5                   10                  15

Phe


<210> SEQ ID NO 40
<211> LENGTH: 14
<212> TYPE: PRT
<213> ORGANISM: Homo sapiens

<400> SEQUENCE: 40

Cys Ala Ser Ser Phe Gly Gln Met Asn Thr Glu Ala Phe Phe
1               5                   10


<210> SEQ ID NO 41
<211> LENGTH: 13
<212> TYPE: PRT
<213> ORGANISM: Homo sapiens

<400> SEQUENCE: 41

Cys Ala Ser Ser Phe Gly Ser His Thr Glu Ala Phe Phe
```

1 5 10

<210> SEQ ID NO 42
<211> LENGTH: 13
<212> TYPE: PRT
<213> ORGANISM: Homo sapiens

<400> SEQUENCE: 42

Cys Ala Ser Ser Phe Leu Thr Gln Glu Thr Gln Tyr Phe
1 5 10

<210> SEQ ID NO 43
<211> LENGTH: 15
<212> TYPE: PRT
<213> ORGANISM: Homo sapiens

<400> SEQUENCE: 43

Cys Ala Ser Ser Phe Pro Gly Glu Ala Ser Tyr Glu Gln Tyr Phe
1 5 10 15

<210> SEQ ID NO 44
<211> LENGTH: 14
<212> TYPE: PRT
<213> ORGANISM: Homo sapiens

<400> SEQUENCE: 44

Cys Ala Ser Ser Gly Ala Asp Ser Asn Ser Pro Leu His Phe
1 5 10

<210> SEQ ID NO 45
<211> LENGTH: 13
<212> TYPE: PRT
<213> ORGANISM: Homo sapiens

<400> SEQUENCE: 45

Cys Ala Ser Ser Gly Gly Thr Ala Asp Glu Gln Phe Phe
1 5 10

<210> SEQ ID NO 46
<211> LENGTH: 14
<212> TYPE: PRT
<213> ORGANISM: Homo sapiens

<400> SEQUENCE: 46

Cys Ala Ser Ser Leu Leu Ala Ser Gly Asn Thr Ile Tyr Phe
1 5 10

<210> SEQ ID NO 47
<211> LENGTH: 18
<212> TYPE: PRT
<213> ORGANISM: Homo sapiens

<400> SEQUENCE: 47

Cys Ala Ser Ser Leu Asn Ser Gln Gly Gln Ser Arg Ala Asn Val Leu
1 5 10 15

Thr Phe

<210> SEQ ID NO 48
<211> LENGTH: 17
<212> TYPE: PRT
<213> ORGANISM: Homo sapiens

<400> SEQUENCE: 48

Cys Ala Ser Ser Leu Gln Gly Thr Ser Gly Arg Asp Asn Glu Gln Phe 1 5 10 15

Phe

<210> SEQ ID NO 49
<211> LENGTH: 16
<212> TYPE: PRT
<213> ORGANISM: Homo sapiens

<400> SEQUENCE: 49

Cys Ala Ser Ser Leu Thr Pro Gly Gln Met Asn Thr Glu Ala Phe Phe
1 5 10 15

<210> SEQ ID NO 50
<211> LENGTH: 16
<212> TYPE: PRT
<213> ORGANISM: Homo sapiens

<400> SEQUENCE: 50

Cys Ala Ser Ser Asn Gln Gly Leu Trp His His Gln Pro Gln His Phe
1 5 10 15

<210> SEQ ID NO 51
<211> LENGTH: 14
<212> TYPE: PRT
<213> ORGANISM: Homo sapiens

<400> SEQUENCE: 51

Cys Ala Ser Ser Asn Thr Gly Thr Val Tyr Gly Tyr Thr Phe
1 5 10

<210> SEQ ID NO 52
<211> LENGTH: 14
<212> TYPE: PRT
<213> ORGANISM: Homo sapiens

<400> SEQUENCE: 52

Cys Ala Ser Ser Pro Asp Trp Gly Thr Gly Glu Leu Phe Phe
1 5 10

<210> SEQ ID NO 53
<211> LENGTH: 15
<212> TYPE: PRT
<213> ORGANISM: Homo sapiens

<400> SEQUENCE: 53

Cys Ala Ser Ser Pro Gly Gly Leu Ala Lys Asn Ile Gln Tyr Phe
1 5 10 15

<210> SEQ ID NO 54
<211> LENGTH: 14
<212> TYPE: PRT
<213> ORGANISM: Homo sapiens

<400> SEQUENCE: 54

Cys Ala Ser Ser Pro Gly Thr Ala Asn Gln Pro Gln His Phe
1 5 10

<210> SEQ ID NO 55
<211> LENGTH: 14
<212> TYPE: PRT
<213> ORGANISM: Homo sapiens

<400> SEQUENCE: 55

Cys Ala Ser Ser Gln Asp Gly Gly Thr Tyr Glu Gln Tyr Phe 1 5 10

<210> SEQ ID NO 56
<211> LENGTH: 14
<212> TYPE: PRT
<213> ORGANISM: Homo sapiens

<400> SEQUENCE: 56

Cys Ala Ser Ser Gln Glu Asp Glu Tyr Asn Glu Gln Phe Phe
1 5 10

<210> SEQ ID NO 57
<211> LENGTH: 13
<212> TYPE: PRT
<213> ORGANISM: Homo sapiens

<400> SEQUENCE: 57

Cys Ala Ser Ser Gln Glu Phe Asn Gln Pro Gln His Phe
1 5 10

<210> SEQ ID NO 58
<211> LENGTH: 17
<212> TYPE: PRT
<213> ORGANISM: Homo sapiens

<400> SEQUENCE: 58

Cys Ala Ser Ser Gln His Thr Gln Gln Ser Arg Ala Asn Val Leu Thr
1 5 10 15

Phe

<210> SEQ ID NO 59
<211> LENGTH: 13
<212> TYPE: PRT
<213> ORGANISM: Homo sapiens

<400> SEQUENCE: 59

Cys Ala Ser Ser Gln Gln Glu Thr Tyr Glu Gln Tyr Phe
1 5 10

<210> SEQ ID NO 60
<211> LENGTH: 13
<212> TYPE: PRT
<213> ORGANISM: Homo sapiens

<400> SEQUENCE: 60

Cys Ala Ser Ser Arg Ala Ser Ser Tyr Glu Gln Tyr Phe
1 5 10

<210> SEQ ID NO 61
<211> LENGTH: 18
<212> TYPE: PRT
<213> ORGANISM: Homo sapiens

<400> SEQUENCE: 61

Cys Ala Ser Ser Arg Phe Val Thr Met Thr Ser Arg Ala Asn Val Leu
1 5 10 15

Thr Phe

<210> SEQ ID NO 62
<211> LENGTH: 12
<212> TYPE: PRT
<213> ORGANISM: Homo sapiens

<400> SEQUENCE: 62

Cys Ala Ser Ser Ser Arg Gly Asn Glu Gln Phe Phe
1 5 10

<210> SEQ ID NO 63
<211> LENGTH: 15
<212> TYPE: PRT
<213> ORGANISM: Homo sapiens

<400> SEQUENCE: 63

Cys Ala Ser Ser Thr Leu Gly Gln Leu Asn Thr Glu Ala Phe Phe
1 5 10 15

<210> SEQ ID NO 64
<211> LENGTH: 16
<212> TYPE: PRT
<213> ORGANISM: Homo sapiens

<400> SEQUENCE: 64

Cys Ala Ser Ser Thr Thr Thr Gly Pro Ser Asp Asn Glu Gln Phe Phe
1 5 10 15

<210> SEQ ID NO 65
<211> LENGTH: 12
<212> TYPE: PRT
<213> ORGANISM: Homo sapiens

<400> SEQUENCE: 65

Cys Ala Ser Ser Trp Val Ala Asn Ile Gln Tyr Phe
1 5 10

<210> SEQ ID NO 66
<211> LENGTH: 12
<212> TYPE: PRT
<213> ORGANISM: Homo sapiens

<400> SEQUENCE: 66

Cys Ala Ser Thr Leu Arg Arg Asn Glu Gln Tyr Phe
1 5 10

<210> SEQ ID NO 67
<211> LENGTH: 13
<212> TYPE: PRT
<213> ORGANISM: Homo sapiens

<400> SEQUENCE: 67

Cys Ala Ser Val Gly Pro Pro Asn Tyr Gly Tyr Thr Phe
1 5 10

<210> SEQ ID NO 68
<211> LENGTH: 11
<212> TYPE: PRT
<213> ORGANISM: Homo sapiens

<400> SEQUENCE: 68

Cys Ala Thr Gly Asn Lys Asp Glu Gln Tyr Phe
1 5 10

<210> SEQ ID NO 69
<211> LENGTH: 19
<212> TYPE: PRT
<213> ORGANISM: Homo sapiens

<400> SEQUENCE: 69

Cys Ala Thr Arg Gly Gly Gln Gly Lys Gly Leu Ala Asp Tyr Asn Glu 1 5 10 15

Gln Phe Phe

<210> SEQ ID NO 70
<211> LENGTH: 11
<212> TYPE: PRT
<213> ORGANISM: Homo sapiens

<400> SEQUENCE: 70

Cys Glu Ser Gln Gly Arg Lys Thr Gln Tyr Phe
1 5 10

<210> SEQ ID NO 71
<211> LENGTH: 15
<212> TYPE: PRT
<213> ORGANISM: Homo sapiens

<400> SEQUENCE: 71

Cys Ser Ala Lys Pro Ala Gly Tyr Gln Thr Gly Glu Leu Phe Phe
1 5 10 15

<210> SEQ ID NO 72
<211> LENGTH: 17
<212> TYPE: PRT
<213> ORGANISM: Homo sapiens

<400> SEQUENCE: 72

Cys Ser Ala Arg Glu Gly Gln Gly Arg Ala Arg Gln Glu Thr Gln Tyr
1 5 10 15

Phe

<210> SEQ ID NO 73
<211> LENGTH: 12
<212> TYPE: PRT
<213> ORGANISM: Homo sapiens

<400> SEQUENCE: 73

Cys Ser Ala Ser Ser Asp Lys Asn Ile Gln Tyr Phe
1 5 10

<210> SEQ ID NO 74
<211> LENGTH: 13
<212> TYPE: PRT
<213> ORGANISM: Homo sapiens

<400> SEQUENCE: 74

Cys Ser Ala Thr Ser Gly Tyr Ser Tyr Glu Gln Tyr Phe
1 5 10

<210> SEQ ID NO 75
<211> LENGTH: 11
<212> TYPE: PRT
<213> ORGANISM: Homo sapiens

<400> SEQUENCE: 75

Cys Ser Gly Leu Ser Asp Trp Ala Gln Tyr Phe
1 5 10

<210> SEQ ID NO 76
<211> LENGTH: 14
<212> TYPE: PRT
<213> ORGANISM: Homo sapiens

<400> SEQUENCE: 76

Cys Ser Val Ala Arg Ser Gly Lys Asn Tyr Glu Gln Tyr Phe
1 5 10

<210> SEQ ID NO 77
<211> LENGTH: 16
<212> TYPE: PRT
<213> ORGANISM: Homo sapiens

<400> SEQUENCE: 77

Cys Ser Val Glu Glu Ala Ala Ser Gly Ser Pro Tyr Glu Gln Tyr Phe
1 5 10 15

<210> SEQ ID NO 78
<211> LENGTH: 14
<212> TYPE: PRT
<213> ORGANISM: Homo sapiens

<400> SEQUENCE: 78

Cys Ser Val Gly Thr Gly Gly Thr Asn Glu Lys Leu Phe Phe
1 5 10

<210> SEQ ID NO 79
<211> LENGTH: 13
<212> TYPE: PRT
<213> ORGANISM: Homo sapiens

<400> SEQUENCE: 79

Cys Ser Val Leu Gly Val Leu Asn Thr Glu Ala Phe Phe
1 5 10

<210> SEQ ID NO 80
<211> LENGTH: 13
<212> TYPE: PRT
<213> ORGANISM: Homo sapiens

<400> SEQUENCE: 80

Cys Ser Val Val Leu Gly Ala Gly Tyr Glu Gln Tyr Phe
1 5 10

<210> SEQ ID NO 81
<211> LENGTH: 14
<212> TYPE: PRT
<213> ORGANISM: Homo sapiens

<400> SEQUENCE: 81

Arg Ala Ile Arg Val Gln Gly Asp Trp Thr Glu Ala Phe Phe
1 5 10

<210> SEQ ID NO 82
<211> LENGTH: 15
<212> TYPE: PRT
<213> ORGANISM: Homo sapiens

<400> SEQUENCE: 82

Cys Ala Ile Arg Gly Thr Ser Gly Arg Thr Gly Glu Leu Phe Phe
1 5 10 15

<210> SEQ ID NO 83
<211> LENGTH: 15
<212> TYPE: PRT
<213> ORGANISM: Homo sapiens

<400> SEQUENCE: 83

Cys Ala Ile Ser Gly Asp Ser Ser Gly Ala Asn Val Leu Thr Phe 1 5 10 15

<210> SEQ ID NO 84
<211> LENGTH: 12
<212> TYPE: PRT
<213> ORGANISM: Homo sapiens

<400> SEQUENCE: 84

Cys Ala Ile Ser Pro Gln Val Gly Glu Gln Tyr Phe
1 5 10

<210> SEQ ID NO 85
<211> LENGTH: 12
<212> TYPE: PRT
<213> ORGANISM: Homo sapiens

<400> SEQUENCE: 85

Cys Ala Pro Asn Gly Gly Gly Asn Thr Ile Tyr Phe
1 5 10

<210> SEQ ID NO 86
<211> LENGTH: 14
<212> TYPE: PRT
<213> ORGANISM: Homo sapiens

<400> SEQUENCE: 86

Cys Ala Ser Ala Thr Gly Val Arg Ala Tyr Glu Gln Tyr Phe
1 5 10

<210> SEQ ID NO 87
<211> LENGTH: 13
<212> TYPE: PRT
<213> ORGANISM: Homo sapiens

<400> SEQUENCE: 87

Cys Ala Ser Gly Pro Asp Arg Thr Tyr Glu Gln Tyr Phe
1 5 10

<210> SEQ ID NO 88
<211> LENGTH: 17
<212> TYPE: PRT
<213> ORGANISM: Homo sapiens

<400> SEQUENCE: 88

Cys Ala Ser Gly Pro Phe Pro Arg Asp Ser Ser Tyr Asn Glu Gln Phe
1 5 10 15

Phe

<210> SEQ ID NO 89
<211> LENGTH: 13
<212> TYPE: PRT
<213> ORGANISM: Homo sapiens

<400> SEQUENCE: 89

Cys Ala Ser Gly Gln Gly Asn Gln Asp Thr Gln Tyr Phe
1 5 10

<210> SEQ ID NO 90
<211> LENGTH: 17
<212> TYPE: PRT
<213> ORGANISM: Homo sapiens

<400> SEQUENCE: 90

Cys Ala Ser His Gly Ala Pro Gly Arg Ala Gly Lys Ala Thr Gln Tyr 1 5 10 15

Phe

<210> SEQ ID NO 91
<211> LENGTH: 11
<212> TYPE: PRT
<213> ORGANISM: Homo sapiens

<400> SEQUENCE: 91

Cys Ala Ser Leu Gly Gly Ile Glu Ala Phe Phe
1 5 10

<210> SEQ ID NO 92
<211> LENGTH: 13
<212> TYPE: PRT
<213> ORGANISM: Homo sapiens

<400> SEQUENCE: 92

Cys Ala Ser Met Arg Arg Glu Val Tyr Glu Gln Phe Phe
1 5 10

<210> SEQ ID NO 93
<211> LENGTH: 16
<212> TYPE: PRT
<213> ORGANISM: Homo sapiens

<400> SEQUENCE: 93

Cys Ala Ser Asn Arg Ser Thr Gln Ser Arg Ala Asn Val Leu Thr Phe
1 5 10 15

<210> SEQ ID NO 94
<211> LENGTH: 13
<212> TYPE: PRT
<213> ORGANISM: Homo sapiens

<400> SEQUENCE: 94

Cys Ala Ser Gln Thr Ser Gly Ser Tyr Glu Gln Tyr Phe
1 5 10

<210> SEQ ID NO 95
<211> LENGTH: 16
<212> TYPE: PRT
<213> ORGANISM: Homo sapiens

<400> SEQUENCE: 95

Cys Ala Ser Arg Ala Thr Met Gly Thr Gly Gln Glu Thr Gln Tyr Phe
1 5 10 15

<210> SEQ ID NO 96
<211> LENGTH: 13
<212> TYPE: PRT
<213> ORGANISM: Homo sapiens

<400> SEQUENCE: 96

Cys Ala Ser Arg Asp Gly Asp Thr Gly Glu Leu Phe Phe
1 5 10

<210> SEQ ID NO 97
<211> LENGTH: 13
<212> TYPE: PRT
<213> ORGANISM: Homo sapiens

<400> SEQUENCE: 97

Cys Ala Ser Arg Gly Arg Gln Ala Tyr Glu Gln Tyr Phe 1 5 10

<210> SEQ ID NO 98
<211> LENGTH: 16
<212> TYPE: PRT
<213> ORGANISM: Homo sapiens

<400> SEQUENCE: 98

Cys Ala Ser Arg Arg Ile Arg Glu Leu Leu Thr Asp Thr Gln Tyr Phe
1 5 10 15

<210> SEQ ID NO 99
<211> LENGTH: 15
<212> TYPE: PRT
<213> ORGANISM: Homo sapiens

<400> SEQUENCE: 99

Cys Ala Ser Arg Arg Pro Gly Leu Asp Asn Tyr Gly Tyr Thr Phe
1 5 10 15

<210> SEQ ID NO 100
<211> LENGTH: 15
<212> TYPE: PRT
<213> ORGANISM: Homo sapiens

<400> SEQUENCE: 100

Cys Ala Ser Arg Arg Ser Gly Leu Asp Asn Tyr Gly Tyr Thr Phe
1 5 10 15

<210> SEQ ID NO 101
<211> LENGTH: 14
<212> TYPE: PRT
<213> ORGANISM: Homo sapiens

<400> SEQUENCE: 101

Cys Ala Ser Arg Thr Ala Gly Glu Pro His Glu Gln Tyr Phe
1 5 10

<210> SEQ ID NO 102
<211> LENGTH: 13
<212> TYPE: PRT
<213> ORGANISM: Homo sapiens

<400> SEQUENCE: 102

Cys Ala Ser Ser Ala Gly Leu Asn Thr Glu Ala Phe Phe
1 5 10

<210> SEQ ID NO 103
<211> LENGTH: 13
<212> TYPE: PRT
<213> ORGANISM: Homo sapiens

<400> SEQUENCE: 103

Cys Ala Ser Ser Ala Leu Gly Asn Gln Pro Gln His Phe
1 5 10

<210> SEQ ID NO 104
<211> LENGTH: 15
<212> TYPE: PRT
<213> ORGANISM: Homo sapiens

<400> SEQUENCE: 104

Cys Ala Ser Ser Ala Pro Gly His Val Gly His Gly Tyr Thr Phe
1 5 10 15

<210> SEQ ID NO 105
<211> LENGTH: 15
<212> TYPE: PRT
<213> ORGANISM: Homo sapiens

<400> SEQUENCE: 105

Cys Ala Ser Ser Glu Ala Thr Gly Arg Ser Glu Lys Leu Phe Phe
1               5                   10                  15

<210> SEQ ID NO 106
<211> LENGTH: 14
<212> TYPE: PRT
<213> ORGANISM: Homo sapiens

<400> SEQUENCE: 106

Cys Ala Ser Ser Glu Ser Gly Phe Gly Glu Lys Leu Phe Phe
1               5                   10

<210> SEQ ID NO 107
<211> LENGTH: 15
<212> TYPE: PRT
<213> ORGANISM: Homo sapiens

<400> SEQUENCE: 107

Cys Ala Ser Ser Phe Ala Gly Gly Gly Asn Thr Glu Ala Phe Phe
1               5                   10                  15

<210> SEQ ID NO 108
<211> LENGTH: 16
<212> TYPE: PRT
<213> ORGANISM: Homo sapiens

<400> SEQUENCE: 108

Cys Ala Ser Ser Phe Ala Thr Ser Gly Phe Thr Asp Thr Gln Tyr Phe
1               5                   10                  15

<210> SEQ ID NO 109
<211> LENGTH: 15
<212> TYPE: PRT
<213> ORGANISM: Homo sapiens

<400> SEQUENCE: 109

Cys Ala Ser Ser Phe Asp Gly Ser Leu Asn Thr Glu Ala Phe Phe
1               5                   10                  15

<210> SEQ ID NO 110
<211> LENGTH: 15
<212> TYPE: PRT
<213> ORGANISM: Homo sapiens

<400> SEQUENCE: 110

Cys Ala Ser Ser Phe Gly Asp Ser Ala Tyr Asn Glu Gln Phe Phe
1               5                   10                  15

<210> SEQ ID NO 111
<211> LENGTH: 15
<212> TYPE: PRT
<213> ORGANISM: Homo sapiens

<400> SEQUENCE: 111

Cys Ala Ser Ser Phe Gly Gly Ala His Thr Gly Glu Leu Phe Phe
1               5                   10                  15

<210> SEQ ID NO 112

<211> LENGTH: 15
<212> TYPE: PRT
<213> ORGANISM: Homo sapiens

<400> SEQUENCE: 112

Cys Ala Ser Ser Phe Lys Asn Arg Ile Gly Thr Glu Ala Phe Phe
1 5 10 15

<210> SEQ ID NO 113
<211> LENGTH: 17
<212> TYPE: PRT
<213> ORGANISM: Homo sapiens

<400> SEQUENCE: 113

Cys Ala Ser Ser Phe Leu Leu His Met Ile Ser Thr Asp Thr Gln Tyr
1 5 10 15

Phe

<210> SEQ ID NO 114
<211> LENGTH: 15
<212> TYPE: PRT
<213> ORGANISM: Homo sapiens

<400> SEQUENCE: 114

Cys Ala Ser Ser Phe Arg Thr Ser Gly Ile Asp Thr Gln Tyr Phe
1 5 10 15

<210> SEQ ID NO 115
<211> LENGTH: 15
<212> TYPE: PRT
<213> ORGANISM: Homo sapiens

<400> SEQUENCE: 115

Cys Ala Ser Ser Gly Gly Gly Ser Gly Ser Asp Thr Gln Tyr Phe
1 5 10 15

<210> SEQ ID NO 116
<211> LENGTH: 12
<212> TYPE: PRT
<213> ORGANISM: Homo sapiens

<400> SEQUENCE: 116

Cys Ala Ser Ser Ile Gly Leu Leu Glu Gln Phe Phe
1 5 10

<210> SEQ ID NO 117
<211> LENGTH: 18
<212> TYPE: PRT
<213> ORGANISM: Homo sapiens

<400> SEQUENCE: 117

Cys Ala Ser Ser Ile Val Asp Pro Ile Ile His His Asn Ser Pro Leu
1 5 10 15

His Phe

<210> SEQ ID NO 118
<211> LENGTH: 17
<212> TYPE: PRT
<213> ORGANISM: Homo sapiens

<400> SEQUENCE: 118

Cys Ala Ser Ser Ile Val Gly Ser Trp Gly Ser Asn Gln Pro Gln His
1 5 10 15

Phe

<210> SEQ ID NO 119
<211> LENGTH: 18
<212> TYPE: PRT
<213> ORGANISM: Homo sapiens

<400> SEQUENCE: 119

Cys Ala Ser Ser Lys Gly His Pro Phe His Thr Tyr Asn Ser Pro Leu
1 5 10 15

His Phe

<210> SEQ ID NO 120
<211> LENGTH: 13
<212> TYPE: PRT
<213> ORGANISM: Homo sapiens

<400> SEQUENCE: 120

Cys Ala Ser Ser Leu Asp Asn Ser Tyr Glu Gln Tyr Phe
1 5 10

<210> SEQ ID NO 121
<211> LENGTH: 14
<212> TYPE: PRT
<213> ORGANISM: Homo sapiens

<400> SEQUENCE: 121

Cys Ala Ser Ser Leu Asp Arg Ala Gly Gln Pro Gln His Phe
1 5 10

<210> SEQ ID NO 122
<211> LENGTH: 15
<212> TYPE: PRT
<213> ORGANISM: Homo sapiens

<400> SEQUENCE: 122

Cys Ala Ser Ser Leu Glu Ala Gly Ser Tyr Asn Glu Gln Phe Phe
1 5 10 15

<210> SEQ ID NO 123
<211> LENGTH: 15
<212> TYPE: PRT
<213> ORGANISM: Homo sapiens

<400> SEQUENCE: 123

Cys Ala Ser Ser Leu Glu Leu Ala Ser Ser Tyr Glu Gln Tyr Phe
1 5 10 15

<210> SEQ ID NO 124
<211> LENGTH: 13
<212> TYPE: PRT
<213> ORGANISM: Homo sapiens

<400> SEQUENCE: 124

Cys Ala Ser Ser Leu Gly Ala Glu Trp Glu Gln Tyr Phe
1 5 10

<210> SEQ ID NO 125
<211> LENGTH: 14
<212> TYPE: PRT
<213> ORGANISM: Homo sapiens

<400> SEQUENCE: 125

Cys Ala Ser Ser Leu Gly Leu Gly Tyr Tyr Gly Tyr Thr Phe 1 5 10

<210> SEQ ID NO 126
<211> LENGTH: 13
<212> TYPE: PRT
<213> ORGANISM: Homo sapiens

<400> SEQUENCE: 126

Cys Ala Ser Ser Leu Gly Arg Gly Leu Glu Gln Tyr Phe
1 5 10

<210> SEQ ID NO 127
<211> LENGTH: 16
<212> TYPE: PRT
<213> ORGANISM: Homo sapiens

<400> SEQUENCE: 127

Cys Ala Ser Ser Leu Gly Arg Trp Glu Arg Gly Glu Thr Gln Tyr Phe
1 5 10 15

<210> SEQ ID NO 128
<211> LENGTH: 16
<212> TYPE: PRT
<213> ORGANISM: Homo sapiens

<400> SEQUENCE: 128

Cys Ala Ser Ser Leu Gly Val Asp Gly Leu Ala Tyr Glu Gln Tyr Phe
1 5 10 15

<210> SEQ ID NO 129
<211> LENGTH: 15
<212> TYPE: PRT
<213> ORGANISM: Homo sapiens

<400> SEQUENCE: 129

Cys Ala Ser Ser Leu Gly Val Ser Pro Thr Asp Thr Gln Tyr Phe
1 5 10 15

<210> SEQ ID NO 130
<211> LENGTH: 15
<212> TYPE: PRT
<213> ORGANISM: Homo sapiens

<400> SEQUENCE: 130

Cys Ala Ser Ser Leu Leu Gly Asn Ser Tyr Asn Glu Gln Phe Phe
1 5 10 15

<210> SEQ ID NO 131
<211> LENGTH: 15
<212> TYPE: PRT
<213> ORGANISM: Homo sapiens

<400> SEQUENCE: 131

Cys Ala Ser Ser Leu Pro Pro Thr Gly Gln Glu Thr Gln Tyr Phe
1 5 10 15

<210> SEQ ID NO 132
<211> LENGTH: 16
<212> TYPE: PRT
<213> ORGANISM: Homo sapiens

<400> SEQUENCE: 132

Cys Ala Ser Ser Leu Ser Arg Gly Ala Arg Thr Tyr Glu Gln Tyr Phe
1 5 10 15

<210> SEQ ID NO 133
<211> LENGTH: 14
<212> TYPE: PRT
<213> ORGANISM: Homo sapiens

<400> SEQUENCE: 133

Cys Ala Ser Ser Leu Val Val Glu Ser Tyr Glu Gln Tyr Phe
1 5 10

<210> SEQ ID NO 134
<211> LENGTH: 16
<212> TYPE: PRT
<213> ORGANISM: Homo sapiens

<400> SEQUENCE: 134

Cys Ala Ser Ser Pro Asp Phe Gly Arg Leu Ser Tyr Glu Gln Tyr Phe
1 5 10 15

<210> SEQ ID NO 135
<211> LENGTH: 15
<212> TYPE: PRT
<213> ORGANISM: Homo sapiens

<400> SEQUENCE: 135

Cys Ala Ser Ser Pro Phe Gly Arg Gly Gln Asp Thr Gln Tyr Phe
1 5 10 15

<210> SEQ ID NO 136
<211> LENGTH: 13
<212> TYPE: PRT
<213> ORGANISM: Homo sapiens

<400> SEQUENCE: 136

Cys Ala Ser Ser Pro Gly Glu Thr Tyr Glu Gln Tyr Phe
1 5 10

<210> SEQ ID NO 137
<211> LENGTH: 16
<212> TYPE: PRT
<213> ORGANISM: Homo sapiens

<400> SEQUENCE: 137

Cys Ala Ser Ser Pro Gly Gly Gln Pro Phe Gly Tyr Glu Gln Tyr Phe
1 5 10 15

<210> SEQ ID NO 138
<211> LENGTH: 12
<212> TYPE: PRT
<213> ORGANISM: Homo sapiens

<400> SEQUENCE: 138

Cys Ala Ser Ser Pro Gly Ile Ser Glu Gln Tyr Phe
1 5 10

<210> SEQ ID NO 139
<211> LENGTH: 15
<212> TYPE: PRT
<213> ORGANISM: Homo sapiens

<400> SEQUENCE: 139

Cys Ala Ser Ser Pro Pro Gly Gly Val Lys Glu Lys Leu Phe Phe
1 5 10 15

<210> SEQ ID NO 140

<211> LENGTH: 13
<212> TYPE: PRT
<213> ORGANISM: Homo sapiens

<400> SEQUENCE: 140

Cys Ala Ser Ser Pro Pro Asn Thr Gly Glu Leu Phe Phe
1 5 10

<210> SEQ ID NO 141
<211> LENGTH: 12
<212> TYPE: PRT
<213> ORGANISM: Homo sapiens

<400> SEQUENCE: 141

Cys Ala Ser Ser Pro Arg Gly Thr Glu Ala Phe Phe
1 5 10

<210> SEQ ID NO 142
<211> LENGTH: 17
<212> TYPE: PRT
<213> ORGANISM: Homo sapiens

<400> SEQUENCE: 142

Cys Ala Ser Ser Pro Arg Thr Arg Gly Gly Gly Leu Asn Glu Gln Phe
1 5 10 15

Phe

<210> SEQ ID NO 143
<211> LENGTH: 11
<212> TYPE: PRT
<213> ORGANISM: Homo sapiens

<400> SEQUENCE: 143

Cys Ala Ser Ser Pro Ser Gly Gly Leu Tyr Phe
1 5 10

<210> SEQ ID NO 144
<211> LENGTH: 15
<212> TYPE: PRT
<213> ORGANISM: Homo sapiens

<400> SEQUENCE: 144

Cys Ala Ser Ser Pro Ser Gly Gly Asn Asn Tyr Glu Gln Tyr Phe
1 5 10 15

<210> SEQ ID NO 145
<211> LENGTH: 16
<212> TYPE: PRT
<213> ORGANISM: Homo sapiens

<400> SEQUENCE: 145

Cys Ala Ser Ser Pro Ser Pro Gly Gln Leu Thr Tyr Glu Gln Tyr Phe
1 5 10 15

<210> SEQ ID NO 146
<211> LENGTH: 13
<212> TYPE: PRT
<213> ORGANISM: Homo sapiens

<400> SEQUENCE: 146

Cys Ala Ser Ser Pro Trp Thr Gly Ser Glu Gln Tyr Phe
1 5 10

<210> SEQ ID NO 147

<211> LENGTH: 14
<212> TYPE: PRT
<213> ORGANISM: Homo sapiens

<400> SEQUENCE: 147

Cys Ala Ser Ser Gln Ala Ala Gly Asp Gln Pro Gln His Phe
1 5 10

<210> SEQ ID NO 148
<211> LENGTH: 17
<212> TYPE: PRT
<213> ORGANISM: Homo sapiens

<400> SEQUENCE: 148

Cys Ala Ser Ser Gln Asp Leu Arg Gly Thr Arg Lys Asn Ile Gln Tyr
1 5 10 15

Phe

<210> SEQ ID NO 149
<211> LENGTH: 14
<212> TYPE: PRT
<213> ORGANISM: Homo sapiens

<400> SEQUENCE: 149

Cys Ala Ser Ser Gln Gly Arg Asp Ala Tyr Glu Gln Tyr Phe
1 5 10

<210> SEQ ID NO 150
<211> LENGTH: 13
<212> TYPE: PRT
<213> ORGANISM: Homo sapiens

<400> SEQUENCE: 150

Cys Ala Ser Ser Gln Lys Arg Asp Tyr Glu Gln Tyr Phe
1 5 10

<210> SEQ ID NO 151
<211> LENGTH: 16
<212> TYPE: PRT
<213> ORGANISM: Homo sapiens

<400> SEQUENCE: 151

Cys Ala Ser Ser Gln Leu Thr Ser Gly Asp Tyr Asn Glu Gln Phe Phe
1 5 10 15

<210> SEQ ID NO 152
<211> LENGTH: 14
<212> TYPE: PRT
<213> ORGANISM: Homo sapiens

<400> SEQUENCE: 152

Cys Ala Ser Ser Gln Arg Asp Pro Asn Ser Pro Leu His Phe
1 5 10

<210> SEQ ID NO 153
<211> LENGTH: 16
<212> TYPE: PRT
<213> ORGANISM: Homo sapiens

<400> SEQUENCE: 153

Cys Ala Ser Ser Arg Ala Ile Ala Thr Ile Arg Thr Glu Ala Phe Phe
1 5 10 15

<210> SEQ ID NO 154

<211> LENGTH: 15
<212> TYPE: PRT
<213> ORGANISM: Homo sapiens

<400> SEQUENCE: 154

Cys Ala Ser Ser Arg Gly Arg Gly Asp Gly Arg Thr Ile Tyr Phe
1 5 10 15

<210> SEQ ID NO 155
<211> LENGTH: 15
<212> TYPE: PRT
<213> ORGANISM: Homo sapiens

<400> SEQUENCE: 155

Cys Ala Ser Ser Arg Lys Thr Val Leu Asn Thr Glu Ala Phe Phe
1 5 10 15

<210> SEQ ID NO 156
<211> LENGTH: 14
<212> TYPE: PRT
<213> ORGANISM: Homo sapiens

<400> SEQUENCE: 156

Cys Ala Ser Ser Arg Val Gly Gln Ser Tyr Glu Gln Tyr Phe
1 5 10

<210> SEQ ID NO 157
<211> LENGTH: 15
<212> TYPE: PRT
<213> ORGANISM: Homo sapiens

<400> SEQUENCE: 157

Cys Ala Ser Ser Ser Phe Arg Val His Leu Tyr Glu Gln Tyr Phe
1 5 10 15

<210> SEQ ID NO 158
<211> LENGTH: 18
<212> TYPE: PRT
<213> ORGANISM: Homo sapiens

<400> SEQUENCE: 158

Cys Ala Ser Ser Ser Leu Arg Gly Gly Leu Thr Asn Thr Gly Glu Leu
1 5 10 15

Phe Phe

<210> SEQ ID NO 159
<211> LENGTH: 17
<212> TYPE: PRT
<213> ORGANISM: Homo sapiens

<400> SEQUENCE: 159

Cys Ala Ser Ser Ser Asn His Pro Gln Ser Arg Ala Asn Val Leu Thr
1 5 10 15

Phe

<210> SEQ ID NO 160
<211> LENGTH: 17
<212> TYPE: PRT
<213> ORGANISM: Homo sapiens

<400> SEQUENCE: 160

Cys Ala Ser Ser Ser Gln Thr Ser Gly Ser Trp Thr Gly Glu Leu Phe
1 5 10 15

Phe

<210> SEQ ID NO 161
<211> LENGTH: 15
<212> TYPE: PRT
<213> ORGANISM: Homo sapiens

<400> SEQUENCE: 161

Cys Ala Ser Ser Ser Ser Ile Ser Gly Pro Arg Ser Ile Tyr Phe
1 5 10 15

<210> SEQ ID NO 162
<211> LENGTH: 15
<212> TYPE: PRT
<213> ORGANISM: Homo sapiens

<400> SEQUENCE: 162

Cys Ala Ser Ser Ser Ser Gln Ser Arg Ala Asn Val Leu Thr Phe
1 5 10 15

<210> SEQ ID NO 163
<211> LENGTH: 14
<212> TYPE: PRT
<213> ORGANISM: Homo sapiens

<400> SEQUENCE: 163

Cys Ala Ser Ser Ser Thr Gly Gly Thr Asp Thr Gln Tyr Phe
1 5 10

<210> SEQ ID NO 164
<211> LENGTH: 14
<212> TYPE: PRT
<213> ORGANISM: Homo sapiens

<400> SEQUENCE: 164

Cys Ala Ser Ser Ser Thr Gly Val Gly Glu Thr Gln Tyr Phe
1 5 10

<210> SEQ ID NO 165
<211> LENGTH: 14
<212> TYPE: PRT
<213> ORGANISM: Homo sapiens

<400> SEQUENCE: 165

Cys Ala Ser Ser Ser Thr Leu Ala Gly Tyr Glu Gln Tyr Val
1 5 10

<210> SEQ ID NO 166
<211> LENGTH: 16
<212> TYPE: PRT
<213> ORGANISM: Homo sapiens

<400> SEQUENCE: 166

Cys Ala Ser Ser Ser Thr Ser Gly Leu Ala Lys Asn Ile Gln Tyr Phe
1 5 10 15

<210> SEQ ID NO 167
<211> LENGTH: 15
<212> TYPE: PRT
<213> ORGANISM: Homo sapiens

<400> SEQUENCE: 167

Cys Ala Ser Ser Ser Val Arg Gly Ile Gln Pro Pro Leu His Phe
1 5 10 15

<210> SEQ ID NO 168
<211> LENGTH: 15
<212> TYPE: PRT
<213> ORGANISM: Homo sapiens

<400> SEQUENCE: 168

Cys Ala Ser Ser Ser Val Arg Gly Thr Gln Pro Pro Leu His Phe
1 5 10 15

<210> SEQ ID NO 169
<211> LENGTH: 15
<212> TYPE: PRT
<213> ORGANISM: Homo sapiens

<400> SEQUENCE: 169

Cys Ala Ser Ser Thr Leu Asp Arg Gly Val Ala Gly Tyr Thr Phe
1 5 10 15

<210> SEQ ID NO 170
<211> LENGTH: 13
<212> TYPE: PRT
<213> ORGANISM: Homo sapiens

<400> SEQUENCE: 170

Cys Ala Ser Ser Val Ala Gly Ala Gly Glu Leu Phe Phe
1 5 10

<210> SEQ ID NO 171
<211> LENGTH: 13
<212> TYPE: PRT
<213> ORGANISM: Homo sapiens

<400> SEQUENCE: 171

Cys Ala Ser Ser Val Gly Gly Asp Gln Pro Gln His Phe
1 5 10

<210> SEQ ID NO 172
<211> LENGTH: 16
<212> TYPE: PRT
<213> ORGANISM: Homo sapiens

<400> SEQUENCE: 172

Cys Ala Ser Ser Val Gly Val Gly Val Ser Gly Asn Thr Ile Tyr Phe
1 5 10 15

<210> SEQ ID NO 173
<211> LENGTH: 14
<212> TYPE: PRT
<213> ORGANISM: Homo sapiens

<400> SEQUENCE: 173

Cys Ala Ser Ser Trp Ala Gly Gly Ile Asn Glu Gln Phe Phe
1 5 10

<210> SEQ ID NO 174
<211> LENGTH: 12
<212> TYPE: PRT
<213> ORGANISM: Homo sapiens

<400> SEQUENCE: 174

Cys Ala Ser Ser Trp Asp Gly Asn Glu Ala Phe Phe
1 5 10

<210> SEQ ID NO 175

<211> LENGTH: 16
<212> TYPE: PRT
<213> ORGANISM: Homo sapiens

<400> SEQUENCE: 175

Cys Ala Ser Ser Tyr Asp Arg Thr Gly Ala Asp Thr Glu Ala Phe Phe
1 5 10 15

<210> SEQ ID NO 176
<211> LENGTH: 15
<212> TYPE: PRT
<213> ORGANISM: Homo sapiens

<400> SEQUENCE: 176

Cys Ala Ser Ser Tyr Met Gly Ser Gly Ala Asn Val Leu Thr Phe
1 5 10 15

<210> SEQ ID NO 177
<211> LENGTH: 15
<212> TYPE: PRT
<213> ORGANISM: Homo sapiens

<400> SEQUENCE: 177

Cys Ala Ser Ser Tyr Ser Gly Arg Ile Ser Arg Gly Tyr Thr Ser
1 5 10 15

<210> SEQ ID NO 178
<211> LENGTH: 19
<212> TYPE: PRT
<213> ORGANISM: Homo sapiens

<400> SEQUENCE: 178

Cys Ala Ser Ser Tyr Ser Arg Pro Gly Ser Gly Arg Ala Lys Asp Thr
1 5 10 15

Gln Tyr Phe

<210> SEQ ID NO 179
<211> LENGTH: 18
<212> TYPE: PRT
<213> ORGANISM: Homo sapiens

<400> SEQUENCE: 179

Cys Ala Ser Ser Tyr Thr Arg Met Pro Pro Thr Phe Asn Glu Lys Leu
1 5 10 15

Phe Phe

<210> SEQ ID NO 180
<211> LENGTH: 15
<212> TYPE: PRT
<213> ORGANISM: Homo sapiens

<400> SEQUENCE: 180

Cys Ala Ser Thr Gly Gly Asn Arg Gly Val Asn Glu Gln Phe Phe
1 5 10 15

<210> SEQ ID NO 181
<211> LENGTH: 15
<212> TYPE: PRT
<213> ORGANISM: Homo sapiens

<400> SEQUENCE: 181

Cys Ala Ser Thr Gly Gly Asn Arg Gly Val Asn Glu Arg Phe Phe
1 5 10 15

<210> SEQ ID NO 182
<211> LENGTH: 17
<212> TYPE: PRT
<213> ORGANISM: Homo sapiens

<400> SEQUENCE: 182

Cys Ala Ser Thr Leu Ser Gln Leu Gly Pro Leu Tyr Tyr Glu Gln Tyr
1 5 10 15

Phe

<210> SEQ ID NO 183
<211> LENGTH: 16
<212> TYPE: PRT
<213> ORGANISM: Homo sapiens

<400> SEQUENCE: 183

Cys Ala Ser Thr Pro Asp Arg Ala Val Trp Asn Thr Glu Ala Phe Phe
1 5 10 15

<210> SEQ ID NO 184
<211> LENGTH: 15
<212> TYPE: PRT
<213> ORGANISM: Homo sapiens

<400> SEQUENCE: 184

Cys Ala Ser Thr Pro Gly Met Gly Gly Tyr Tyr Glu Gln Tyr Phe
1 5 10 15

<210> SEQ ID NO 185
<211> LENGTH: 14
<212> TYPE: PRT
<213> ORGANISM: Homo sapiens

<400> SEQUENCE: 185

Cys Ala Ser Thr Ser Gly Thr Ala Asn Asn Glu Gln Phe Phe
1 5 10

<210> SEQ ID NO 186
<211> LENGTH: 14
<212> TYPE: PRT
<213> ORGANISM: Homo sapiens

<400> SEQUENCE: 186

Cys Ala Ser Thr Tyr Gly Ser Gly Asp Tyr Glu Gln Tyr Phe
1 5 10

<210> SEQ ID NO 187
<211> LENGTH: 14
<212> TYPE: PRT
<213> ORGANISM: Homo sapiens

<400> SEQUENCE: 187

Cys Ala Thr Ser Ala Pro Gly Gly Tyr Asn Glu Gln Phe Phe
1 5 10

<210> SEQ ID NO 188
<211> LENGTH: 14
<212> TYPE: PRT
<213> ORGANISM: Homo sapiens

<400> SEQUENCE: 188

Cys Ala Thr Ser Asp Ser Leu Ala Lys Asn Ile Gln Tyr Phe
1 5 10

<210> SEQ ID NO 189
<211> LENGTH: 19
<212> TYPE: PRT
<213> ORGANISM: Homo sapiens

<400> SEQUENCE: 189

Cys Ala Thr Ser Asp Ser Gln Val Leu Ala Gly Leu Asn Gln Glu Thr
1 5 10 15

Gln Tyr Phe

<210> SEQ ID NO 190
<211> LENGTH: 12
<212> TYPE: PRT
<213> ORGANISM: Homo sapiens

<400> SEQUENCE: 190

Cys Ala Thr Ser Gly Tyr Arg Glu Leu Ala Phe Phe
1 5 10

<210> SEQ ID NO 191
<211> LENGTH: 13
<212> TYPE: PRT
<213> ORGANISM: Homo sapiens

<400> SEQUENCE: 191

Cys Ala Thr Ser Arg Asp Pro Leu Gln Glu Gln Phe Phe
1 5 10

<210> SEQ ID NO 192
<211> LENGTH: 13
<212> TYPE: PRT
<213> ORGANISM: Homo sapiens

<400> SEQUENCE: 192

Cys Ala Thr Ser Arg Asp Ser Asn Asn Glu Gln Phe Phe
1 5 10

<210> SEQ ID NO 193
<211> LENGTH: 11
<212> TYPE: PRT
<213> ORGANISM: Homo sapiens

<400> SEQUENCE: 193

Cys Ala Thr Ser Arg Asp Tyr Glu Gln Tyr Phe
1 5 10

<210> SEQ ID NO 194
<211> LENGTH: 15
<212> TYPE: PRT
<213> ORGANISM: Homo sapiens

<400> SEQUENCE: 194

Cys Ala Thr Ser Arg Gly Leu Ala Gly Gly Phe Glu Gln Phe Phe
1 5 10 15

<210> SEQ ID NO 195
<211> LENGTH: 15
<212> TYPE: PRT
<213> ORGANISM: Homo sapiens

<400> SEQUENCE: 195

Cys Ala Thr Ser Ser Leu Leu Ala Ser Pro Asn Glu Gln Phe Phe
1 5 10 15

<210> SEQ ID NO 196
<211> LENGTH: 12
<212> TYPE: PRT
<213> ORGANISM: Homo sapiens

<400> SEQUENCE: 196

Cys Ala Trp Gly Asp Met Ile Arg Ser Gln Tyr Phe
1 5 10

<210> SEQ ID NO 197
<211> LENGTH: 12
<212> TYPE: PRT
<213> ORGANISM: Homo sapiens

<400> SEQUENCE: 197

Cys Ala Trp Ser Glu Asp Arg Asp Glu Gln Tyr Phe
1 5 10

<210> SEQ ID NO 198
<211> LENGTH: 13
<212> TYPE: PRT
<213> ORGANISM: Homo sapiens

<400> SEQUENCE: 198

Cys Ala Trp Ser Glu Arg Asp Gly Gly Glu Gln Phe Phe
1 5 10

<210> SEQ ID NO 199
<211> LENGTH: 14
<212> TYPE: PRT
<213> ORGANISM: Homo sapiens

<400> SEQUENCE: 199

Cys Ala Trp Ser Gly Asp Ala Gly Gly Tyr Thr Leu His Phe
1 5 10

<210> SEQ ID NO 200
<211> LENGTH: 12
<212> TYPE: PRT
<213> ORGANISM: Homo sapiens

<400> SEQUENCE: 200

Cys Ala Trp Ser Pro Gly Thr Gly Ser Gln Tyr Phe
1 5 10

<210> SEQ ID NO 201
<211> LENGTH: 11
<212> TYPE: PRT
<213> ORGANISM: Homo sapiens

<400> SEQUENCE: 201

Cys Ala Trp Thr Arg Thr Asp Thr Gln Tyr Phe
1 5 10

<210> SEQ ID NO 202
<211> LENGTH: 13
<212> TYPE: PRT
<213> ORGANISM: Homo sapiens

<400> SEQUENCE: 202

Cys Ser Ala Ala Pro Ser Gly Tyr Ser Pro Leu His Phe
1 5 10

<210> SEQ ID NO 203

<211> LENGTH: 15
<212> TYPE: PRT
<213> ORGANISM: Homo sapiens

<400> SEQUENCE: 203

Cys Ser Ala Gly Gly Gln Gly Ser Tyr Ser Tyr Gly Tyr Thr Phe
1 5 10 15

<210> SEQ ID NO 204
<211> LENGTH: 15
<212> TYPE: PRT
<213> ORGANISM: Homo sapiens

<400> SEQUENCE: 204

Cys Ser Ala His Leu Ile Gly Gly Arg Tyr Asn Glu Gln Phe Phe
1 5 10 15

<210> SEQ ID NO 205
<211> LENGTH: 15
<212> TYPE: PRT
<213> ORGANISM: Homo sapiens

<400> SEQUENCE: 205

Cys Ser Ala Arg Asp Asn Arg Ala Glu Ile Ser Pro Leu His Phe
1 5 10 15

<210> SEQ ID NO 206
<211> LENGTH: 12
<212> TYPE: PRT
<213> ORGANISM: Homo sapiens

<400> SEQUENCE: 206

Cys Ser Ala Arg Asp Gln Asp Glu Lys Leu Phe Phe
1 5 10

<210> SEQ ID NO 207
<211> LENGTH: 16
<212> TYPE: PRT
<213> ORGANISM: Homo sapiens

<400> SEQUENCE: 207

Cys Ser Ala Arg Asp Gln Gly Gln His Ala Pro Tyr Glu Gln Tyr Phe
1 5 10 15

<210> SEQ ID NO 208
<211> LENGTH: 13
<212> TYPE: PRT
<213> ORGANISM: Homo sapiens

<400> SEQUENCE: 208

Cys Ser Ala Arg Gly Leu Ala Gly Gly Gly Gln Phe Phe
1 5 10

<210> SEQ ID NO 209
<211> LENGTH: 14
<212> TYPE: PRT
<213> ORGANISM: Homo sapiens

<400> SEQUENCE: 209

Cys Ser Ala Arg Asn Arg Val Asn Thr Gly Glu Leu Phe Phe
1 5 10

<210> SEQ ID NO 210
<211> LENGTH: 12
<212> TYPE: PRT

<213> ORGANISM: Homo sapiens

<400> SEQUENCE: 210

Cys Ser Ala Arg Gln Leu Pro Tyr Gly Tyr Thr Phe
1 5 10

<210> SEQ ID NO 211
<211> LENGTH: 13
<212> TYPE: PRT
<213> ORGANISM: Homo sapiens

<400> SEQUENCE: 211

Cys Ser Ala Arg Val Gly Val Asn Gln Pro Gln His Phe
1 5 10

<210> SEQ ID NO 212
<211> LENGTH: 17
<212> TYPE: PRT
<213> ORGANISM: Homo sapiens

<400> SEQUENCE: 212

Cys Ser Ala Arg Val Met Thr Ser Gly Ser Met Arg Glu Thr Gln Tyr
1 5 10 15

Phe

<210> SEQ ID NO 213
<211> LENGTH: 17
<212> TYPE: PRT
<213> ORGANISM: Homo sapiens

<400> SEQUENCE: 213

Cys Ser Ala Arg Val Met Thr Ser Arg Ser Met Arg Glu Ala Gln Tyr
1 5 10 15

Phe

<210> SEQ ID NO 214
<211> LENGTH: 14
<212> TYPE: PRT
<213> ORGANISM: Homo sapiens

<400> SEQUENCE: 214

Cys Ser Ala Ser Glu Ala Ala Gly Ala Asn Val Leu Thr Phe
1 5 10

<210> SEQ ID NO 215
<211> LENGTH: 14
<212> TYPE: PRT
<213> ORGANISM: Homo sapiens

<400> SEQUENCE: 215

Cys Ser Ala Ser Pro Gly Thr Ser Thr Gln Thr Gln Tyr Phe
1 5 10

<210> SEQ ID NO 216
<211> LENGTH: 14
<212> TYPE: PRT
<213> ORGANISM: Homo sapiens

<400> SEQUENCE: 216

Cys Ser Ala Ser Val Thr Gly Thr Ala Tyr Glu Gln Tyr Phe
1 5 10

<210> SEQ ID NO 217

<211> LENGTH: 13
<212> TYPE: PRT
<213> ORGANISM: Homo sapiens

<400> SEQUENCE: 217

Cys Ser Val Ala Val Thr Gly Thr Gly Glu Gln Tyr Phe
1 5 10

<210> SEQ ID NO 218
<211> LENGTH: 11
<212> TYPE: PRT
<213> ORGANISM: Homo sapiens

<400> SEQUENCE: 218

Cys Ser Val Glu Arg Gly Thr Glu Ala Phe Phe
1 5 10

<210> SEQ ID NO 219
<211> LENGTH: 13
<212> TYPE: PRT
<213> ORGANISM: Homo sapiens

<400> SEQUENCE: 219

Cys Ser Val Gly Pro Gly Leu Ala Ser Pro Leu His Phe
1 5 10

<210> SEQ ID NO 220
<211> LENGTH: 13
<212> TYPE: PRT
<213> ORGANISM: Homo sapiens

<400> SEQUENCE: 220

Cys Ser Val Ser Gly Arg Ser Tyr Asn Glu Gln Phe Phe
1 5 10

<210> SEQ ID NO 221
<211> LENGTH: 14
<212> TYPE: PRT
<213> ORGANISM: Homo sapiens

<400> SEQUENCE: 221

Cys Ser Val Thr Gly Thr Asp Tyr Ser Tyr Glu Gln Tyr Phe
1 5 10

<210> SEQ ID NO 222
<211> LENGTH: 11
<212> TYPE: PRT
<213> ORGANISM: Homo sapiens

<400> SEQUENCE: 222

Cys Ser Val Val Gln Gly Ala Gly Tyr Thr Phe
1 5 10

<210> SEQ ID NO 223
<211> LENGTH: 14
<212> TYPE: PRT
<213> ORGANISM: Homo sapiens

<400> SEQUENCE: 223

Arg Ala Ser Ser Gly Ala Asp Ser Asn Ser Pro Leu His Phe
1 5 10

<210> SEQ ID NO 224
<211> LENGTH: 8
<212> TYPE: PRT

<213> ORGANISM: Homo sapiens

<400> SEQUENCE: 224

His Val Ile Glu Asn Ile Tyr Phe
1               5

<210> SEQ ID NO 225
<211> LENGTH: 9
<212> TYPE: PRT
<213> ORGANISM: Homo sapiens

<400> SEQUENCE: 225

Asp Val Ala Ala His Leu Gln Pro Leu
1               5

<210> SEQ ID NO 226
<211> LENGTH: 8
<212> TYPE: PRT
<213> ORGANISM: Homo sapiens

<400> SEQUENCE: 226

Glu Thr Pro Asn Leu Asp Leu Met
1               5

<210> SEQ ID NO 227
<211> LENGTH: 9
<212> TYPE: PRT
<213> ORGANISM: Homo sapiens

<400> SEQUENCE: 227

Ser Val Phe Asn Thr Trp Asn Pro Met
1               5

<210> SEQ ID NO 228
<211> LENGTH: 8
<212> TYPE: PRT
<213> ORGANISM: Homo sapiens

<400> SEQUENCE: 228

Glu Val Gln Gln Phe Leu Arg Tyr
1               5

<210> SEQ ID NO 229
<211> LENGTH: 9
<212> TYPE: PRT
<213> ORGANISM: Homo sapiens

<400> SEQUENCE: 229

Glu Val Ile Val Pro Leu Ser Gly Trp
1               5

<210> SEQ ID NO 230
<211> LENGTH: 9
<212> TYPE: PRT
<213> ORGANISM: Homo sapiens

<400> SEQUENCE: 230

Glu Thr Met Gln Cys Ser Glu Leu Tyr
1               5

<210> SEQ ID NO 231
<211> LENGTH: 11
<212> TYPE: PRT
<213> ORGANISM: Homo sapiens

<400> SEQUENCE: 231

Glu Thr Met Gln Cys Ser Glu Leu Tyr His Met
1               5                   10

<210> SEQ ID NO 232
<211> LENGTH: 8
<212> TYPE: PRT
<213> ORGANISM: Homo sapiens

<400> SEQUENCE: 232

Glu Thr Met Gln Cys Ser Glu Leu
1               5

<210> SEQ ID NO 233
<211> LENGTH: 10
<212> TYPE: PRT
<213> ORGANISM: Homo sapiens

<400> SEQUENCE: 233

Ile Thr Arg Thr Val Ser Ala Asn Thr Val
1               5                   10

<210> SEQ ID NO 234
<211> LENGTH: 10
<212> TYPE: PRT
<213> ORGANISM: Homo sapiens

<400> SEQUENCE: 234

Ala Thr Lys Asn Asn Lys Val Ile Met Ala
1               5                   10

<210> SEQ ID NO 235
<211> LENGTH: 10
<212> TYPE: PRT
<213> ORGANISM: Homo sapiens

<400> SEQUENCE: 235

Val Ala His Phe Gln Leu Gln Met Leu Lys
1               5                   10

<210> SEQ ID NO 236
<211> LENGTH: 9
<212> TYPE: PRT
<213> ORGANISM: Homo sapiens

<400> SEQUENCE: 236

Glu Glu Asp Thr Phe Ser Tyr Leu Ile
1               5

<210> SEQ ID NO 237
<211> LENGTH: 8
<212> TYPE: PRT
<213> ORGANISM: Homo sapiens

<400> SEQUENCE: 237

Ala His Phe Gln Leu Gln Met Leu
1               5

<210> SEQ ID NO 238
<211> LENGTH: 11
<212> TYPE: PRT
<213> ORGANISM: Homo sapiens

<400> SEQUENCE: 238

```
Leu His Ala Met Ile Gln Ala Ala Gly Lys Leu
1               5                   10


<210> SEQ ID NO 239
<211> LENGTH: 11
<212> TYPE: PRT
<213> ORGANISM: Homo sapiens

<400> SEQUENCE: 239

Leu His Glu Ala Gln Pro Trp Phe Glu Phe Leu
1               5                   10


<210> SEQ ID NO 240
<211> LENGTH: 10
<212> TYPE: PRT
<213> ORGANISM: Homo sapiens

<400> SEQUENCE: 240

Leu His Glu Ala Gln Pro Trp Phe Glu Phe
1               5                   10


<210> SEQ ID NO 241
<211> LENGTH: 10
<212> TYPE: PRT
<213> ORGANISM: Homo sapiens

<400> SEQUENCE: 241

Glu His Leu Ser Cys Pro Asp Asn Phe Leu
1               5                   10


<210> SEQ ID NO 242
<211> LENGTH: 10
<212> TYPE: PRT
<213> ORGANISM: Homo sapiens

<400> SEQUENCE: 242

Asn His Ala Arg Ile Asp Ala Ala Lys Val
1               5                   10


<210> SEQ ID NO 243
<211> LENGTH: 9
<212> TYPE: PRT
<213> ORGANISM: Homo sapiens

<400> SEQUENCE: 243

Gln His Gln Pro Asn Pro Phe Glu Val
1               5


<210> SEQ ID NO 244
<211> LENGTH: 8
<212> TYPE: PRT
<213> ORGANISM: Homo sapiens

<400> SEQUENCE: 244

Thr Gln Leu Glu Lys Glu Ala Leu
1               5


<210> SEQ ID NO 245
<211> LENGTH: 11
<212> TYPE: PRT
<213> ORGANISM: Homo sapiens

<400> SEQUENCE: 245

Thr Arg Ala Arg Asn Glu Tyr Leu Leu Ser Leu
1               5                   10
```

<210> SEQ ID NO 246
<211> LENGTH: 8
<212> TYPE: PRT
<213> ORGANISM: Homo sapiens

<400> SEQUENCE: 246

Asn Pro Met Trp Val Val Leu Leu
1               5

<210> SEQ ID NO 247
<211> LENGTH: 8
<212> TYPE: PRT
<213> ORGANISM: Homo sapiens

<400> SEQUENCE: 247

Lys His Ile Leu Val Trp Ala Leu
1               5

<210> SEQ ID NO 248
<211> LENGTH: 8
<212> TYPE: PRT
<213> ORGANISM: Homo sapiens

<400> SEQUENCE: 248

Ser Gln Ser Asp Tyr Ile Pro Met
1               5

<210> SEQ ID NO 249
<211> LENGTH: 8
<212> TYPE: PRT
<213> ORGANISM: Homo sapiens

<400> SEQUENCE: 249

Val His Asp Tyr Phe Ser Val Ile
1               5

<210> SEQ ID NO 250
<211> LENGTH: 9
<212> TYPE: PRT
<213> ORGANISM: Homo sapiens

<400> SEQUENCE: 250

Ile Tyr Phe Pro Ala Ala Gln Thr Met
1               5

<210> SEQ ID NO 251
<211> LENGTH: 11
<212> TYPE: PRT
<213> ORGANISM: Homo sapiens

<400> SEQUENCE: 251

Phe Ser Tyr Leu Ile Trp Ser Asn Pro Arg Tyr
1               5                   10

<210> SEQ ID NO 252
<211> LENGTH: 10
<212> TYPE: PRT
<213> ORGANISM: Homo sapiens

<400> SEQUENCE: 252

Tyr Ser Trp Ser Ala Gln Arg Gln Ala Leu
1               5                   10

<210> SEQ ID NO 253
<211> LENGTH: 10
<212> TYPE: PRT
<213> ORGANISM: Homo sapiens

<400> SEQUENCE: 253

Phe Ala Val Trp Thr Leu Ala Glu Thr Ile
1 5 10

<210> SEQ ID NO 254
<211> LENGTH: 11
<212> TYPE: PRT
<213> ORGANISM: Homo sapiens

<400> SEQUENCE: 254

Phe Ala Ser Leu Ala Leu Ala Arg Arg Tyr Leu
1 5 10

<210> SEQ ID NO 255
<211> LENGTH: 11
<212> TYPE: PRT
<213> ORGANISM: Homo sapiens

<400> SEQUENCE: 255

Asp Val Ile Gln Gln Asp Glu Leu Asp Ser Tyr
1 5 10

<210> SEQ ID NO 256
<211> LENGTH: 10
<212> TYPE: PRT
<213> ORGANISM: Homo sapiens

<400> SEQUENCE: 256

Lys Asn Arg Ser Ser Gly Thr Val Ser Ala
1 5 10

<210> SEQ ID NO 257
<211> LENGTH: 9
<212> TYPE: PRT
<213> ORGANISM: Homo sapiens

<400> SEQUENCE: 257

Lys Leu Lys Arg Phe Asn Leu Ser Ala
1 5

<210> SEQ ID NO 258
<211> LENGTH: 9
<212> TYPE: PRT
<213> ORGANISM: Homo sapiens

<400> SEQUENCE: 258

Lys Ser Phe Ala Val Trp Thr Leu Ala
1 5

<210> SEQ ID NO 259
<211> LENGTH: 9
<212> TYPE: PRT
<213> ORGANISM: Homo sapiens

<400> SEQUENCE: 259

Lys Trp Arg Leu Ser Leu Cys Thr Val
1 5

<210> SEQ ID NO 260
<211> LENGTH: 10

<212> TYPE: PRT
<213> ORGANISM: Homo sapiens

<400> SEQUENCE: 260

Arg Ser Arg Pro Val Ala Ala Thr Ala Lys
1 5 10

<210> SEQ ID NO 261
<211> LENGTH: 9
<212> TYPE: PRT
<213> ORGANISM: Homo sapiens

<400> SEQUENCE: 261

Arg Ser Arg Pro Val Ala Ala Thr Ala
1 5

<210> SEQ ID NO 262
<211> LENGTH: 11
<212> TYPE: PRT
<213> ORGANISM: Homo sapiens

<400> SEQUENCE: 262

Thr Ala Lys Gln Ala His Leu Thr Thr Leu Lys
1 5 10

<210> SEQ ID NO 263
<211> LENGTH: 9
<212> TYPE: PRT
<213> ORGANISM: Homo sapiens

<400> SEQUENCE: 263

Ser His Cys Pro Ser Ala Met Gly Ile
1 5

<210> SEQ ID NO 264
<211> LENGTH: 8
<212> TYPE: PRT
<213> ORGANISM: Homo sapiens

<400> SEQUENCE: 264

Phe His Ala Ser Glu Gly Trp Leu
1 5

<210> SEQ ID NO 265
<211> LENGTH: 8
<212> TYPE: PRT
<213> ORGANISM: Homo sapiens

<400> SEQUENCE: 265

Thr His Glu Val Ile Val Pro Leu
1 5

<210> SEQ ID NO 266
<211> LENGTH: 8
<212> TYPE: PRT
<213> ORGANISM: Homo sapiens

<400> SEQUENCE: 266

Ser Arg His Cys Leu Gln Pro Leu
1 5

<210> SEQ ID NO 267
<211> LENGTH: 10
<212> TYPE: PRT
<213> ORGANISM: Homo sapiens

<400> SEQUENCE: 267

Phe Ala Ser Leu Ala Leu Ala Arg Arg Tyr
1 5 10

<210> SEQ ID NO 268
<211> LENGTH: 11
<212> TYPE: PRT
<213> ORGANISM: Homo sapiens

<400> SEQUENCE: 268

Ser Val Phe Asn Thr Trp Asn Pro Met Trp Val
1 5 10

<210> SEQ ID NO 269
<211> LENGTH: 9
<212> TYPE: PRT
<213> ORGANISM: Homo sapiens

<400> SEQUENCE: 269

Leu Thr His Glu Val Ile Val Pro Leu
1 5

<210> SEQ ID NO 270
<211> LENGTH: 10
<212> TYPE: PRT
<213> ORGANISM: Homo sapiens

<400> SEQUENCE: 270

Tyr Thr Val Met Ala Arg Lys Ser Pro Val
1 5 10

<210> SEQ ID NO 271
<211> LENGTH: 8
<212> TYPE: PRT
<213> ORGANISM: Homo sapiens

<400> SEQUENCE: 271

His Val Ile Glu Asn Ile Tyr Leu
1 5

<210> SEQ ID NO 272
<211> LENGTH: 9
<212> TYPE: PRT
<213> ORGANISM: Homo sapiens

<400> SEQUENCE: 272

Asp Val Ala Ala His Leu Gln Leu Leu
1 5

<210> SEQ ID NO 273
<211> LENGTH: 8
<212> TYPE: PRT
<213> ORGANISM: Homo sapiens

<400> SEQUENCE: 273

Glu Thr Pro Asn Leu Asp Arg Met
1 5

<210> SEQ ID NO 274
<211> LENGTH: 9
<212> TYPE: PRT
<213> ORGANISM: Homo sapiens

<400> SEQUENCE: 274

Ser Val Phe Asn Thr Trp Lys Pro Met
1 5

<210> SEQ ID NO 275
<211> LENGTH: 8
<212> TYPE: PRT
<213> ORGANISM: Homo sapiens

<400> SEQUENCE: 275

Glu Ala Gln Gln Phe Leu Arg Tyr
1 5

<210> SEQ ID NO 276
<211> LENGTH: 9
<212> TYPE: PRT
<213> ORGANISM: Homo sapiens

<400> SEQUENCE: 276

Glu Val Ile Val Pro His Ser Gly Trp
1 5

<210> SEQ ID NO 277
<211> LENGTH: 9
<212> TYPE: PRT
<213> ORGANISM: Homo sapiens

<400> SEQUENCE: 277

Glu Ala Met Gln Cys Ser Glu Leu Tyr
1 5

<210> SEQ ID NO 278
<211> LENGTH: 11
<212> TYPE: PRT
<213> ORGANISM: Homo sapiens

<400> SEQUENCE: 278

Glu Ala Met Gln Cys Ser Glu Leu Tyr His Met
1 5 10

<210> SEQ ID NO 279
<211> LENGTH: 8
<212> TYPE: PRT
<213> ORGANISM: Homo sapiens

<400> SEQUENCE: 279

Glu Ala Met Gln Cys Ser Glu Leu
1 5

<210> SEQ ID NO 280
<211> LENGTH: 10
<212> TYPE: PRT
<213> ORGANISM: Homo sapiens

<400> SEQUENCE: 280

Ile Thr Arg Thr Val Ser Gly Asn Thr Val
1 5 10

<210> SEQ ID NO 281
<211> LENGTH: 10
<212> TYPE: PRT
<213> ORGANISM: Homo sapiens

<400> SEQUENCE: 281

Ala Thr Lys Asn Ile Lys Val Ile Met Ala 1 5 10

<210> SEQ ID NO 282
<211> LENGTH: 10
<212> TYPE: PRT
<213> ORGANISM: Homo sapiens

<400> SEQUENCE: 282

Val Ala His Phe Gln Arg Gln Met Leu Lys
1 5 10

<210> SEQ ID NO 283
<211> LENGTH: 9
<212> TYPE: PRT
<213> ORGANISM: Homo sapiens

<400> SEQUENCE: 283

Glu Glu Asp Thr Phe Ser Asp Leu Ile
1 5

<210> SEQ ID NO 284
<211> LENGTH: 8
<212> TYPE: PRT
<213> ORGANISM: Homo sapiens

<400> SEQUENCE: 284

Ala His Phe Gln Arg Gln Met Leu
1 5

<210> SEQ ID NO 285
<211> LENGTH: 11
<212> TYPE: PRT
<213> ORGANISM: Homo sapiens

<400> SEQUENCE: 285

Leu Gln Ala Met Ile Gln Ala Ala Gly Lys Leu
1 5 10

<210> SEQ ID NO 286
<211> LENGTH: 11
<212> TYPE: PRT
<213> ORGANISM: Homo sapiens

<400> SEQUENCE: 286

Leu His Glu Ala His Pro Trp Phe Glu Phe Leu
1 5 10

<210> SEQ ID NO 287
<211> LENGTH: 10
<212> TYPE: PRT
<213> ORGANISM: Homo sapiens

<400> SEQUENCE: 287

Leu His Glu Ala His Pro Trp Phe Glu Phe
1 5 10

<210> SEQ ID NO 288
<211> LENGTH: 10
<212> TYPE: PRT
<213> ORGANISM: Homo sapiens

<400> SEQUENCE: 288

Glu His Leu Ser Tyr Pro Asp Asn Phe Leu
1 5 10

<210> SEQ ID NO 289
<211> LENGTH: 10
<212> TYPE: PRT
<213> ORGANISM: Homo sapiens

<400> SEQUENCE: 289

Asn His Ala Arg Ile Asp Ala Ala Glu Gly
1 5 10

<210> SEQ ID NO 290
<211> LENGTH: 9
<212> TYPE: PRT
<213> ORGANISM: Homo sapiens

<400> SEQUENCE: 290

Leu His Gln Pro Asn Pro Phe Glu Val
1 5

<210> SEQ ID NO 291
<211> LENGTH: 8
<212> TYPE: PRT
<213> ORGANISM: Homo sapiens

<400> SEQUENCE: 291

Thr Gln Gln Glu Lys Glu Ala Leu
1 5

<210> SEQ ID NO 292
<211> LENGTH: 11
<212> TYPE: PRT
<213> ORGANISM: Homo sapiens

<400> SEQUENCE: 292

Thr Lys Ala Arg Asn Glu Tyr Leu Leu Ser Leu
1 5 10

<210> SEQ ID NO 293
<211> LENGTH: 8
<212> TYPE: PRT
<213> ORGANISM: Homo sapiens

<400> SEQUENCE: 293

Lys Pro Met Trp Val Val Leu Leu
1 5

<210> SEQ ID NO 294
<211> LENGTH: 8
<212> TYPE: PRT
<213> ORGANISM: Homo sapiens

<400> SEQUENCE: 294

Lys His Ile Leu Val Trp Ala Pro
1 5

<210> SEQ ID NO 295
<211> LENGTH: 8
<212> TYPE: PRT
<213> ORGANISM: Homo sapiens

<400> SEQUENCE: 295

Ser Gln Ser Val Tyr Ile Pro Met
1 5

<210> SEQ ID NO 296

<211> LENGTH: 8
<212> TYPE: PRT
<213> ORGANISM: Homo sapiens

<400> SEQUENCE: 296

Val His Asp Asp Phe Ser Val Ile
1               5

<210> SEQ ID NO 297
<211> LENGTH: 9
<212> TYPE: PRT
<213> ORGANISM: Homo sapiens

<400> SEQUENCE: 297

Ile Tyr Leu Pro Ala Ala Gln Thr Met
1               5

<210> SEQ ID NO 298
<211> LENGTH: 11
<212> TYPE: PRT
<213> ORGANISM: Homo sapiens

<400> SEQUENCE: 298

Phe Ser Asp Leu Ile Trp Ser Asn Pro Arg Tyr
1               5                   10

<210> SEQ ID NO 299
<211> LENGTH: 10
<212> TYPE: PRT
<213> ORGANISM: Homo sapiens

<400> SEQUENCE: 299

Tyr Ser Trp Ser Ala Gln Arg Arg Ala Leu
1               5                   10

<210> SEQ ID NO 300
<211> LENGTH: 10
<212> TYPE: PRT
<213> ORGANISM: Homo sapiens

<400> SEQUENCE: 300

Phe Ala Val Gly Thr Leu Ala Glu Thr Ile
1               5                   10

<210> SEQ ID NO 301
<211> LENGTH: 11
<212> TYPE: PRT
<213> ORGANISM: Homo sapiens

<400> SEQUENCE: 301

Phe Ala Ser Leu Ala Leu Val Arg Arg Tyr Leu
1               5                   10

<210> SEQ ID NO 302
<211> LENGTH: 11
<212> TYPE: PRT
<213> ORGANISM: Homo sapiens

<400> SEQUENCE: 302

Asp Val Leu Gln Gln Asp Glu Leu Asp Ser Tyr
1               5                   10

<210> SEQ ID NO 303
<211> LENGTH: 10
<212> TYPE: PRT

<213> ORGANISM: Homo sapiens

<400> SEQUENCE: 303

Lys Asn His Ser Ser Gly Thr Val Ser Ala
1 5 10

<210> SEQ ID NO 304
<211> LENGTH: 9
<212> TYPE: PRT
<213> ORGANISM: Homo sapiens

<400> SEQUENCE: 304

Lys Leu Lys Ser Phe Asn Leu Ser Ala
1 5

<210> SEQ ID NO 305
<211> LENGTH: 9
<212> TYPE: PRT
<213> ORGANISM: Homo sapiens

<400> SEQUENCE: 305

Lys Ser Phe Ala Val Gly Thr Leu Ala
1 5

<210> SEQ ID NO 306
<211> LENGTH: 9
<212> TYPE: PRT
<213> ORGANISM: Homo sapiens

<400> SEQUENCE: 306

Lys Trp Arg Leu Ser His Cys Thr Val
1 5

<210> SEQ ID NO 307
<211> LENGTH: 10
<212> TYPE: PRT
<213> ORGANISM: Homo sapiens

<400> SEQUENCE: 307

Arg Ser Arg Pro Val Ala Ala Lys Ala Lys
1 5 10

<210> SEQ ID NO 308
<211> LENGTH: 9
<212> TYPE: PRT
<213> ORGANISM: Homo sapiens

<400> SEQUENCE: 308

Arg Ser Arg Pro Val Ala Ala Lys Ala
1 5

<210> SEQ ID NO 309
<211> LENGTH: 11
<212> TYPE: PRT
<213> ORGANISM: Homo sapiens

<400> SEQUENCE: 309

Lys Ala Lys Gln Ala His Leu Thr Thr Leu Lys
1 5 10

<210> SEQ ID NO 310
<211> LENGTH: 9
<212> TYPE: PRT
<213> ORGANISM: Homo sapiens

<400> SEQUENCE: 310

Ser Arg Cys Pro Ser Ala Met Gly Ile
1 5

<210> SEQ ID NO 311
<211> LENGTH: 8
<212> TYPE: PRT
<213> ORGANISM: Homo sapiens

<400> SEQUENCE: 311

Phe His Ala Ser Gln Gly Trp Leu
1 5

<210> SEQ ID NO 312
<211> LENGTH: 8
<212> TYPE: PRT
<213> ORGANISM: Homo sapiens

<400> SEQUENCE: 312

Thr His Glu Val Ile Val Pro His
1 5

<210> SEQ ID NO 313
<211> LENGTH: 8
<212> TYPE: PRT
<213> ORGANISM: Homo sapiens

<400> SEQUENCE: 313

Gly Arg His Cys Leu Gln Pro Leu
1 5

<210> SEQ ID NO 314
<211> LENGTH: 10
<212> TYPE: PRT
<213> ORGANISM: Homo sapiens

<400> SEQUENCE: 314

Phe Ala Ser Leu Ala Leu Val Arg Arg Tyr
1 5 10

<210> SEQ ID NO 315
<211> LENGTH: 11
<212> TYPE: PRT
<213> ORGANISM: Homo sapiens

<400> SEQUENCE: 315

Ser Val Phe Asn Thr Trp Lys Pro Met Trp Val
1 5 10

<210> SEQ ID NO 316
<211> LENGTH: 9
<212> TYPE: PRT
<213> ORGANISM: Homo sapiens

<400> SEQUENCE: 316

Leu Thr His Glu Val Ile Val Pro His
1 5

<210> SEQ ID NO 317
<211> LENGTH: 10
<212> TYPE: PRT
<213> ORGANISM: Homo sapiens

<400> SEQUENCE: 317

Val Tyr Arg Tyr Gly Gln Lys Lys Pro Cys
1 5 10

<210> SEQ ID NO 318
<211> LENGTH: 15
<212> TYPE: PRT
<213> ORGANISM: Unknown
<220> FEATURE:
<223> OTHER INFORMATION: Description of Unknown:
JH124 sequence

<400> SEQUENCE: 318

Cys Ala Ser Ser Gly Gln Gly Gly Val Ser Glu Lys Leu Phe Phe
1 5 10 15

<210> SEQ ID NO 319
<211> LENGTH: 15
<212> TYPE: PRT
<213> ORGANISM: Unknown
<220> FEATURE:
<223> OTHER INFORMATION: Description of Unknown:
JH124 sequence

<400> SEQUENCE: 319

Cys Ala Ser Ser Leu Thr Gly Gly Tyr Thr Gly Glu Leu Phe Phe
1 5 10 15

<210> SEQ ID NO 320
<211> LENGTH: 14
<212> TYPE: PRT
<213> ORGANISM: Unknown
<220> FEATURE:
<223> OTHER INFORMATION: Description of Unknown:
JH124 sequence

<400> SEQUENCE: 320

Cys Ala Ser Ser Leu Arg Ser Ser Ser Glu Thr Gln Tyr Phe
1 5 10

<210> SEQ ID NO 321
<211> LENGTH: 16
<212> TYPE: PRT
<213> ORGANISM: Unknown
<220> FEATURE:
<223> OTHER INFORMATION: Description of Unknown:
JH124 sequence

<400> SEQUENCE: 321

Cys Ala Ser Ser Leu Gln Ala Gly Ser Ser Tyr Asn Glu Gln Phe Phe
1 5 10 15

<210> SEQ ID NO 322
<211> LENGTH: 16
<212> TYPE: PRT
<213> ORGANISM: Unknown
<220> FEATURE:
<223> OTHER INFORMATION: Description of Unknown:
JH124 sequence

<400> SEQUENCE: 322

Cys Ala Ser Ser Pro Ser Gly Gly Ser Leu Tyr Asn Glu Gln Phe Phe
1 5 10 15

<210> SEQ ID NO 323
<211> LENGTH: 14
<212> TYPE: PRT
<213> ORGANISM: Unknown
<220> FEATURE:

<223> OTHER INFORMATION: Description of Unknown:
JH124 sequence

<400> SEQUENCE: 323

Cys Ala Ser Ser Gly Gly Ile Ser Asn Thr Glu Ala Phe Phe
1 5 10

<210> SEQ ID NO 324
<211> LENGTH: 17
<212> TYPE: PRT
<213> ORGANISM: Unknown
<220> FEATURE:
<223> OTHER INFORMATION: Description of Unknown:
JH124 sequence

<400> SEQUENCE: 324

Cys Ala Thr Ser Thr Leu Pro Ser Gly Gly Glu Gly Tyr Glu Gln Tyr
1 5 10 15

Phe

<210> SEQ ID NO 325
<211> LENGTH: 12
<212> TYPE: PRT
<213> ORGANISM: Unknown
<220> FEATURE:
<223> OTHER INFORMATION: Description of Unknown:
JH124 sequence

<400> SEQUENCE: 325

Cys Ala Ser Ser Gly Thr Thr Tyr Gly Tyr Thr Phe
1 5 10

<210> SEQ ID NO 326
<211> LENGTH: 12
<212> TYPE: PRT
<213> ORGANISM: Unknown
<220> FEATURE:
<223> OTHER INFORMATION: Description of Unknown:
JH124 sequence

<400> SEQUENCE: 326

Cys Ser Ala Ser Arg Gly Leu Ser Gly Tyr Thr Phe
1 5 10

<210> SEQ ID NO 327
<211> LENGTH: 13
<212> TYPE: PRT
<213> ORGANISM: Unknown
<220> FEATURE:
<223> OTHER INFORMATION: Description of Unknown:
JH124 sequence

<400> SEQUENCE: 327

Leu Gly Pro Gly Thr Phe Thr Ser Tyr Glu Gln Tyr Phe
1 5 10

<210> SEQ ID NO 328
<211> LENGTH: 14
<212> TYPE: PRT
<213> ORGANISM: Unknown
<220> FEATURE:
<223> OTHER INFORMATION: Description of Unknown:
JH124 sequence

<400> SEQUENCE: 328

Cys Ala Ser Ser Thr Gly Thr Gly Phe Gly Glu Gln Tyr Phe
1 5 10

<210> SEQ ID NO 329
<211> LENGTH: 13
<212> TYPE: PRT
<213> ORGANISM: Unknown
<220> FEATURE:
<223> OTHER INFORMATION: Description of Unknown:
JH124 sequence

<400> SEQUENCE: 329

Cys Ala Ser Ser Glu Gly Gly Ser Asp Glu Gln Tyr Phe
1 5 10

<210> SEQ ID NO 330
<211> LENGTH: 17
<212> TYPE: PRT
<213> ORGANISM: Unknown
<220> FEATURE:
<223> OTHER INFORMATION: Description of Unknown:
JH124 sequence

<400> SEQUENCE: 330

Cys Ala Ser Ser Leu Asp Pro Arg Ser Ser Tyr Asn Ser Pro Leu His
1 5 10 15

Phe

<210> SEQ ID NO 331
<211> LENGTH: 16
<212> TYPE: PRT
<213> ORGANISM: Unknown
<220> FEATURE:
<223> OTHER INFORMATION: Description of Unknown:
JH124 sequence

<400> SEQUENCE: 331

Cys Ala Ser Thr Ala Gly Thr Val His Ser Asn Gln Pro Gln His Phe
1 5 10 15

<210> SEQ ID NO 332
<211> LENGTH: 15
<212> TYPE: PRT
<213> ORGANISM: Unknown
<220> FEATURE:
<223> OTHER INFORMATION: Description of Unknown:
JH124 sequence

<400> SEQUENCE: 332

Cys Ala Ser Arg Asp Thr Arg Glu Leu Asn Thr Glu Ala Phe Phe
1 5 10 15

<210> SEQ ID NO 333
<211> LENGTH: 16
<212> TYPE: PRT
<213> ORGANISM: Unknown
<220> FEATURE:
<223> OTHER INFORMATION: Description of Unknown:
JH124 sequence

<400> SEQUENCE: 333

Cys Ala Ser Ser Leu Gly Asp Leu Arg Gly Phe Thr Glu Ala Phe Phe
1 5 10 15

<210> SEQ ID NO 334
<211> LENGTH: 14
<212> TYPE: PRT
<213> ORGANISM: Unknown
<220> FEATURE:

<223> OTHER INFORMATION: Description of Unknown:
JH124 sequence

<400> SEQUENCE: 334

Cys Ala Thr Ser Asp Leu Val Ala Arg Asp Glu Gln Phe Phe
1 5 10

<210> SEQ ID NO 335
<211> LENGTH: 15
<212> TYPE: PRT
<213> ORGANISM: Unknown
<220> FEATURE:
<223> OTHER INFORMATION: Description of Unknown:
JH124 sequence

<400> SEQUENCE: 335

Cys Ala Ser Ser Tyr Arg Gly Thr Gly Gly Gly Gly Tyr Thr Phe
1 5 10 15

<210> SEQ ID NO 336
<211> LENGTH: 16
<212> TYPE: PRT
<213> ORGANISM: Unknown
<220> FEATURE:
<223> OTHER INFORMATION: Description of Unknown:
JH124 sequence

<400> SEQUENCE: 336

Cys Ala Ser Ser Leu Gln Gly Gly Met Gly Asn Gln Pro Gln His Phe
1 5 10 15

<210> SEQ ID NO 337
<211> LENGTH: 13
<212> TYPE: PRT
<213> ORGANISM: Unknown
<220> FEATURE:
<223> OTHER INFORMATION: Description of Unknown:
JH124 sequence

<400> SEQUENCE: 337

Cys Ala Ser Ser Leu Gly Leu Gly Asp Glu Gln Phe Phe
1 5 10

<210> SEQ ID NO 338
<211> LENGTH: 13
<212> TYPE: PRT
<213> ORGANISM: Unknown
<220> FEATURE:
<223> OTHER INFORMATION: Description of Unknown:
JH124 sequence

<400> SEQUENCE: 338

Cys Ala Ser Phe Arg Gln Val Asn Tyr Gly Tyr Thr Phe
1 5 10

<210> SEQ ID NO 339
<211> LENGTH: 14
<212> TYPE: PRT
<213> ORGANISM: Unknown
<220> FEATURE:
<223> OTHER INFORMATION: Description of Unknown:
JH124 sequence

<400> SEQUENCE: 339

Cys Ala Ser Ser Phe Arg Gln Gly Ser Tyr Glu Gln Tyr Phe
1 5 10

<210> SEQ ID NO 340
<211> LENGTH: 10
<212> TYPE: PRT
<213> ORGANISM: Unknown
<220> FEATURE:
<223> OTHER INFORMATION: Description of Unknown:
JH124 sequence

<400> SEQUENCE: 340

Cys Ala Ser Ser Pro Asp Ile Gln Tyr Phe
1 5 10

<210> SEQ ID NO 341
<211> LENGTH: 12
<212> TYPE: PRT
<213> ORGANISM: Unknown
<220> FEATURE:
<223> OTHER INFORMATION: Description of Unknown:
JH124 sequence

<400> SEQUENCE: 341

Cys Ala Ser Ser Glu Thr Gly Trp Gly Ala Phe Phe
1 5 10

<210> SEQ ID NO 342
<211> LENGTH: 13
<212> TYPE: PRT
<213> ORGANISM: Unknown
<220> FEATURE:
<223> OTHER INFORMATION: Description of Unknown:
JH124 sequence

<400> SEQUENCE: 342

Cys Ala Ser Arg Arg His Ser Asn Gln Pro Gln His Phe
1 5 10

<210> SEQ ID NO 343
<211> LENGTH: 15
<212> TYPE: PRT
<213> ORGANISM: Unknown
<220> FEATURE:
<223> OTHER INFORMATION: Description of Unknown:
JH124 sequence

<400> SEQUENCE: 343

Cys Ala Ser Ser Leu Val Gly Leu Ala Gly Asn Glu Gln Phe Phe
1 5 10 15

<210> SEQ ID NO 344
<211> LENGTH: 15
<212> TYPE: PRT
<213> ORGANISM: Unknown
<220> FEATURE:
<223> OTHER INFORMATION: Description of Unknown:
JH124 sequence

<400> SEQUENCE: 344

Cys Ala Ser Ser Pro Gln Asp Gln His Val Tyr Glu Gln Tyr Phe
1 5 10 15

-continued

```
<210> SEQ ID NO 345
<211> LENGTH: 13
<212> TYPE: PRT
<213> ORGANISM: Unknown
<220> FEATURE:
<223> OTHER INFORMATION: Description of Unknown:
      JH124 sequence

<400> SEQUENCE: 345

Cys Ala Ser Thr Leu Arg Val Asp Thr Glu Ala Phe Phe
1               5                   10
```